US012591216B1

(12) United States Patent
Wesorick

(10) Patent No.: US 12,591,216 B1
(45) Date of Patent: Mar. 31, 2026

(54) PATIENT-SPECIFIC MEDICAL DEVICES BASED ON BONE DENSITY AND PROCESSES FOR PRODUCING THE SAME

(71) Applicant: restor3d, Inc., Durham, NC (US)

(72) Inventor: Benjamin Wesorick, Durham, NC (US)

(73) Assignee: restor3d, Inc., Durham, NC (US)

(*) Notice: Subject to any disclaimer, the term of this patent is extended or adjusted under 35 U.S.C. 154(b) by 0 days.

(21) Appl. No.: 19/044,264

(22) Filed: Feb. 3, 2025

Related U.S. Application Data

(60) Provisional application No. 63/549,419, filed on Feb. 2, 2024.

(51) Int. Cl.
| | |
|---|---|
| *G05B 19/4099* | (2006.01) |
| *G16H 30/40* | (2018.01) |
| *G16H 50/70* | (2018.01) |

(52) U.S. Cl.
CPC ......... *G05B 19/4099* (2013.01); *G16H 30/40* (2018.01); *G16H 50/70* (2018.01); *G05B 2219/35134* (2013.01); *G05B 2219/49023* (2013.01)

(58) Field of Classification Search
None
See application file for complete search history.

(56) References Cited

U.S. PATENT DOCUMENTS

| | | |
|---|---|---|
| 1,428,247 A | 9/1922 | Morris |
| D220,184 S | 3/1971 | Boone |
| 3,872,519 A | 3/1975 | Giannestras et al. |
| D265,288 S | 7/1982 | McLean |
| 4,440,835 A | 4/1984 | Vignaud |
| 4,588,574 A | 5/1986 | Felder et al. |
| 4,829,152 A | 5/1989 | Rostoker et al. |
| D309,185 S | 7/1990 | Lockawich |
| D336,517 S | 6/1993 | Mckeown |

(Continued)

FOREIGN PATENT DOCUMENTS

| | | |
|---|---|---|
| CA | 2597617 A1 | 8/2006 |
| CA | 2903390 A1 | 9/2014 |

(Continued)

OTHER PUBLICATIONS

3D Printing for Orthopedic Implant, E-Plus-3D, https://www.eplus3d.com/3d-printing-for-orthopedic-implant.html, 2021, 7 pages.

(Continued)

*Primary Examiner* — Jason Lin
(74) *Attorney, Agent, or Firm* — Husch Blackwell LLP; Bryan D. Stewart

(57) ABSTRACT

Systems and processes for designing and generating personalized surgical implants and devices are described herein. In various embodiments, the process includes generating patient-specific implants designed for increased osseointegration and improved surgical outcomes. In various embodiments, the process includes extracting patient-specific data with one or more aspects of an anatomical feature, processing the one or more aspects of the anatomical feature to identify and classify a deformity, create a density map of the one or more aspects of the anatomical feature, and generating a patient-specific implant or device based on the deformity classification, the density map, or a combination thereof.

17 Claims, 43 Drawing Sheets

(56)           References Cited

U.S. PATENT DOCUMENTS

| | | | |
|---|---|---|---|
| 5,248,456 | A | 9/1993 | Evans, Jr. et al. |
| D358,211 | S | 5/1995 | Cohen |
| D358,647 | S | 5/1995 | Cohen et al. |
| 5,497,785 | A | 3/1996 | Viera |
| 5,497,786 | A | 3/1996 | Urick |
| 5,591,191 | A | 1/1997 | Kieturakis |
| 5,766,259 | A | 6/1998 | Sammarco |
| 5,947,965 | A | 9/1999 | Bryan |
| 6,183,519 | B1 | 2/2001 | Bonnin et al. |
| 6,419,491 | B1 | 7/2002 | Ricci et al. |
| 6,461,358 | B1 | 10/2002 | Faccioli et al. |
| D490,901 | S | 6/2004 | Schulter et al. |
| D493,890 | S | 8/2004 | Schulter et al. |
| 6,989,003 | B2 | 1/2006 | Wing et al. |
| D521,642 | S | 5/2006 | Dorahy |
| 7,048,741 | B2 | 5/2006 | Swanson |
| 7,125,423 | B2 | 10/2006 | Hazebrouck |
| D539,426 | S | 3/2007 | Callaghan |
| D593,202 | S | 5/2009 | Petersen |
| 7,534,270 | B2 | 5/2009 | Ball |
| D595,853 | S | 7/2009 | Hanson et al. |
| D598,094 | S | 8/2009 | Alber |
| D604,153 | S | 11/2009 | Wantz |
| 7,632,575 | B2 | 12/2009 | Justin et al. |
| 7,666,522 | B2 | 2/2010 | Justin et al. |
| D611,147 | S | 3/2010 | Hanson et al. |
| D618,800 | S | 6/2010 | Mayon et al. |
| D620,111 | S | 7/2010 | Courtney et al. |
| D623,749 | S | 9/2010 | Horton et al. |
| 7,819,614 | B2 | 10/2010 | Versino et al. |
| D628,344 | S | 11/2010 | Raviv |
| D653,756 | S | 2/2012 | Courtney et al. |
| 8,128,580 | B2 | 3/2012 | Fujimagari et al. |
| 8,142,886 | B2 | 3/2012 | Noble et al. |
| 8,157,866 | B2 | 4/2012 | Winslow et al. |
| D660,432 | S | 5/2012 | Braido |
| D660,966 | S | 5/2012 | Sheild |
| D666,298 | S | 8/2012 | Sibhatu et al. |
| 8,262,589 | B2 | 9/2012 | Lupton |
| 8,382,755 | B2 | 2/2013 | Austin et al. |
| D681,204 | S | 4/2013 | Farris et al. |
| D683,856 | S | 6/2013 | Chin et al. |
| 8,529,568 | B2 | 9/2013 | Bouadi |
| 8,532,806 | B1 * | 9/2013 | Masson ............... A61F 2/30942 |
| | | | 623/1.1 |
| D692,136 | S | 10/2013 | Tyber |
| 8,556,971 | B2 | 10/2013 | Lang |
| 8,632,597 | B2 | 1/2014 | Lappin |
| D700,700 | S | 3/2014 | Efinger |
| 8,715,362 | B2 | 5/2014 | Reiley et al. |
| D708,747 | S | 7/2014 | Curran et al. |
| 8,771,365 | B2 | 7/2014 | Bojarski et al. |
| 8,781,557 | B2 * | 7/2014 | Dean ...................... A61B 5/103 |
| | | | 128/923 |
| 8,845,743 | B2 | 9/2014 | Termanini |
| 8,870,889 | B2 * | 10/2014 | Frey ....................... B33Y 80/00 |
| | | | 606/96 |
| D722,693 | S | 2/2015 | Kaufmann et al. |
| 8,945,229 | B2 | 2/2015 | Lappin |
| 8,945,230 | B2 | 2/2015 | Lang et al. |
| 8,951,260 | B2 | 2/2015 | Lang et al. |
| 8,965,088 | B2 | 2/2015 | Tsougarakis et al. |
| 9,020,788 | B2 | 4/2015 | Lang et al. |
| 9,034,237 | B2 | 5/2015 | Sperry et al. |
| 9,044,330 | B2 | 6/2015 | Chavarria et al. |
| 9,055,953 | B2 | 6/2015 | Lang et al. |
| D734,460 | S | 7/2015 | Froidevaux |
| D735,860 | S | 8/2015 | Palinchik et al. |
| D736,384 | S | 8/2015 | Palinchik et al. |
| 9,095,353 | B2 | 8/2015 | Burdulis, Jr. et al. |
| 9,095,439 | B2 | 8/2015 | Lian |
| 9,144,500 | B2 | 9/2015 | Harding, Jr. |
| 9,180,029 | B2 | 11/2015 | Hollister et al. |
| 9,186,257 | B2 | 11/2015 | Geisler et al. |
| D747,485 | S | 1/2016 | Oi |
| 9,295,482 | B2 | 3/2016 | Fitz et al. |
| 9,308,053 | B2 | 4/2016 | Bojarski et al. |
| 9,308,091 | B2 | 4/2016 | Lang |
| 9,326,780 | B2 | 5/2016 | Wong et al. |
| 9,333,058 | B1 | 5/2016 | Krastev |
| 9,351,743 | B2 | 5/2016 | Kehres et al. |
| 9,358,018 | B2 | 6/2016 | Fitz et al. |
| 9,364,896 | B2 | 6/2016 | Christensen et al. |
| 9,370,426 | B2 | 6/2016 | Gabbrielli et al. |
| 9,402,726 | B2 | 8/2016 | Linderman et al. |
| 9,408,615 | B2 | 8/2016 | Fitz et al. |
| 9,408,686 | B1 | 8/2016 | Miller et al. |
| 9,414,927 | B2 | 8/2016 | Iannotti et al. |
| 9,415,137 | B2 | 8/2016 | Meridew et al. |
| D767,137 | S | 9/2016 | Lin |
| 9,433,707 | B2 | 9/2016 | Swords et al. |
| 9,439,767 | B2 | 9/2016 | Bojarski et al. |
| 9,486,226 | B2 | 11/2016 | Chao |
| 9,495,483 | B2 | 11/2016 | Steines et al. |
| 9,498,344 | B2 | 11/2016 | Hodorek et al. |
| 9,517,134 | B2 | 12/2016 | Lang |
| 9,532,880 | B2 | 1/2017 | Lappin |
| 9,561,115 | B2 | 2/2017 | Elahinia et al. |
| 9,579,106 | B2 | 2/2017 | Lo et al. |
| 9,579,110 | B2 | 2/2017 | Bojarski et al. |
| 9,597,130 | B2 | 3/2017 | Pappalardo et al. |
| 9,597,191 | B2 | 3/2017 | Muir et al. |
| 9,603,711 | B2 | 3/2017 | Bojarski et al. |
| 9,610,168 | B2 | 4/2017 | Terrill et al. |
| 9,636,226 | B2 | 5/2017 | Hunt |
| 9,636,229 | B2 | 5/2017 | Lang et al. |
| 9,649,178 | B2 | 5/2017 | Ali |
| 9,662,226 | B2 | 5/2017 | Wickham |
| 9,668,873 | B2 | 6/2017 | Winslow et al. |
| 9,675,471 | B2 | 6/2017 | Bojarski et al. |
| 9,681,956 | B2 | 6/2017 | Al Hares et al. |
| 9,687,945 | B2 | 6/2017 | Steines et al. |
| 9,688,026 | B2 | 6/2017 | Ho et al. |
| 9,694,541 | B2 | 7/2017 | Pruett et al. |
| 9,700,420 | B2 | 7/2017 | Fitz et al. |
| 9,700,424 | B2 | 7/2017 | Sanders et al. |
| 9,700,971 | B2 | 7/2017 | Lang |
| 9,737,367 | B2 | 8/2017 | Steines et al. |
| 9,750,613 | B2 | 9/2017 | Petteys |
| 9,782,270 | B2 | 10/2017 | Wickham |
| 9,788,972 | B2 | 10/2017 | Flickinger et al. |
| 9,839,438 | B2 | 12/2017 | Eash |
| 9,849,019 | B2 | 12/2017 | Miller et al. |
| 9,872,773 | B2 | 1/2018 | Lang et al. |
| D809,661 | S | 2/2018 | Mueller et al. |
| D813,394 | S | 3/2018 | DaCosta et al. |
| 9,907,670 | B2 | 3/2018 | DeRidder et al. |
| 9,910,935 | B2 | 3/2018 | Golway et al. |
| 9,913,723 | B2 | 3/2018 | Fitz et al. |
| 9,918,849 | B2 | 3/2018 | Morris et al. |
| 9,925,054 | B2 | 3/2018 | Siegler et al. |
| 9,943,370 | B2 | 4/2018 | Asseln et al. |
| 9,943,627 | B2 | 4/2018 | Zhou et al. |
| 9,949,839 | B2 | 4/2018 | Sander |
| 9,956,048 | B2 | 5/2018 | Bojarski et al. |
| 9,956,083 | B2 | 5/2018 | Humphrey |
| 9,962,209 | B2 | 5/2018 | Dacosta et al. |
| 9,999,513 | B2 | 6/2018 | Overes et al. |
| 10,034,757 | B2 | 7/2018 | Kovacs et al. |
| D829,909 | S | 10/2018 | Horton |
| D832,441 | S | 10/2018 | DaCosta et al. |
| 10,085,839 | B2 | 10/2018 | Wong et al. |
| D835,276 | S | 12/2018 | Humphrey |
| D835,277 | S | 12/2018 | Gottlieb |
| D835,278 | S | 12/2018 | Gottlieb |
| D835,788 | S | 12/2018 | Jones et al. |
| D835,977 | S | 12/2018 | Pastorino et al. |
| 10,183,442 | B1 | 1/2019 | Miller |
| 10,245,152 | B2 | 4/2019 | Kloss |
| 10,245,164 | B2 | 4/2019 | Muir et al. |
| D849,944 | S | 5/2019 | Dacosta |
| 10,278,823 | B1 | 5/2019 | Xue et al. |
| D850,620 | S | 6/2019 | Tyber |
| D855,184 | S | 7/2019 | Predick |

(56)  References Cited

U.S. PATENT DOCUMENTS

| | | |
|---|---|---|
| 10,357,377 B2 | 7/2019 | Nyahay et al. |
| D857,201 S | 8/2019 | Predick et al. |
| D858,769 S | 9/2019 | Barela et al. |
| 10,405,993 B2 | 9/2019 | Deransart et al. |
| 10,426,549 B2 | 10/2019 | Kehres et al. |
| 10,449,051 B2 | 10/2019 | Hamzey et al. |
| 10,485,670 B2 | 11/2019 | Maale |
| D870,288 S | 12/2019 | Dang et al. |
| 10,492,686 B2 | 12/2019 | Hunter et al. |
| D873,031 S | 1/2020 | Martensson |
| D875,939 S | 2/2020 | DaCosta et al. |
| D877,907 S | 3/2020 | Linder et al. |
| D878,589 S | 3/2020 | Linder et al. |
| D878,590 S | 3/2020 | Linder et al. |
| D879,295 S | 3/2020 | Abbasi |
| D879,961 S | 3/2020 | Linder et al. |
| 10,583,012 B1 | 3/2020 | Longobardi |
| D881,665 S | 4/2020 | Zemel et al. |
| 10,624,746 B2 | 4/2020 | Jones et al. |
| 10,667,924 B2 | 6/2020 | Nyahay et al. |
| 10,736,751 B2 | 8/2020 | Hodorek et al. |
| 10,744,001 B2 | 8/2020 | Sack |
| D899,900 S | 10/2020 | Blanco |
| 10,806,597 B2 * | 10/2020 | Sournac .................. A61F 2/447 |
| 10,898,206 B2 | 1/2021 | Dacosta et al. |
| 10,937,542 B1 * | 3/2021 | Yildirim .................. G06T 7/11 |
| 10,940,015 B2 | 3/2021 | Sack |
| D917,697 S | 4/2021 | Reed et al. |
| 11,033,394 B2 | 6/2021 | Hamzey et al. |
| 11,090,161 B2 | 8/2021 | Hodorek |
| 11,135,771 B1 | 10/2021 | Reith et al. |
| D938,033 S | 12/2021 | Dang et al. |
| D942,623 S | 2/2022 | Cain |
| D942,624 S | 2/2022 | Cain |
| D944,400 S | 2/2022 | Cain |
| 11,273,048 B2 | 3/2022 | Cain et al. |
| 11,324,525 B1 | 5/2022 | Garvey et al. |
| 11,353,277 B2 | 6/2022 | Muceus et al. |
| 11,432,934 B2 | 9/2022 | Couture et al. |
| 11,439,726 B2 | 9/2022 | Spence et al. |
| D967,960 S | 10/2022 | Wang et al. |
| 11,471,203 B2 | 10/2022 | Sutika |
| D968,614 S | 11/2022 | Cain |
| 11,484,413 B1 | 11/2022 | Miller et al. |
| 11,490,907 B2 | 11/2022 | Mulqueen et al. |
| 11,564,802 B2 | 1/2023 | Ball et al. |
| D986,728 S | 5/2023 | Jou et al. |
| 11,648,125 B2 | 5/2023 | Ng |
| 11,666,367 B2 | 6/2023 | Goradia |
| 11,666,452 B2 | 6/2023 | Melkent et al. |
| D992,116 S | 7/2023 | Miller et al. |
| 11,744,716 B2 | 9/2023 | Jebsen et al. |
| 11,771,561 B2 | 10/2023 | Running et al. |
| 11,819,415 B2 | 11/2023 | Metcalfe et al. |
| 11,833,055 B2 | 12/2023 | Hatzidakis et al. |
| 11,839,389 B2 | 12/2023 | Termanini |
| 11,850,144 B1 | 12/2023 | Garrigues |
| 11,850,158 B2 | 12/2023 | Simoes et al. |
| 11,883,040 B2 | 1/2024 | Bonin, Jr. et al. |
| D1,013,875 S | 2/2024 | Miller et al. |
| D1,013,876 S | 2/2024 | Miller et al. |
| 11,950,822 B2 | 4/2024 | Champagne et al. |
| 11,960,266 B1 | 4/2024 | Kelly et al. |
| D1,030,046 S | 6/2024 | Boey et al. |
| 12,023,102 B2 | 7/2024 | Gutierrez et al. |
| 12,048,626 B2 | 7/2024 | Winslow et al. |
| 12,053,389 B2 | 8/2024 | Frankle |
| 12,178,455 B2 | 12/2024 | Neichel et al. |
| 2001/0031966 A1 | 10/2001 | Tormala et al. |
| 2004/0049284 A1 | 3/2004 | German et al. |
| 2004/0049285 A1 | 3/2004 | Haas |
| 2004/0064187 A1 | 4/2004 | Ball et al. |
| 2004/0148032 A1 | 7/2004 | Rutter et al. |
| 2004/0230313 A1 | 11/2004 | Saunders |
| 2005/0010302 A1 | 1/2005 | Dietz et al. |

| | | |
|---|---|---|
| 2006/0063135 A1 * | 3/2006 | Mehl ..................... G06F 18/28 |
| | | 433/213 |
| 2006/0074492 A1 | 4/2006 | Frey |
| 2006/0249875 A1 | 11/2006 | Robb et al. |
| 2007/0055251 A1 | 3/2007 | Huebner et al. |
| 2007/0100346 A1 | 5/2007 | Wyss et al. |
| 2007/0118243 A1 * | 5/2007 | Schroeder ............. A61F 2/2875 |
| | | 700/98 |
| 2007/0244563 A1 | 10/2007 | Roche et al. |
| 2008/0091271 A1 | 4/2008 | Bonitati et al. |
| 2008/0319448 A1 * | 12/2008 | Lavallee ................. G06F 30/00 |
| | | 703/11 |
| 2009/0093668 A1 | 4/2009 | Marten et al. |
| 2009/0182430 A1 | 7/2009 | Tyber et al. |
| 2010/0055644 A1 | 3/2010 | Arni |
| 2010/0137990 A1 | 6/2010 | Apatsidis et al. |
| 2010/0168798 A1 | 7/2010 | Clineff et al. |
| 2010/0286791 A1 | 11/2010 | Goldsmith |
| 2011/0054611 A1 | 3/2011 | Wu et al. |
| 2011/0190898 A1 | 8/2011 | Lenz et al. |
| 2011/0224796 A1 | 9/2011 | Weiland et al. |
| 2011/0230974 A1 | 9/2011 | Musani |
| 2012/0064288 A1 | 3/2012 | Nakano et al. |
| 2012/0209392 A1 | 8/2012 | Angibaud et al. |
| 2012/0239152 A1 | 9/2012 | Ullrich, Jr. et al. |
| 2012/0257507 A1 | 10/2012 | Sato et al. |
| 2012/0259419 A1 | 10/2012 | Brown et al. |
| 2013/0046313 A1 | 2/2013 | Lian |
| 2013/0068968 A1 | 3/2013 | Daniel |
| 2013/0123935 A1 | 5/2013 | Hunt et al. |
| 2013/0184820 A1 | 7/2013 | Schwartz et al. |
| 2013/0197657 A1 | 8/2013 | Anca et al. |
| 2013/0274890 A1 | 10/2013 | Mckay |
| 2014/0039633 A1 | 2/2014 | Roche et al. |
| 2014/0100779 A1 | 4/2014 | Horvitz et al. |
| 2014/0107786 A1 | 4/2014 | Geisler et al. |
| 2014/0236299 A1 | 8/2014 | Roeder et al. |
| 2014/0277443 A1 | 9/2014 | Fleury et al. |
| 2014/0277452 A1 | 9/2014 | Skaer |
| 2014/0336680 A1 | 11/2014 | Medina et al. |
| 2014/0350688 A1 | 11/2014 | Michel et al. |
| 2014/0371863 A1 | 12/2014 | Vanasse et al. |
| 2015/0025666 A1 | 1/2015 | Olivieri et al. |
| 2015/0105858 A1 | 4/2015 | Papay et al. |
| 2015/0328004 A1 * | 11/2015 | Mafhouz .................. A61F 2/36 |
| | | 700/98 |
| 2015/0335434 A1 | 11/2015 | Patterson et al. |
| 2015/0343709 A1 | 12/2015 | Gerstle et al. |
| 2015/0351915 A1 | 12/2015 | Defelice et al. |
| 2015/0374411 A1 | 12/2015 | Ehmke et al. |
| 2016/0045317 A1 * | 2/2016 | Lang ................... A61F 2/30942 |
| | | 700/98 |
| 2016/0051371 A1 | 2/2016 | Defelice et al. |
| 2016/0089138 A1 | 3/2016 | Early et al. |
| 2016/0143749 A1 | 5/2016 | Holovacs et al. |
| 2016/0151833 A1 | 6/2016 | Tsao |
| 2016/0193055 A1 | 7/2016 | Ries |
| 2016/0199193 A1 | 7/2016 | Willis et al. |
| 2016/0213487 A1 | 7/2016 | Wilson et al. |
| 2016/0213488 A1 | 7/2016 | Moore et al. |
| 2016/0220288 A1 | 8/2016 | Dubois et al. |
| 2016/0228255 A1 | 8/2016 | Samuelson et al. |
| 2016/0256279 A1 * | 9/2016 | Sanders ................... A61F 2/28 |
| 2016/0270931 A1 * | 9/2016 | Trieu ................... A61F 2/4637 |
| 2016/0296285 A1 * | 10/2016 | Chaoui ................. G16H 40/63 |
| 2016/0303793 A1 | 10/2016 | Ermoshkin et al. |
| 2016/0333152 A1 | 11/2016 | Cook et al. |
| 2016/0374829 A1 | 12/2016 | Vogt et al. |
| 2017/0014169 A1 | 1/2017 | Dean et al. |
| 2017/0018919 A1 | 1/2017 | Chen et al. |
| 2017/0020685 A1 | 1/2017 | Geisler et al. |
| 2017/0036403 A1 | 2/2017 | Ruff et al. |
| 2017/0042697 A1 | 2/2017 | Mcshane, III et al. |
| 2017/0056179 A1 | 3/2017 | Lorio |
| 2017/0066873 A1 | 3/2017 | Gardet |
| 2017/0105844 A1 | 4/2017 | Kuyler et al. |
| 2017/0143494 A1 * | 5/2017 | Mahfouz .............. A61F 2/4609 |
| 2017/0156880 A1 | 6/2017 | Halverson et al. |
| 2017/0165085 A1 | 6/2017 | Lechmann et al. |

(56) References Cited

U.S. PATENT DOCUMENTS

| | | | |
|---|---|---|---|
| 2017/0165790 A1 | 6/2017 | McCarthy et al. | |
| 2017/0172758 A1 | 6/2017 | Field et al. | |
| 2017/0182222 A1 | 6/2017 | Paddock et al. | |
| 2017/0209274 A1 | 7/2017 | Beerens et al. | |
| 2017/0239054 A1 | 8/2017 | Engstrand et al. | |
| 2017/0239064 A1 | 8/2017 | Cordaro | |
| 2017/0245998 A1 | 8/2017 | Padovani et al. | |
| 2017/0252165 A1 | 9/2017 | Sharp et al. | |
| 2017/0258606 A1 | 9/2017 | Afzal | |
| 2017/0282455 A1 | 10/2017 | Defelice et al. | |
| 2017/0296244 A1 | 10/2017 | Schneider et al. | |
| 2017/0304063 A1 | 10/2017 | Hatzidakis et al. | |
| 2017/0319344 A1 | 11/2017 | Hunt | |
| 2017/0323037 A1 | 11/2017 | Schroeder | |
| 2017/0333205 A1 | 11/2017 | Joly et al. | |
| 2017/0354510 A1 | 12/2017 | O'Neil et al. | |
| 2017/0354513 A1 | 12/2017 | Maglaras et al. | |
| 2017/0355815 A1 | 12/2017 | Becker et al. | |
| 2017/0360488 A1 | 12/2017 | Kowalczyk et al. | |
| 2017/0360563 A1 | 12/2017 | Hunt et al. | |
| 2017/0360578 A1 | 12/2017 | Shin et al. | |
| 2017/0367843 A1 | 12/2017 | Eisen et al. | |
| 2017/0367845 A1 | 12/2017 | Eisen et al. | |
| 2018/0008419 A1 | 1/2018 | Tyber et al. | |
| 2018/0012517 A1 | 1/2018 | Ropelato et al. | |
| 2018/0022017 A1 | 1/2018 | Fukumoto et al. | |
| 2018/0064540 A1 | 3/2018 | Hunt et al. | |
| 2018/0085230 A1 | 3/2018 | Hunt | |
| 2018/0098858 A1 | 4/2018 | Valderrabano et al. | |
| 2018/0104063 A1 | 4/2018 | Asaad | |
| 2018/0110593 A1 | 4/2018 | Khalil | |
| 2018/0110626 A1 | 4/2018 | Mcshane, III et al. | |
| 2018/0110627 A1 | 4/2018 | Sack | |
| 2018/0113992 A1* | 4/2018 | Eltorai ................. A61F 2/4261 | |
| 2018/0117219 A1 | 5/2018 | Yang et al. | |
| 2018/0147319 A1 | 5/2018 | Colucci-Mizenko et al. | |
| 2018/0196920 A1 | 7/2018 | Liang et al. | |
| 2018/0256336 A1 | 9/2018 | Mueller et al. | |
| 2018/0263782 A1 | 9/2018 | Lang et al. | |
| 2018/0280140 A1 | 10/2018 | Jones et al. | |
| 2018/0289380 A1 | 10/2018 | Mauldin et al. | |
| 2018/0289515 A1 | 10/2018 | Nemes et al. | |
| 2019/0159907 A1 | 5/2019 | Roche et al. | |
| 2019/0167433 A1 | 6/2019 | Allen et al. | |
| 2019/0262101 A1 | 8/2019 | Shanjani et al. | |
| 2019/0269527 A1 | 9/2019 | Moore | |
| 2019/0302736 A1 | 10/2019 | Chanin | |
| 2019/0343652 A1 | 11/2019 | Petersheim et al. | |
| 2020/0000595 A1 | 1/2020 | Jones et al. | |
| 2020/0030102 A1 | 1/2020 | Mullens et al. | |
| 2020/0030108 A1 | 1/2020 | Orphanos et al. | |
| 2020/0046512 A1 | 2/2020 | Newman et al. | |
| 2020/0085452 A1 | 3/2020 | Siegler | |
| 2020/0085585 A1 | 3/2020 | Siegler | |
| 2020/0113656 A1* | 4/2020 | Jo ......................... A61C 8/0037 | |
| 2020/0155321 A1 | 5/2020 | Dikovsky et al. | |
| 2020/0171752 A1 | 6/2020 | Rogren | |
| 2020/0171753 A1 | 6/2020 | Satko et al. | |
| 2020/0188121 A1 | 6/2020 | Boux De Casson et al. | |
| 2020/0253649 A1 | 8/2020 | Langdale et al. | |
| 2020/0367910 A1 | 11/2020 | Hafez et al. | |
| 2021/0000588 A1 | 1/2021 | Cain | |
| 2021/0038401 A1 | 2/2021 | Ball et al. | |
| 2021/0059822 A1* | 3/2021 | Casey ................... A61F 2/4425 | |
| 2021/0077276 A1 | 3/2021 | Garvey et al. | |
| 2021/0110605 A1 | 4/2021 | Haslam et al. | |
| 2021/0113222 A1 | 4/2021 | Khatibi et al. | |
| 2021/0121298 A1 | 4/2021 | Walker et al. | |
| 2021/0196288 A1 | 7/2021 | Hodorek et al. | |
| 2021/0216683 A1 | 7/2021 | Rai et al. | |
| 2021/0298908 A1 | 9/2021 | Holmes et al. | |
| 2021/0307765 A1 | 10/2021 | Dumpe et al. | |
| 2021/0340334 A1 | 11/2021 | Portela et al. | |
| 2022/0023048 A1 | 1/2022 | Nolens et al. | |
| 2022/0087670 A1 | 3/2022 | Selmoune | |

| | | | |
|---|---|---|---|
| 2022/0110757 A1 | 4/2022 | Paterson | |
| 2022/0134639 A1 | 5/2022 | Allen et al. | |
| 2022/0142783 A1 | 5/2022 | Ahmadi | |
| 2022/0168109 A1 | 6/2022 | Giordano et al. | |
| 2022/0226094 A1 | 7/2022 | Chotkowski et al. | |
| 2022/0249241 A1 | 8/2022 | Orbay et al. | |
| 2022/0296386 A1 | 9/2022 | Fang et al. | |
| 2022/0401138 A1 | 12/2022 | Finley et al. | |
| 2022/0409140 A1* | 12/2022 | Cordonnier ............ G16H 30/40 | |
| 2023/0096120 A1 | 3/2023 | Longobardi | |
| 2023/0111847 A1* | 4/2023 | Leclercq ............... A61F 2/3859 |
| | | | 703/11 |
| 2023/0122922 A1 | 4/2023 | Daudet | |
| 2023/0137504 A1 | 5/2023 | Gilotra et al. | |
| 2023/0138162 A1* | 5/2023 | Winston ................. A61B 34/10 |
| | | | 700/98 |
| 2023/0190492 A1 | 6/2023 | Marks et al. | |
| 2024/0033092 A1 | 2/2024 | Parthasarathy et al. | |
| 2024/0065767 A1* | 2/2024 | Cordonnier ............ G16H 20/40 | |
| 2024/0346768 A1* | 10/2024 | Crawford ................. G06N 3/08 | |
| 2025/0213365 A1 | 7/2025 | Varadarajan et al. | |

FOREIGN PATENT DOCUMENTS

| | | | |
|---|---|---|---|
| CN | 109567913 A | 4/2019 | |
| CN | 110090096 A | 8/2019 | |
| EP | 1180989 B1 | 4/2006 | |
| EP | 2832321 A1 | 2/2015 | |
| EP | 2635239 B1 | 7/2017 | |
| EP | 2913030 B1 | 3/2018 | |
| EP | 3586800 A1 | 1/2020 | |
| EP | 4434496 A1 | 9/2024 | |
| FR | 3071400 A1 | 3/2019 | |
| KR | 301007894 S | 5/2019 | |
| WO | 2014020562 A1 | 2/2014 | |
| WO | 2015054070 A1 | 4/2015 | |
| WO | 2015191361 A1 | 12/2015 | |
| WO | 2020123295 A1 | 6/2020 | |
| WO | 2020231657 A1 | 11/2020 | |
| WO | 2020252308 A1 | 12/2020 | |
| WO | 2023183793 A2 | 9/2023 | |
| WO | 2024015899 A2 | 1/2024 | |
| WO | 2024020216 A1 | 1/2024 | |
| WO | 2024137512 A1 | 6/2024 | |
| WO | 2025067730 A1 | 4/2025 | |

OTHER PUBLICATIONS

Additive Orthopaedics, "Additive Orthopaedics 3d Printed Cotton Bone Segment", retrieved from: https://web.archive.org/web/20200919145251/https:/www.additiveorthopaedics.com/our-products/cotton/, 2019, 3 pages.

Alt, Sami. "Design for Sterilization Part 1: Steam Sterillization." Material, Material Technology Blog, Jun. 3, 2016, 3 pages.

Cera-Metal orthopedic implant coating, ifdesign.com, Accessed Jul. 24, 2024, https://ifdesign.com/en/winner-ranking/projecUcera-metal/27188., 5 pages.

Cotton Wedge Portfolio with TIDAL Technology™, restor3d, retrieved from: https://assets-global.website-files.com/65d612f03cc5c490660ab482/65d612f03cc5c490660ab7b9_MKG-002%20Rev02%20Jun2023_Cotton%20Osteotomy%20Wedges%20Sales%20Sheet-2.pdf, 2023, 2 pages.

Disclosure by Applicant re: surgical plan dated Mar. 27, 2024, 12 pages.

Ducheyne, "Comprehensive Biomaterials" Comprehensive Biomaterials, vol. 1, Elsevier, 2011, p. 135.

Extended European Search Report received for EP Patent Application No. 20196410.3, mailed on Feb. 12, 2021, 11 pages.

Indiamart, "Anterior Cervical Fusion Cage for Spine Surgery", accessed Dec. 9, 2020 on https://www.indiamart.com/proddetail/anterior-cervical-fusion-cage-12402896897.html, 8 pages.

Instagram, "restor3d", first available Jul. 21, 2020 on https://www.instagram.com/p/CC6dzt0AKcM/?utm_source=ig_web_copy_link, 2 pages.

(56) References Cited

OTHER PUBLICATIONS

Larraona et al., "Radiopaque material for 3D printing scaffolds", XXXV Congreso Anual de la Sociedad Espanola de Ingenieria Biomedica. Bilbao, Nov. 29-Dec. 1, 2017, pp. 451-454.

Miller et al., "Fatigue of Injection Molded and 3D Printed Polycarbonate Urethane in Solution",Polymer, vol. 108, 2017, pp. 121-134.

Miller et al., Deformation and Fatigue of Tough 3D Printed Elastomer Scaffolds Processed by Fused Deposition Modeling and Continuous Liquid Interface Production, Journal of Mechanical Behavior of Biomedical Materials, vol. 75, 2017, pp. 1-13.

MTP Hemiarthroplasty Implant Featuring TIDAL Technology™, resto3d, retrieved from: https://cdn.prod.website-files.com/65d612f03cc5c490660ab482/65d612f03cc5c490660ab7aa_restor3d-MTP-Sales-Sheet.pdf, 2023, 2 pages.

NTop, "3D printing implants: A complete guide", Retrieved from: https://www.ntop.com/resources/blog/3d-printing-implants-a-complete-guide/, Feb. 1, 2023, 21 pages.

Ratnovsky et al., "Mechanical Properties of Different Airway Stents", Medical Engineering and Physics, vol. 37, 2015, pp. 408-415.

Restor3d, "Products—Designed with surgeons for tailored clinical solutions", Retrieved from: https://web.archive.org/web/20200928123335/https:/restor3d.com/products, 2020, 5 pages.

Rozema et al., The Effects of Different Steam-Sterilization Programs on Material Properties of Poly(L-lactide), Journal of Applied Biomaterials, vol. 2, 1991, pp. 23-28.

Sandberg, "Nvision Biomedical Technologies: First FDA Clearance for Osteotomy Wedge System", Ortho Spine News, retrieved from: https://orthospinenews.com/2020/10/28/nvision-biomedical-technologies-first-fda-clearance-for-osteotomy-wedge-system-made-of-peek-optima-ha-enhanced/, 2020, 9 pages.

Sandberg, "SeaSpine Announces 25,000th NanoMetalene Implantation", Ortho Spine News, Retrieved from: https://orthospinenews.com/2019/12/18/seaspine-announces-25000th-nanometalene-implantation/, Dec. 18, 2019, 10 pages.

Sina, "Application logic of triple periodic minimum surface", retrieved from: https://k.sina.com.cn/article_2422410454_90630cd600100tlbm.html?from=science, Oct. 24, 2020, 6 pages.

Yakacki et al., "Does 3D Printing Add Value In Orthopedics?", ODT, retrieved from: https://www.odtmag.com/does-3d-printing-add-value-in-orthopedics/, Mar. 29, 2019, 16 pages.

Yan et al., "Microstructure and mechanical properties of aluminum alloy cellular lattice structures manufactured by direct metal laser sintering", Materials Science and Engineering A, vol. 628, 2015, pp. 238-246.

Yan et al., "Ti—6Al—4V Triply Periodic Minimal Surface Structures for Bone Implants Fabricated Via Selective Laser Melting", Journal of the Mechanical Behavior of Biomedical Materials, vol. 51, 2015, pp. 61-73.

Yosra K., "Johnson & Johnson Medical has acquired 3D-printed spinal implants specialist, Emerging Implant Technologies (EIT)", 3D Adept Media Retrieved from: https://3dadept.com/johnson-johnson-medical-has-acquired-3d-printed-spmplants-specialist-emerging-implant-technologies/, Sep. 17, 2018, 4 pages.

* cited by examiner

105

115

900+ HU

450 HU

0 HU

305

115

900+ HU

450 HU

0 HU

500

900+ HU

450 HU

0 HU

1200

115

900+ HU

450 HU

0 HU

1300

1310

1320

1325

1330

1325

1705 — Receive patient image(s) and deformity output

1700

1710 — Extract pixels from patient image

1715 — Assign density category to each pixel

1720 — Assign a weight to each density category

1725 — Process input patient image and deformity output using trained model

1730 — Generate adjusted output

PATIENT-SPECIFIC MEDICAL DEVICES BASED ON BONE DENSITY AND PROCESSES FOR PRODUCING THE SAME

CROSS REFERENCE TO RELATED APPLICATIONS

This application claims priority to U.S. Provisional Patent Application No. 63/549,419, entitled "BONE DENSITY MAPPING SYSTEMS AND PROCESSES," filed on Feb. 2, 2024, the entirety of which is incorporated by reference.

This application also incorporates by reference U.S. patent application Ser. No. 18/454,580, entitled "PATIENT-SPECIFIC MEDICAL DEVICES AND ADDITIVE MANUFACTURING PROCESSES FOR PRODUCING THE SAME," filed on Aug. 23, 2023, U.S. patent application Ser. No. 18/627,137, entitled "TOTAL ANKLE REPLACEMENT SYSTEM AND PROCESSES FOR MAKING AND USING THE SAME," filed on Jul. 4, 2024, U.S. patent application Ser. No. 18/192,362, entitled "KINEMATIC AND PARAMETERIZED MODELING FOR PATIENT-ADAPTED IMPLANTS, TOOLS, AND SURGICAL PROCEDURES," filed Mar. 29, 2023, U.S. patent application Ser. No. 15/955,355, entitled "ADVANCE METHODS AND TECHNIQUES FOR DESIGNING KNEE IMPLANT COMPONENTS," filed Apr. 17, 2018, and U.S. patent application Ser. No. 15/982,551, entitled "METHODS AND DEVICES RELATED TO PATIENT-ADAPTED HIP JOINT IMPLANTS," filed on May 17, 2018, all of which are incorporated herein in their entireties.

BRIEF SUMMARY OF THE DISCLOSURE

Medical imaging, particularly CT scans, generates grayscale of patient anatomy. Some scanning technologies produce images with slight visible differences in the image based on different densities of the anatomy (e.g., bone appears more dense than organs, etc.). However, existing medical technologies lack the ability to identify and objectively classify a density level of one or more portions of patient anatomy on a pixel-by-pixel or voxel-by-voxel basis. Existing medical imaging processes may apply a general classification to an area of interest, but do not classify the density of patient anatomy on a pixel-by-pixel or voxel-by-voxel basis, thus reducing the accuracy of the density output.

As a result, there is a long-felt, but unsolved need for improved medical image processing techniques to objectively classify the density of patient anatomy on a pixel-by-pixel or voxel-by-voxel basis.

It is generally understood that pixel-by-pixel or voxel-by-voxel analysis of medical images is computationally heavy/expensive and the standard (grayscale density) is thus routinely accepted and thus, there has been a lack of technological advancement in this area. Briefly described, and according to one embodiment, aspects of the present disclosure generally relate to systems and processes for mapping bone density on a pixel-by-pixel or voxel-by-voxel basis using objective classification techniques and one or more artificial intelligence models. The systems and processes described herein can also include intelligently generating recommended medical device placement (e.g., a surgical plan) and/or medical device design based on the mapped bone density. For example, the systems and processes may be used to analyze the bone density of one or more portions of a patient's anatomy and generate a recommended location for the medical device and/or fixation components for securing the medical device. The systems and processes described herein can be used to design and generate medical devices as well as surgical planning and implementation of the medical device.

According to a first aspect, the present disclosure relates to a medical device production process comprising populating a database with a plurality of patient-specific device files classified by one or more attributes associated with one or more anatomical features; receiving a 2D patient-specific grayscale image file associated with a shoulder of a patient; generating a 3D digital representation of the shoulder of a patient based on the 2D patient-specific grayscale image file using a non-rigid shape reference; processing the 3D digital representation of the shoulder including: identifying a deformity associated with the shoulder based on at least one of the one or more anatomical features; classifying the deformity of the shoulder based on an attribute of the one or more attributes; and determining a density mapping of the shoulder using an intelligent density mapping model, wherein the density mapping is determined on a voxel-by-voxel basis; retrieving at least one of the plurality of patient-specific device files classified by the attribute of the one or more attributes; creating an initial baseplate system design based on the at least one of the plurality of patient-specific device files, the initial baseplate system design comprising a fixation member and a plurality of screw holes, wherein each of the fixation member and the one or more screw holes are oriented at one or more angles; creating an updated baseplate system design by adjusting at least one angle of the one or more angles of each of the fixation member and the plurality of screw holes based on the density mapping; and transmitting a digital representation of at least a portion of the updated baseplate system design to a 3D printer for manufacturing at least a portion of a baseplate system based on the updated baseplate system design.

According to a second aspect, the medical device production process of the first aspect, or any other aspect, wherein the baseplate system comprises at least a portion of the fixation member, the plurality of screw holes, or a combination thereof.

According to a third aspect, the medical device production process of the second aspect, or any other aspect, wherein one or more of the fixation member and the plurality of screw holes are integrally formed with an implant device.

According to a fourth aspect, the medical device production process of the third aspect, or any other aspect, wherein each screw hole of the plurality of screw holes is oriented at an angle based on the deformity classification, the density mapping, or combination thereof.

According to a fifth aspect, the medical device production process of the first aspect, or any other aspect, wherein determining the density mapping of the shoulder further comprises extracting voxels from the patient-specific 3D digital representation; assigning a density category of a plurality of density categories to each of the extracted voxels; assigning a weight to each of the plurality of density categories; and processing the patient-specific 3D digital representation file via an artificial intelligence model to create the density mapping based on the weight of each of the plurality of density categories assigned to each of the extracted voxels.

According to a sixth aspect, the medical device production process of the first aspect, or any other aspect, wherein the deformity associated with the shoulder is provided in the form of a glenoid deformity that is identified at least in part by comparing the patient-specific grayscale image file to the plurality of patient-specific device files.

According to a seventh aspect, the medical device production process of the first aspect, or any other aspect, wherein the initial baseplate system design is based on a compilation of the plurality of patient-specific device files.

According to an eighth aspect, the medical device production process of the first aspect, or any other aspect, wherein the digital representation is generated at least in part by processing the one or more attributes associated with the one or more anatomical features, the plurality of patient-specific device files, and the density mapping via an artificial intelligence model.

According to a ninth aspect, the present disclosure also relates to a medical device production process comprising populating a database with a plurality of patient-specific device files classified by one or more attributes associated with one or more anatomical features; receiving a patient-specific grayscale image file associated with a shoulder of a patient; and processing the patient-specific grayscale image file including: identifying a deformity associated with the shoulder based on at least one of the one or more anatomical features; classifying the deformity of the shoulder based on an attribute of the one or more attributes; and determining a density mapping of the shoulder using an intelligent density mapping model; retrieving at least one of the plurality of patient-specific device files classified by the attribute of the one or more attributes; creating an initial baseplate system design based on the at least one of the plurality of patient-specific device files, the initial baseplate system design comprising a fixation member at an angle; creating an updated baseplate system design by adjusting the angle of the fixation member based on the density mapping; and transmitting a digital representation of at least a portion of the updated baseplate system design to a 3D printer for manufacturing at least a portion of a baseplate system based on the updated baseplate system design.

According to a tenth aspect, the medical device production process of the ninth aspect, or any other aspect, wherein the updated baseplate system design comprises a configuration for at least a portion of the fixation member, a plurality of screw holes, or a combination thereof.

According to an eleventh aspect, the medical device production process of the tenth aspect, or any other aspect, wherein one or more of the fixation member, and the plurality of screw holes are integrally formed with an implant device.

According to a twelfth aspect, the medical device production process of the eleventh aspect, or any other aspect, wherein each screw hole of the plurality of screw holes is oriented at an angle based on the deformity classification, the density mapping, or combination thereof.

According to a thirteenth aspect, the medical device production process of the ninth aspect, or any other aspect, wherein the baseplate system comprises at least a portion of the fixation member, a plurality of screw holes, or a combination thereof.

According to a fourteenth aspect, the medical device production process of the ninth aspect, or any other aspect, wherein determining the density mapping of the shoulder further comprises: extracting pixels from the patient-specific grayscale image file; assigning a density category of a plurality of density categories to each of the extracted pixels; assigning a weight to each of the plurality of density categories; and processing the patient-specific grayscale image file via an artificial intelligence model to create the density mapping based on the weight of each of the plurality of density categories assigned to each of the extracted pixels.

According to a fifteenth aspect, the medical device production process of the ninth aspect, or any other aspect, wherein the deformity associated with the shoulder is provided in the form of a glenoid deformity that is identified at least in part by comparing the patient-specific grayscale image file to the plurality of patient-specific device files.

According to a sixteenth aspect, the medical device production process of the ninth aspect, or any other aspect, wherein the initial baseplate system design is based on a compilation of the plurality of patient-specific device files.

According to a seventeenth aspect, the medical device production process of the ninth aspect, or any other aspect, wherein the digital representation is generated at least in part by processing the one or more attributes associated with the one or more anatomical features, the plurality of patient-specific device files, and the density mapping via an artificial intelligence model.

According to an eighteenth aspect, the present disclosure also relates to a medical device production process comprising populating a database with a plurality of patient-specific device files classified by one or more attributes associated with one or more anatomical features; receiving a patient-specific grayscale image file associated with an anatomical feature of a patient; processing the patient-specific grayscale image file including: identifying a deformity associated with the anatomical feature of the patient based on a plurality of patient-specific device files; classifying the deformity of the anatomical feature of the patient based on an attribute of one or more attributes associated with the plurality of patient-specific device files; and determining a density mapping of the anatomical feature of the patient using an intelligent density mapping model; creating an initial implant system design based on at least one of the plurality of patient-specific device files, the initial implant system design comprising a feature; creating an updated implant system design by adjusting the feature based on the density mapping; and transmitting a digital representation of at least a portion of the updated implant system design to manufacture at least a portion of an implant system based on the updated implant system design.

According to a nineteenth aspect, the medical device production process of the eighteenth aspect, or any other aspect, wherein the implant system comprises at least a portion of the fixation member, the plurality of screw holes, or a combination thereof.

According to a twentieth aspect, the medical device production process of the nineteenth aspect, or any other aspect, wherein one or more of the fixation member and the plurality of screw holes are integrally formed with an implant device.

According to a twenty-first aspect, the present disclosure also relates to a bone density mapping process comprising: receiving a patient-specific grayscale image file associated with an anatomical feature of a patient; processing the patient-specific grayscale image file via an intelligent density mapping model including: extracting pixels or voxels from the patient-specific grayscale image file; determining a density classification of the anatomical feature of the patient, wherein the density classification is determined on a pixel-by-pixel basis; applying the density classification to the patient-specific grayscale image file; generating a colorized density-mapped patient-specific image file based on the output of the intelligent density mapping model; and transmitting the colorized density-mapped patient-specific image file to a display interface.

According to a twenty-second aspect, the bone density mapping process of the twenty-first aspect, or any other aspect, wherein determining the density classification of the anatomical feature of the patient further comprises: assigning a density category of a plurality of density categories to each of the extracted pixels or voxels; and creating the density mapping based on the weight of each of the plurality of density categories assigned to each of the extracted pixels or voxels.

According to a twenty-third aspect, the bone density mapping process of the twenty-first aspect, or any other aspect, further comprising: generating a CAD file for a patient-specific device based on the colorized density-mapped patient-specific image file.

According to a twenty-fourth aspect, the bone density mapping process of the twenty-first aspect, or any other aspect, further comprising: generating a surgical plan for the anatomical feature of the patient based on the colorized density-mapped patient-specific image file.

According to a twenty-fifth aspect, the bone density mapping process of the twenty-first aspect, or any other aspect, wherein the colorized density-mapped patient-specific image file is used to update a configuration of a patient-specific device.

According to a twenty-sixth aspect, the bone density mapping process of the twenty-fifth aspect, wherein updating the configuration of the patient-specific device includes adjusting an angle of a fixation device based on an output of the intelligent density mapping model.

According to a twenty-seventh aspect, the bone density mapping process of the twenty-first aspect, or any other aspect, wherein the patient-specific device comprises a patient-specific implant.

According to a twenty-eighth aspect, the present disclosure also relates to a patient-specific medical device comprising: a 3D-printed body, the 3D-printed body defining at least one opening for receiving a fixation device, wherein a design of the 3D-printed body is produced at least in part by an intelligent density mapping model based on a density classification of an anatomical feature of a patient, the 3D-printed body comprising: a metallic material; and a patient-specific surface derived from an artificial intelligence model based on one or more aspects of the anatomical feature of the patient.

According to a twenty-ninth aspect, the patient-specific medical device of the twenty-eighth aspect, or any other aspect, wherein the intelligent density mapping model includes executing instructions for: determining a density classification of the anatomical feature of the patient, wherein the density classification is determined on a pixel-by-pixel basis of a patient-specific grayscale image file; and applying the density classification to the patient-specific grayscale image file.

According to a thirtieth aspect, the patient-specific medical device of the twenty-eighth aspect, or any other aspect, wherein the 3D-printed body design is based at least in part on a compilation of a plurality of patient-specific device files associated with the anatomical feature of the patient.

According to a thirty-first aspect, the patient-specific medical device of the thirtieth aspect, or any other aspect, wherein the 3D-printed body includes one or more screw holes designed at an angle based on the density mapping, the compilation of patient specific device files, or a combination thereof.

According to a thirty-second aspect, the patient-specific medical device of the twenty-eighth aspect, or any other aspect, wherein the patient-specific is for mating with a portion of the patient's bone anatomy.

It will be understood by those skilled in the art that one or more aspects of this disclosure can meet certain objectives, while one or more other aspects can lead to certain other objectives. Various modifications to the illustrated embodiments will be readily apparent to those skilled in the art, and the generic principles herein can be applied to other embodiments and applications without departing from embodiments of the disclosure. Other objects, features, benefits, and advantages of the present disclosure will be apparent in this summary and descriptions of the disclosed embodiments and will be readily apparent to those skilled in the art. Such objects, features, benefits, and advantages will be apparent from the above as taken in conjunction with the accompanying figures and all reasonable inferences to be drawn therefrom.

Figure 1A:
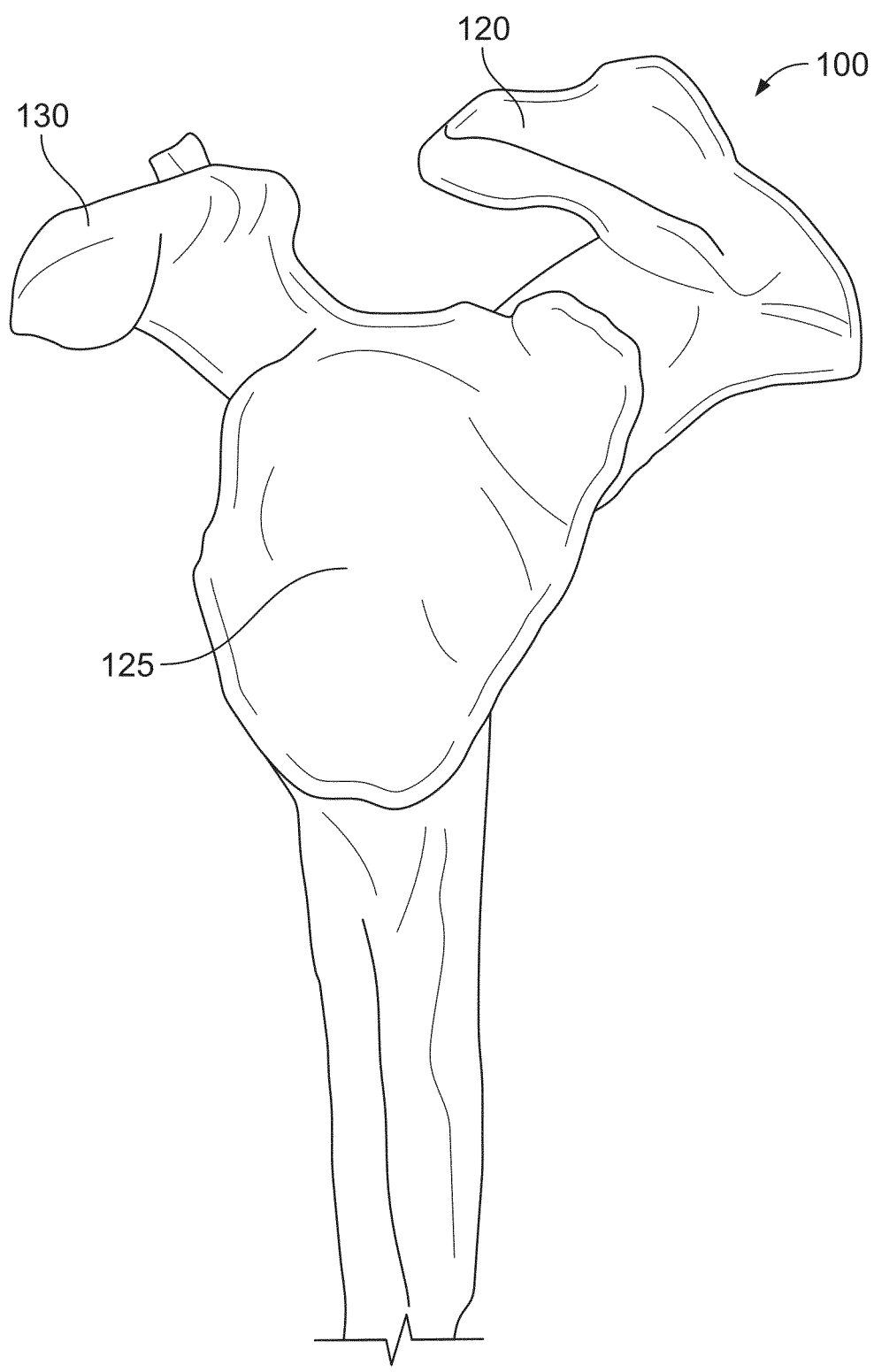
FIG. 1 (including FIG. 1A, FIG. 1B, and FIG. 1C) is a perspective view of a scapula image and a processed image based on the same, according to one embodiment.

While the disclosure is susceptible to various modifications and alternative forms, specific embodiments thereof are shown by way of example in the drawings and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure.

DETAILED DESCRIPTION

In one embodiment, the systems and processes discussed herein may be used for mapping density of one or more portions of patient anatomy. In at least one embodiment, the processes discussed herein may be used for intelligently generating medical devices and placement recommendations for the medical devices in surgical procedures. In at least one embodiment, the mapping processing discussed herein may be used for organs, bones, tissues, muscles, fat, fluids, air, kidney stones, foreign bodies, or other portions of a patient's anatomy. Although specific embodiments discussed herein include a scapula and a humerus, it will be appreciated that the systems and processes described herein can be applied to other bones, including but not limited to, bones of the ankle, hip, wrist, elbow, knee, feet, hands, or other bones in upper or lower extremities, spine, head, jaw and face, chest, and other suitable locations.

According to particular embodiments, the disclosure relates to a density mapping process applied to images of patient anatomy. In at least one embodiment, the process can further include identifying and classifying a deformity associated with an anatomical feature of patient's anatomy based on images of the patient anatomy. In some aspects, the deformity is identified and classified based on one or more attributes associated with the anatomical feature as compared to a database of patient-specific device files classified by one or more attributes associated with one or more anatomical features. In at least one embodiment, the systems and processes herein can include transforming the 2D images of the patient anatomy into a 3D digital representation of the anatomical feature of the patient using an artificial intelligence model. The density mapping process can generate a pixel-by-pixel or voxel-by-voxel objective classification of the density of the patient anatomy. It may be advantageous to identify and analyze the specific density of discrete portions of patient anatomy to design patient-specific devices and/or plan surgical procedures. For example, if a patient-specific device is designed with an input including both the deformity classification and the density classification of one or more portions of the patient anatomy, the patient-specific device can be designed and positioned relative to densities of the patient anatomy to promote osseointegration and improve surgical outcomes (e.g., improved fixation). In at least one embodiment, the patient-specific device can include an implant, instrument, surgical guide, cut guide, tools, fixation devices, or any other patient, consumer, animal-specific use-case, or other medical device.

In typical medical imaging, like a computed tomography (CT) scan for example, detailed internal images of a patient's anatomy can be obtained. CT scan images are generated in grayscale or black and white. CT scans typically use Hounsfield units (HU) as a quantitative scale for indicating the radiodensity of one or more substances, materials, and/or bodily tissues. In some embodiments, the present embodiment can be applied to a magnetic resonance imaging (MRI) scan. In a non-limiting example, the deformity classification and density mapping processes can be tailored for MRI scan processing, for example, by using increased segmentation, adjusting weights or scales to account for increased image compression of certain aspects of a patient's anatomy, etc.

Figure 1B:
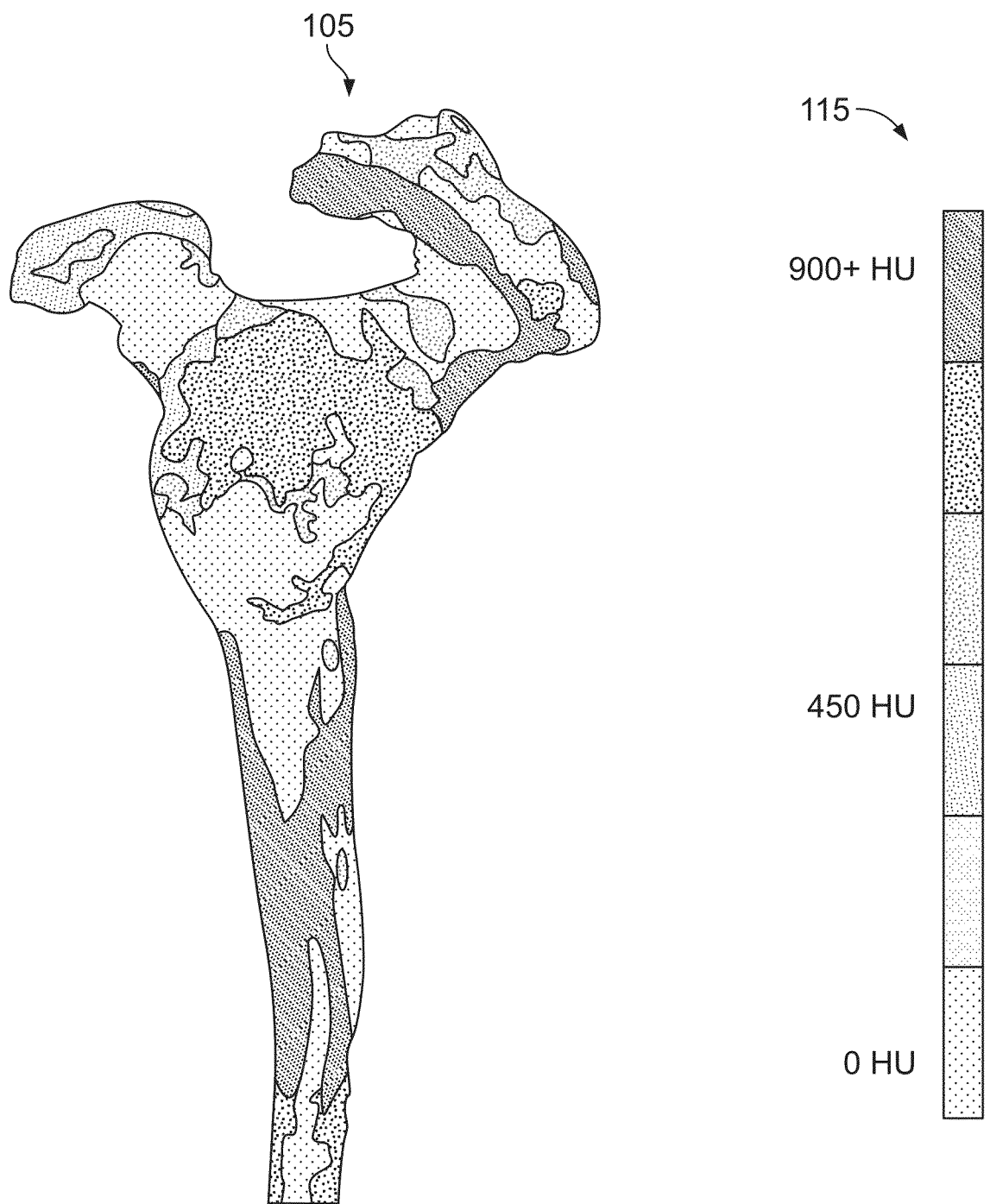
Figure 1C:
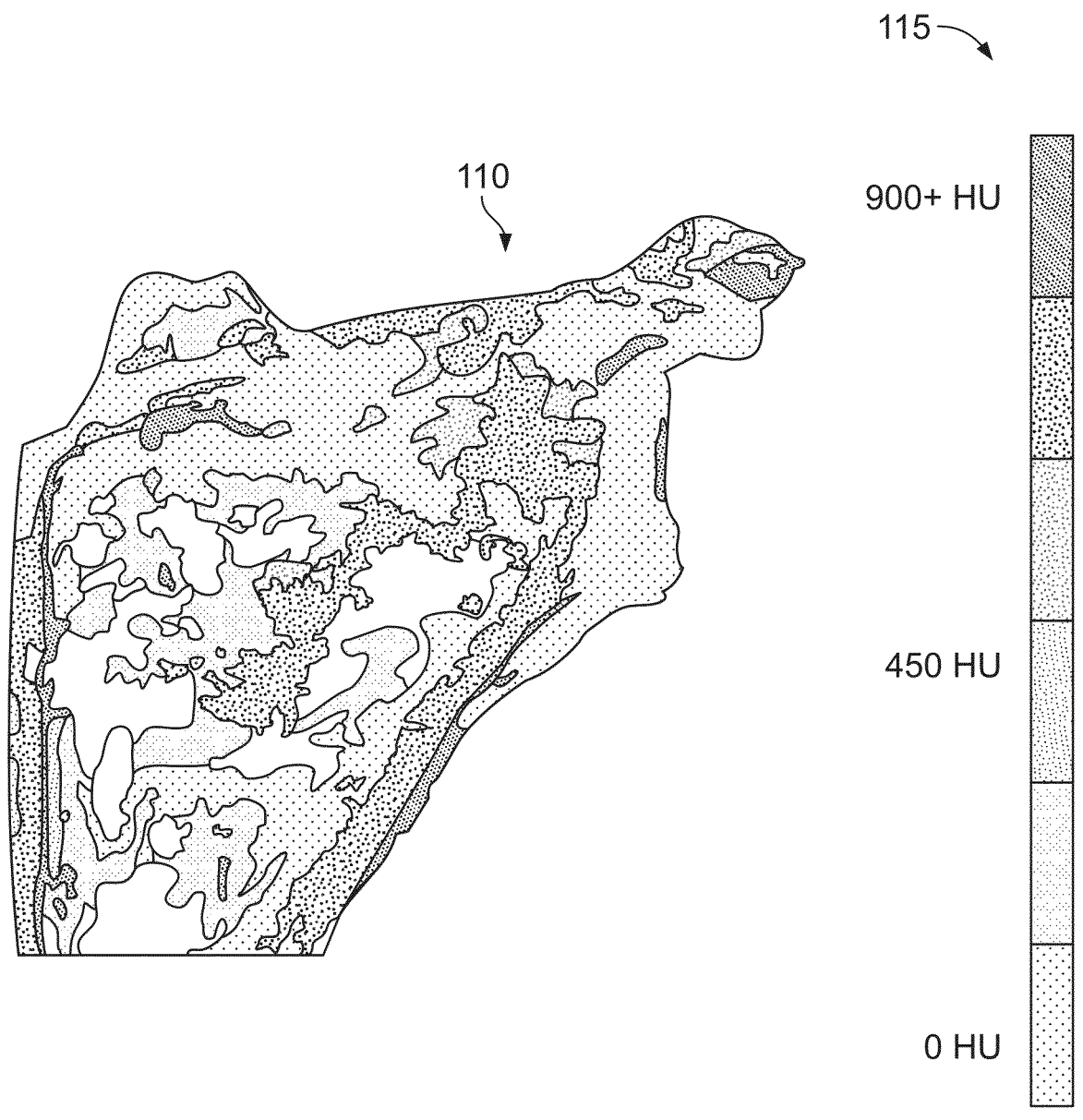

FIG. 1 illustrates a grayscale scapula image 100 (FIG. 1A), a colorized density-mapped scapula image 105 (FIG. 1B), an enlarged back side perspective view 110 of the colorized density-mapped scapula image 105 (FIG. 1C), and a colorized density classification scale 115 in HU. In at least one embodiment, the system applies the colorized density classification scale 115 on a pixel-by-pixel or voxel-by-voxel basis to the grayscale scapula image 100 in order to generate the colorized density-mapped scapula image 105. It will be appreciated that in some embodiments, the density-mapped image is not colorized and where used herein, a colorized density-mapped image may also be represented in a non-colorized density-mapped image. In at least one embodiment, the system applies the colorized density classification scale 115 using one or more artificial intelligence models, as described in more detail in connection with FIG. 20. In some embodiments, the colorized density-mapped scapula image 105 may be used for planning a shoulder surgery and/or designing a patient-specific device 205 (see FIG. 2) for a shoulder surgery. Generally speaking, the shoulder is a ball and socket joint that allows the arm to rotate in a circular fashion or to hinge out and up away from the body. The human shoulder is formed by a clavicle 130, a scapula 120, and a humerus 705 (see FIG. 7). The humerus 705 attaches to the scapula 120 (e.g., the humeral head 710 sits in the glenoid cavity 125).

Figure 2A:
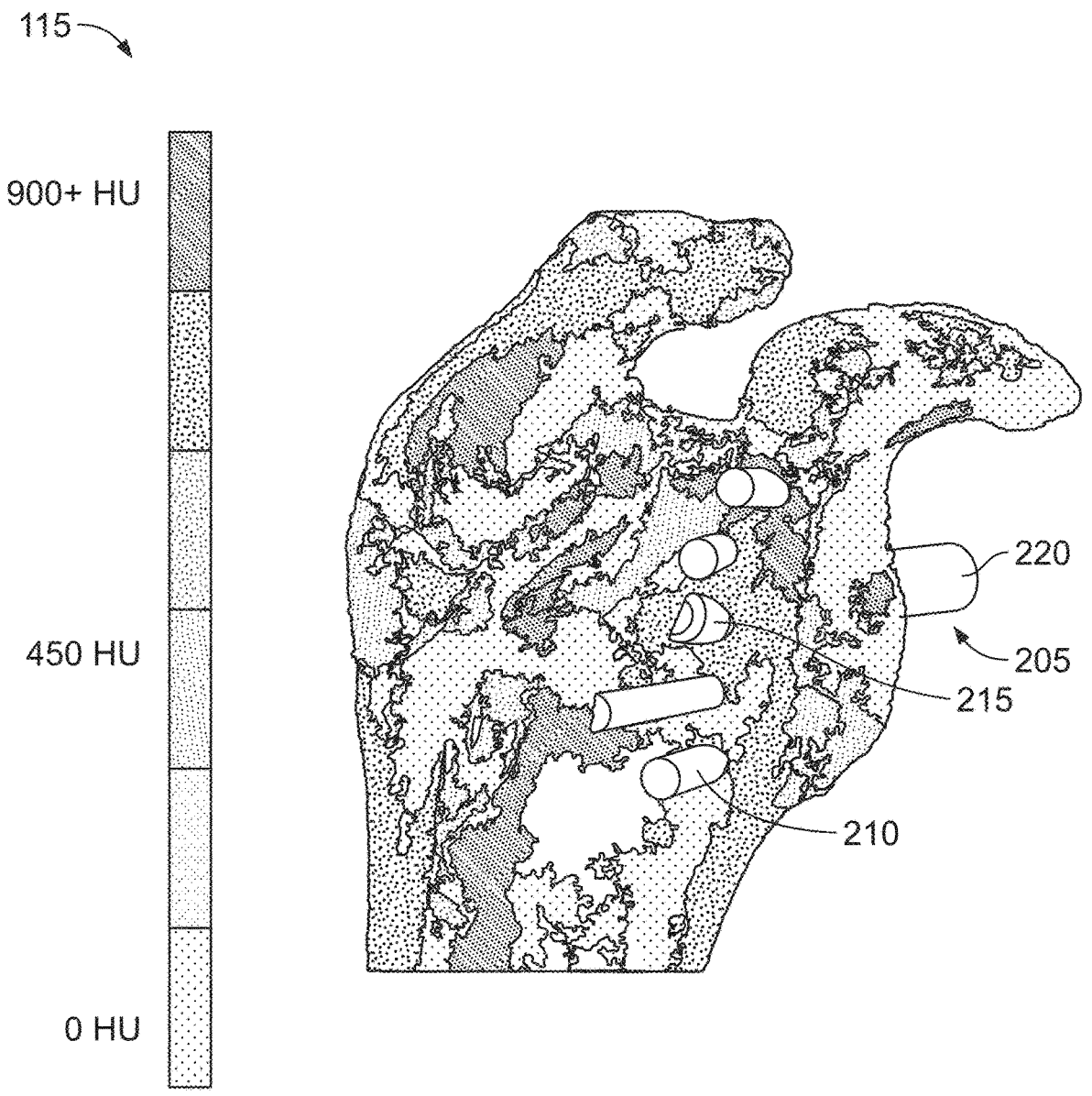
FIG. 2 (including FIG. 2A, FIG. 2B, and FIG. 2C) is a perspective view of a processed image of an implant installed in a patient's shoulder, according to one embodiment.
Figure 2B:
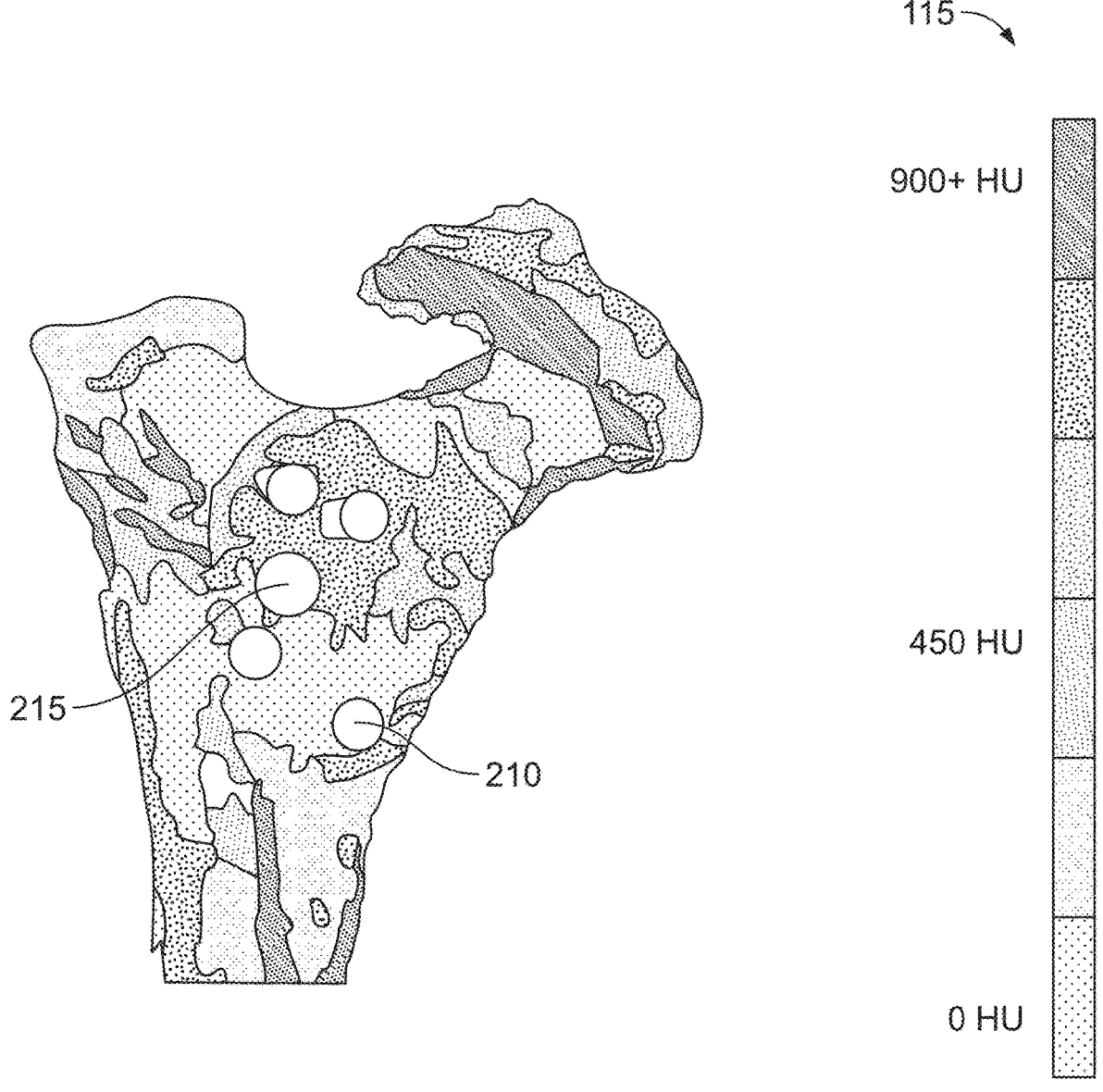
Figure 2C:
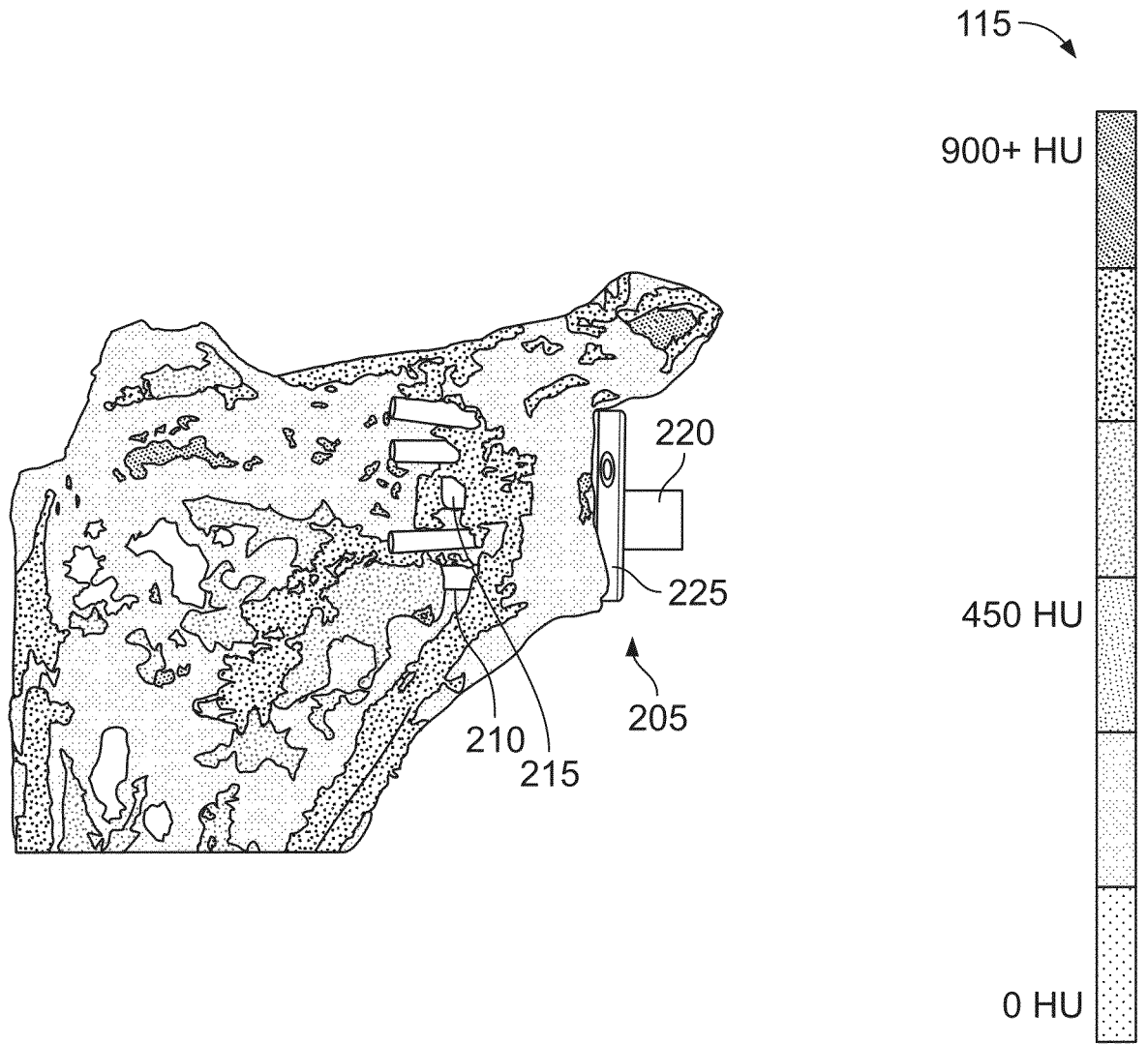

FIG. 2 illustrates an enlarged back side perspective view of a colorized density-mapped shoulder 200 with a patient-specific device 205 installed in FIG. 2A, a front side perspective view of the colorized density-mapped shoulder 200 with the patient specific device 205 (here a post, which may be part of or integrally formed with a baseplate or other component) installed in FIG. 2B, and a lateral side perspective view of the colorized density-mapped shoulder 200 with the patient specific device 205 installed in FIG. 2C. One such procedure utilizing the patient-specific device 205 may be a reverse shoulder arthroplasty (RSA) wherein damaged areas of bone around the patient's shoulder joint are removed and replaced with metal implants (or implants of any suitable material). An exemplary patient-specific device 205 is shown within the context of a partial RSA system and in accordance with the principles of this disclosure.

The patient-specific device 205 may include one or more surgical screws 210, a fixation member 215, the head of which may form at least a portion of a baseplate 225. In some embodiments, the fixation member 215 is provided in the form of a central surgical post, screw, or similar. The patient-specific device may also include an extrusion taper 220, designed to couple to a glenosphere (not shown). In some embodiments, the patient-specific device 205 can be provided in the form of an RSA replacement system including a humeral stem (not shown), a socket (not shown) disposed on one end of the humeral stem, and a glenosphere (not shown). The glenosphere, attached to the extrusion taper 220, may articulate with an artificial socket attached to the humorous such that the patient may perform the expected range of motion. The glenosphere and the baseplate 225 may be coupled to each other via the extrusion taper 220, and the fixation member 215 may be coupled to the underlying patient scapula 200, providing compression force of the glenosphere against the baseplate 225 and providing the potential for tissue in-growth with the surrounding bony (or soft tissue) structures (which may further stabilize the RSA system and/or patient shoulder).

In some embodiments, the patient-specific device 205 is provided in the form of a 3D-printed implant with one or more surgical screws 210, the fixation member 215, and the extrusion taper 220. In at least one embodiment, the patient-specific device 205 is designed with one or more apertures to secure the one or more screws 210 for fixation during a surgical procedure. In some embodiments, the one or more screws 210 can be provided in the form of a 3D-printed mono block surgical screw including a tip, a head, and a shaft extending between the tip and the head. In some embodiments, the shaft includes a shaft core, at least one thread, and at least one thread slot. In particular embodiments, at least one thread is disposed helically along the shaft and extends radially from the tip. The at least one thread slot may be disposed helically along the shaft and adjacent to the at least one thread and may extend radially from the tip. The shaft core may be hollow or solid or some combination thereof. The head may include a structure, such as an extrusion, that enables fixation. According to particular embodiments, the patient-specific device 205 may include a plurality of materials, each material associated with a different region or level of roughness or porosity. In some embodiments, the material of a particular aspect of the 3D-printed implant can be customized based on the density-classification of the patient anatomy to promote osseointegration.

In some forms, the patient-specific device 205 can be mapped to the patient's anatomy based on the density classification of the patient's anatomy. In some embodiments, the patient-specific device 205, or one or more aspects thereof, may vary in dimension and characteristics (e.g., length, width, height, depth, orientation, location of apertures, shape, size, contour, orientation of screws and screw hole angles, orientation of the fixation member and fixation member angle, etc.) depending on the patient's anatomical classifications and/or surgical specifications as determined based on an analysis and processing of the patient-specific image files using one or more of the deformity classification process and the density mapping process, described in more detail below in connection with FIGS. 16-18. In a non-limiting illustrative example, an angle of a first screw of a plurality of screws associated with a patient-specific device may be oriented (or the screw holes configured to orient the screw) at 20 degrees in an x-y plane. A second screw of a plurality of screws associated with the patient-specific device may be oriented (or the screw holes configured to orient the screw) at 35 degrees in a y-z plane. Although this non-limiting example embodiment describes two screws, one oriented in an x-y plane and the other oriented in a y-z plane, the one or more screws and fixation members may be disposed in any suitable orientation or angle in relation to the patient-specific device 205 and/or the patient anatomy without departing from the principles of this disclosure. It will also be appreciated that while only two screw orientations are discussed in connection with this non-limiting example, that there may be a plurality of screws oriented at different angles from one another in the same plane, different planes, or a combination thereof. In some embodiments, the angle associated with a screw of the plurality of screws may be about 10 to 20-degrees, about 15 to 25-degrees, about 20 to 30-degrees, about 25 to 35-degrees, about 30 to 40-degrees, about 35 to 45-degrees, 40 to 60-degrees, about 50 to 70-degrees, about 60 to 80-degrees, about 70 to 90-degrees, about 80 to 100-degrees, or any other suitable angle.

In some embodiments, the processes may be used to generate a design and/or recommendation for a particular screw configuration (e.g., size, shape, material, helical arrangement, surface texture, angle, orientation, location, etc.) based on the density of one or more portions of the patient's anatomy. In some embodiments, the system and processes may be used to produce one or more screw(s), rod(s), post(s), or other aspects of the patient-specific device (including the entire device) based on the density of one or more portions of the patient's anatomy and/or based on the design, recommendation, or other output from the density-mapping process, described in connection with FIG. 17. In some embodiments, the processes may be used to update an initial configuration or an initial design of a patient-specific device, or a portion thereof based on the density of one or more portions of the patient's anatomy.

In at least one embodiment, one or more surfaces of the 3D-printed implant, or aspects thereof, may include a porous region (e.g., a TPMS gyroid structure). For example, in one non-limiting embodiment, the one or more screws 210 and/or fixation member 215 are at least partially porous. In some embodiments, one or more aspects of the 3D-printed implant may be designed to be porous, partially porous, and/or smooth based on the density classification of the patient's anatomy. For example, depending on the use case (e.g., upper extremities, lower extremities, etc.), the type of patient anatomy to be contacted by the one or more aspects of the 3D-printed implant (e.g., bones, cartilage, etc.), and/or the density classification of the particular location of the patient's anatomy, the surface of the one or more aspects of the 3D-printed implant may be customized to increase osseointegration, stability, and range of motion. Further, a type of material used in an implant (3D-printed or otherwise produced) may be determined based on the density classification and/or other processes discussed herein.

Figure 3A:
FIG. 3 (including FIG. 3A, FIG. 3B, and FIG. 3C) is a perspective view of a scapula image and a processed image based on the same, according to one embodiment.
Figure 3B:
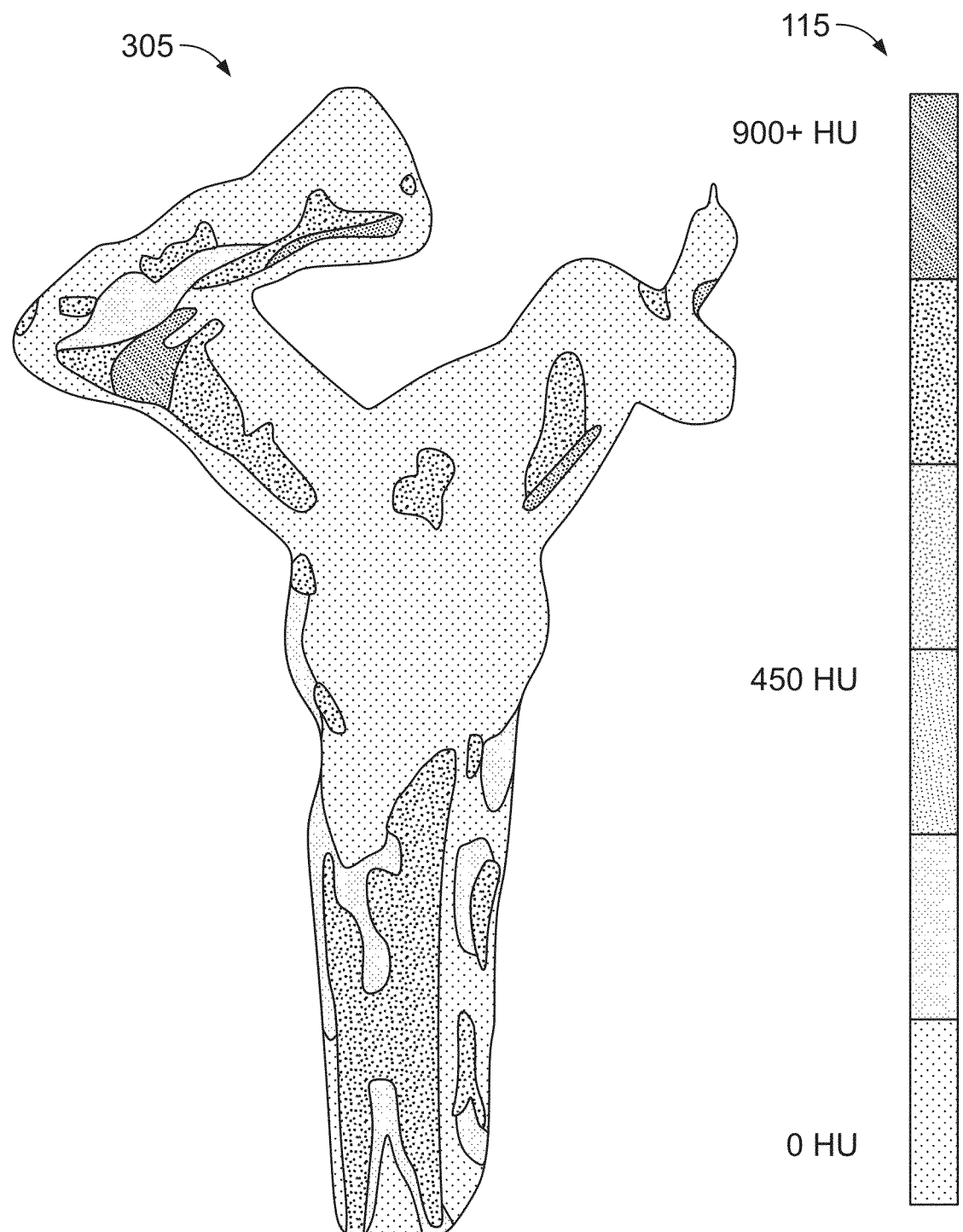
Figure 3C:
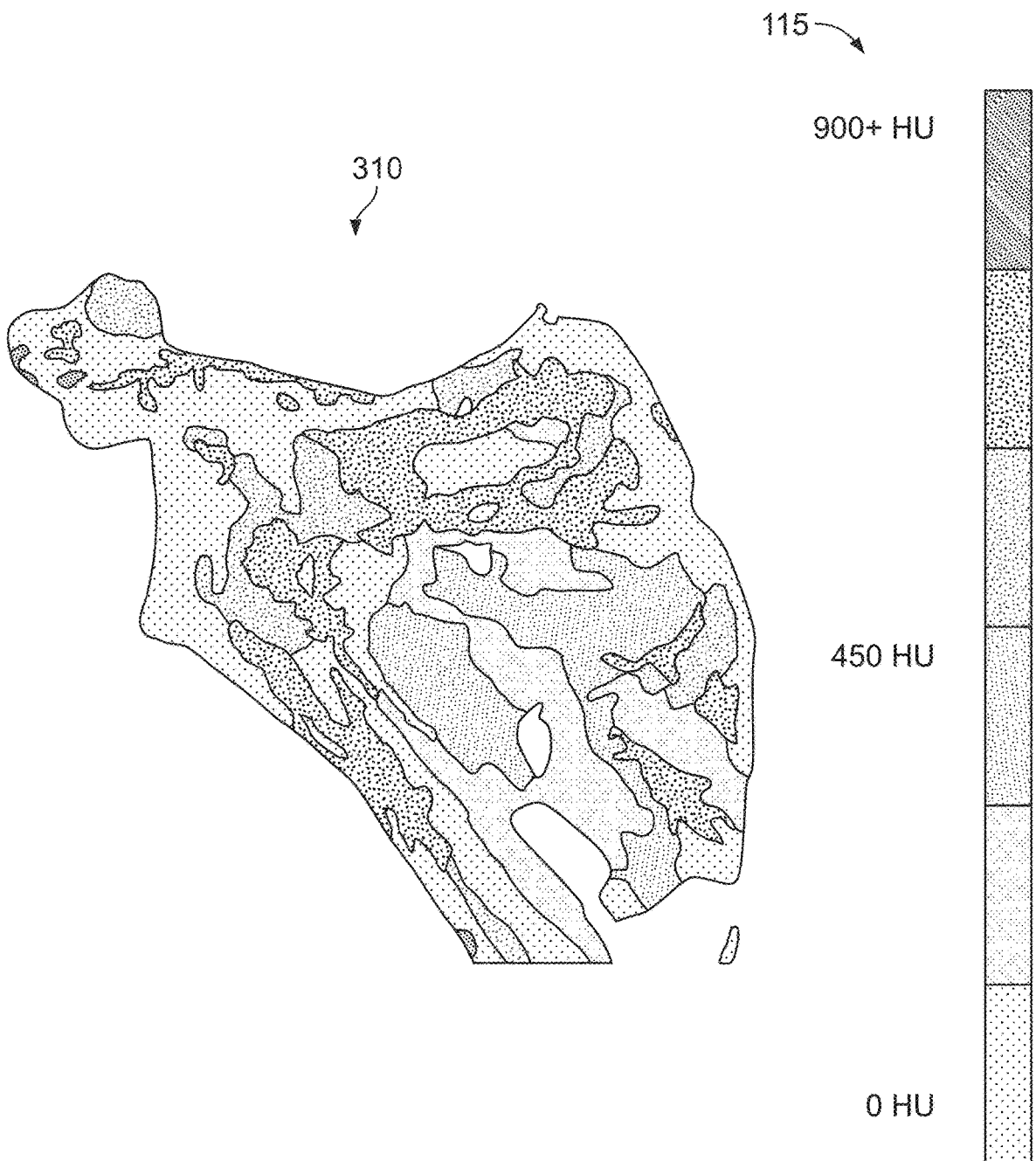

FIG. 3 illustrates another embodiment of a grayscale scapula image 600 (FIG. 3A), a colorized density-mapped scapula image 605 (FIG. 3B), an enlarged back side perspective view 610 of the colorized density-mapped scapula image 605 (FIG. 3C), and a colorized density classification scale 115 in HU.

Figure 4A:
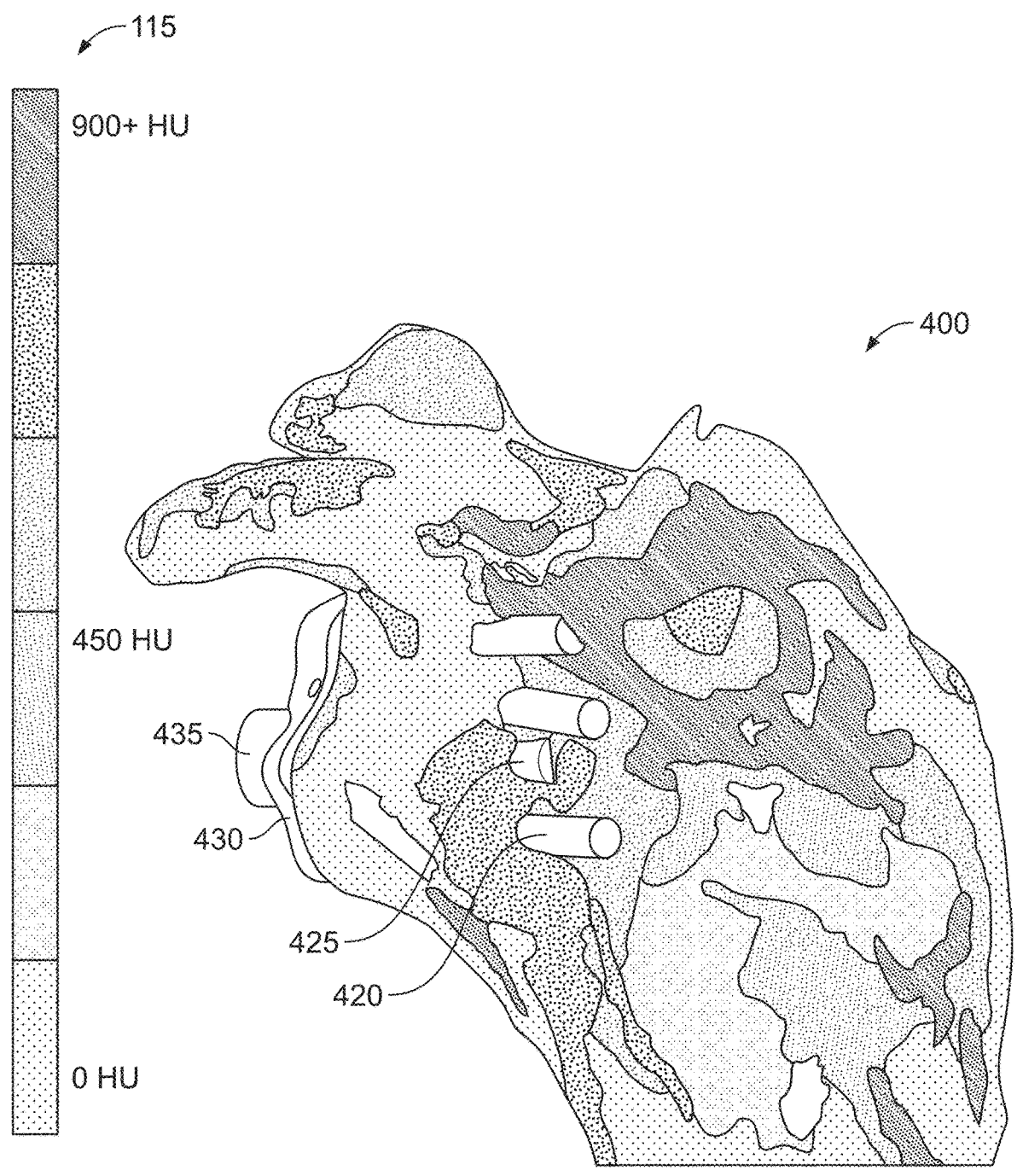
FIG. 4 (including FIG. 4A, FIG. 4B, and FIG. 4C) is a perspective view of a processed image of an implant installed in a patient's shoulder, according to one embodiment.
Figure 4B:
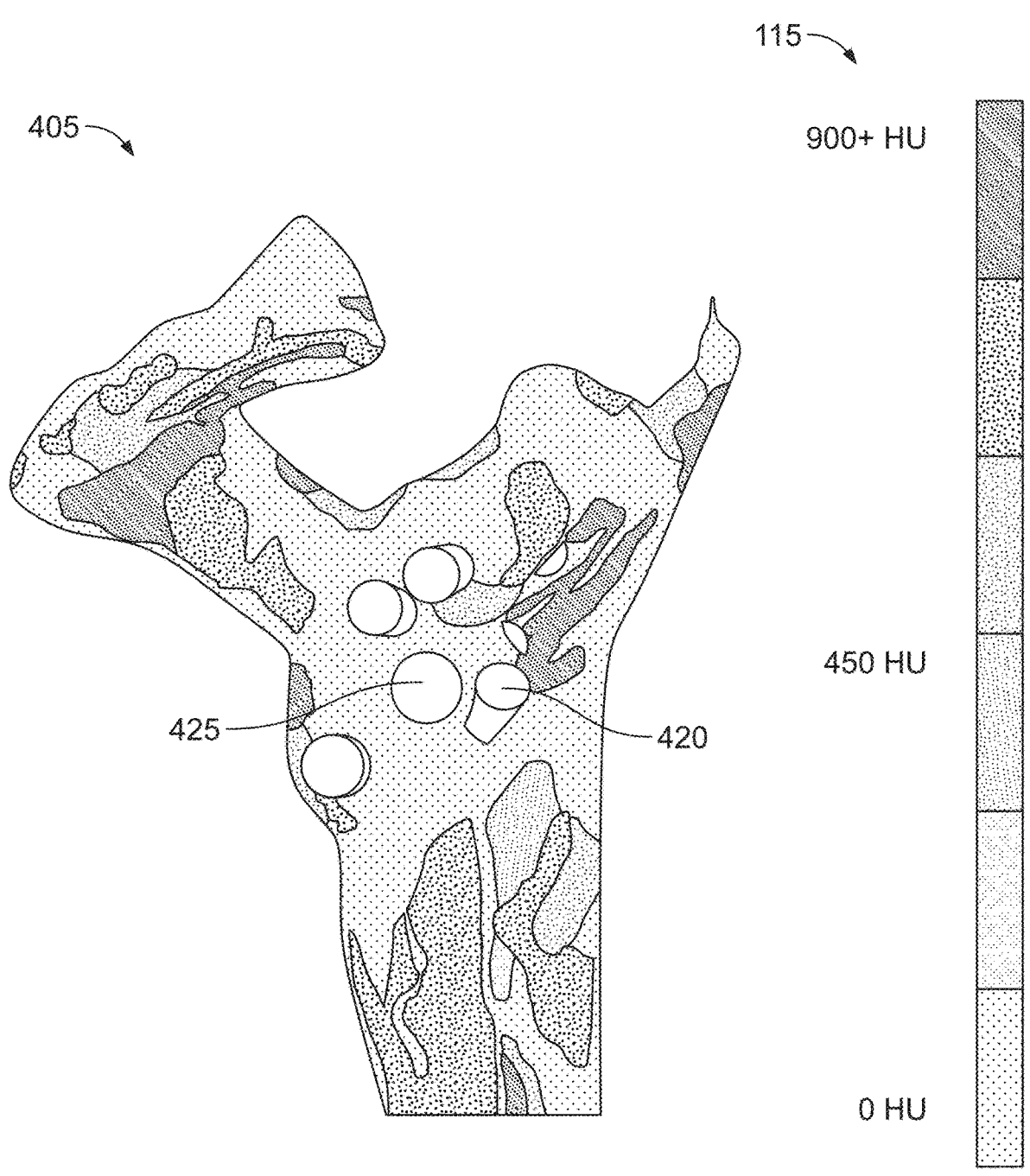
Figure 4C:
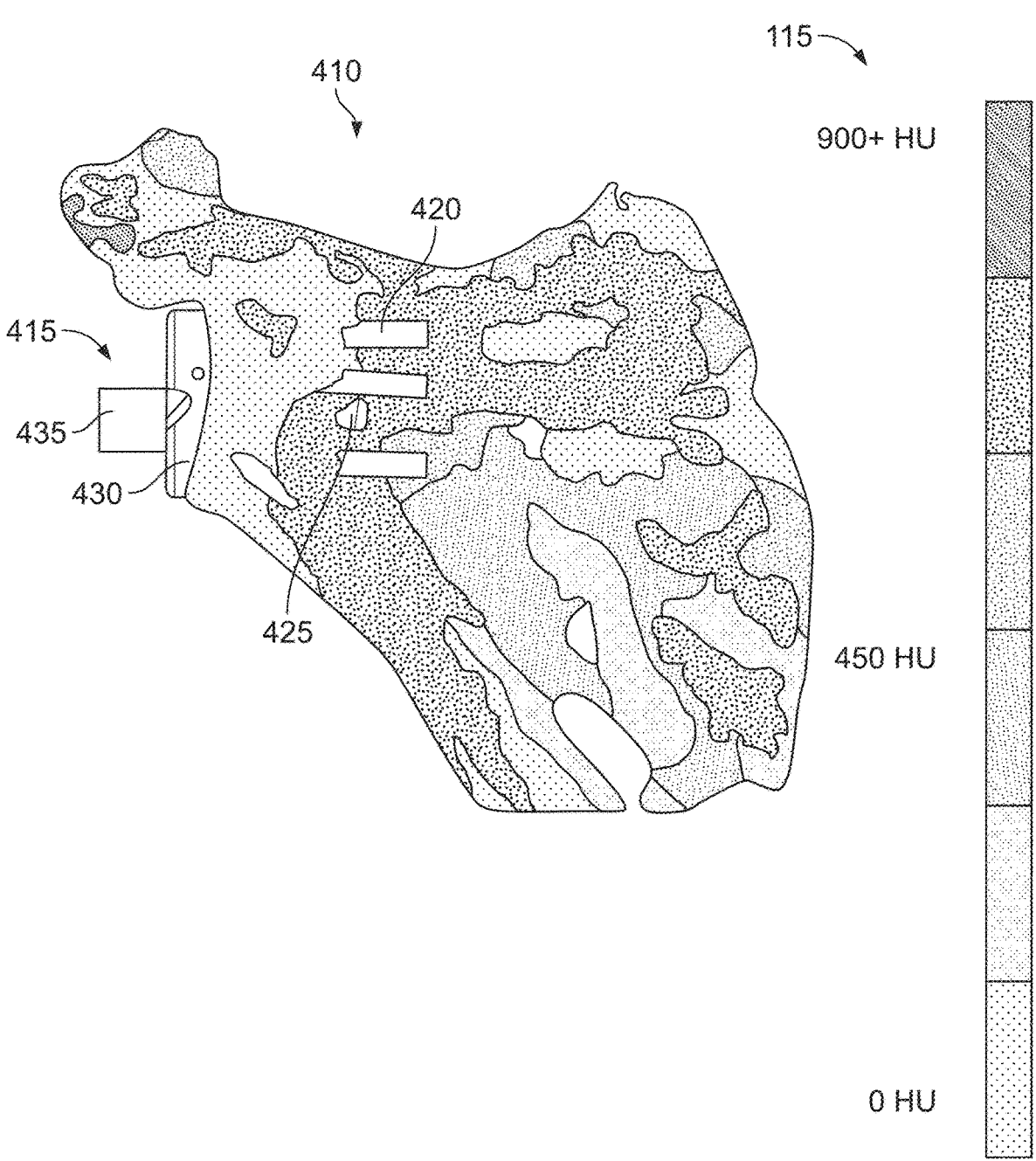

FIG. 4 illustrates an alternative embodiment of an enlarged back side perspective view 400 (FIG. 4A) of a colorized density-mapped scapula with a patient-specific device 415 installed, a front view of a colorized density-mapped scapula image 405 (FIG. 4B), an enlarged side view 410 (FIG. 4C) of the colorized density-mapped scapula image 405, and the colorized density classification scale 115 in HU. The patient-specific device 415 is similar to the patient-specific device 205 described in connection with FIG. 2. In the embodiment shown in FIG. 4, the screws 420 and/or fixation member 425 are of different lengths and angles as opposed to the device shown in FIG. 2 to take advantage of more dense regions of bone in this embodiment. The more dense regions of the bone are shown in red, compared to the less dense regions of bone, which are shown in green, with a variable range of specific density values associated with the color gradient shown in the colorized density classification scale 115. The patient-specific device 415 may include one or more surgical screws 420 and a fixation member 425, the head of which may form at least a portion of a baseplate 430. In some embodiments, the fixation member may be provided in the form of a central surgical post, screw, or similar. The patient-specific device 415 may also include an extrusion taper 435, designed to couple to a glenosphere (not shown).

Figure 5A:
FIG. 5 (including FIG. 5A, FIG. 5B, and FIG. 5C) is a perspective view of a scapula image and a processed image based on the same, according to one embodiment.
Figure 5B:
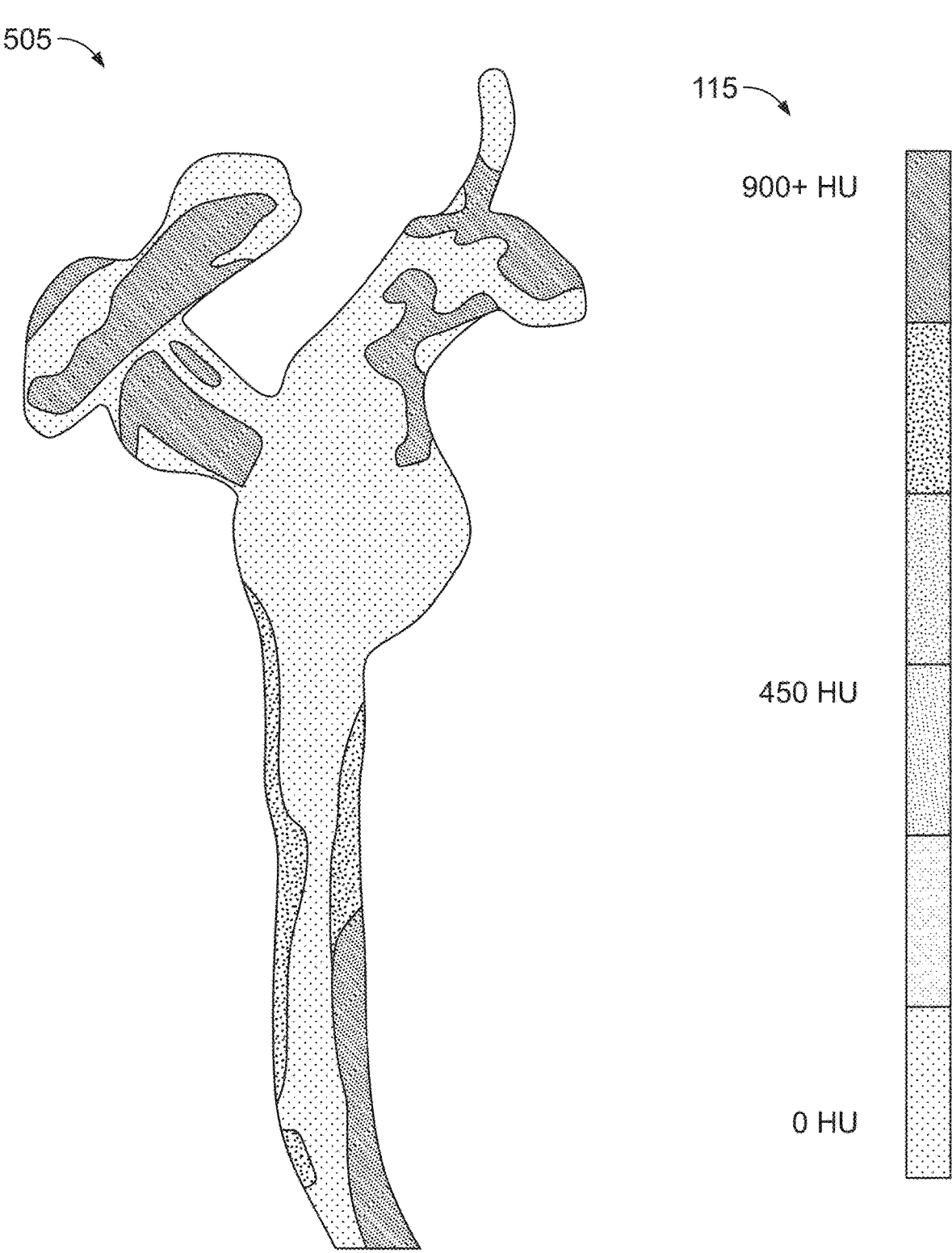
Figure 5C:
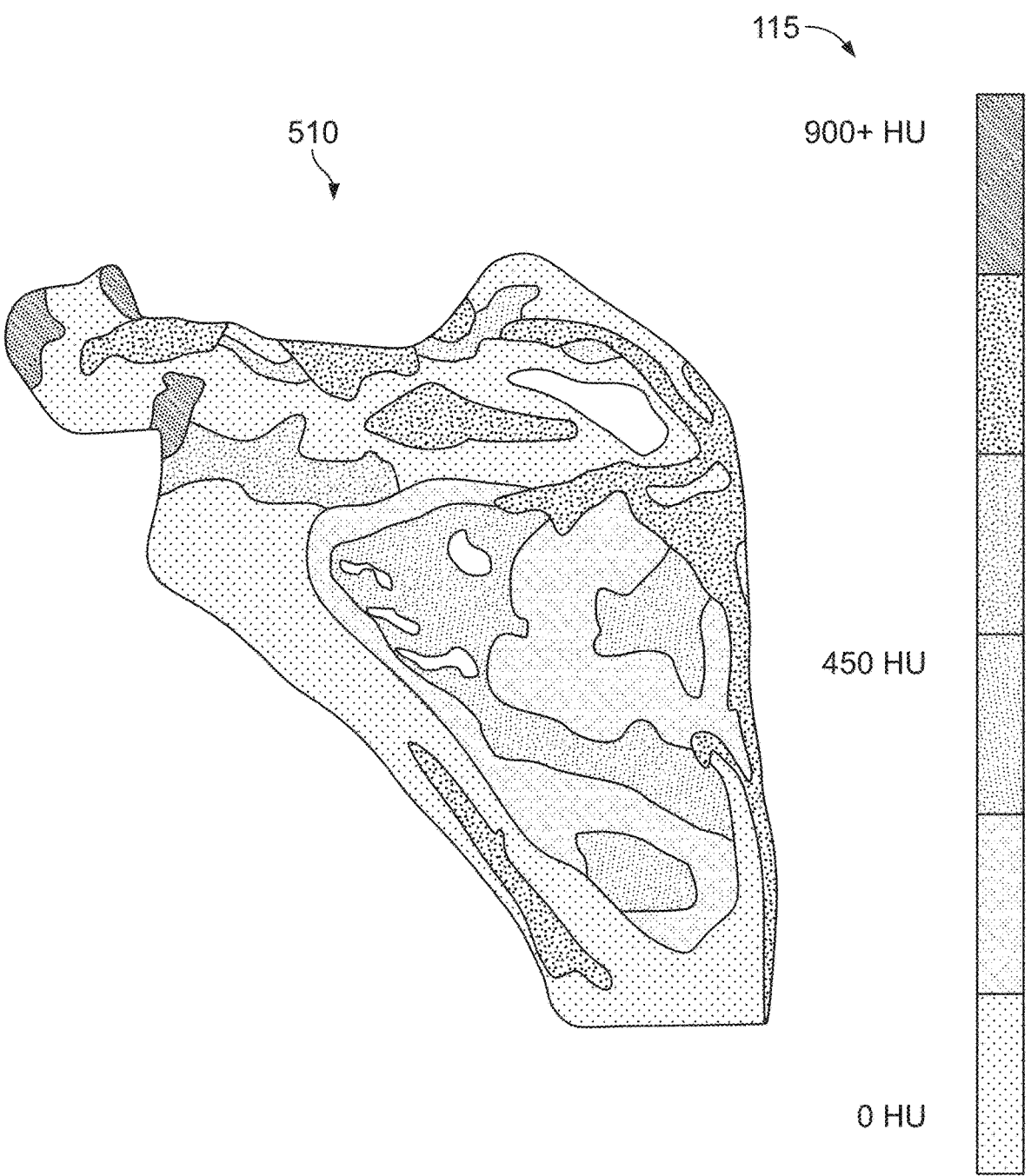

FIG. 5 illustrates an alternative embodiment of a grayscale scapula image 500 (FIG. 5A), an alternative embodiment of a front view of a colorized density-mapped scapula image 505 (FIG. 5B), an alternative embodiment of an enlarged back side perspective view 510 (FIG. 5C) of the colorized density-mapped scapula image 505, and the colorized density classification scale 115 in HU.

Figure 6A:
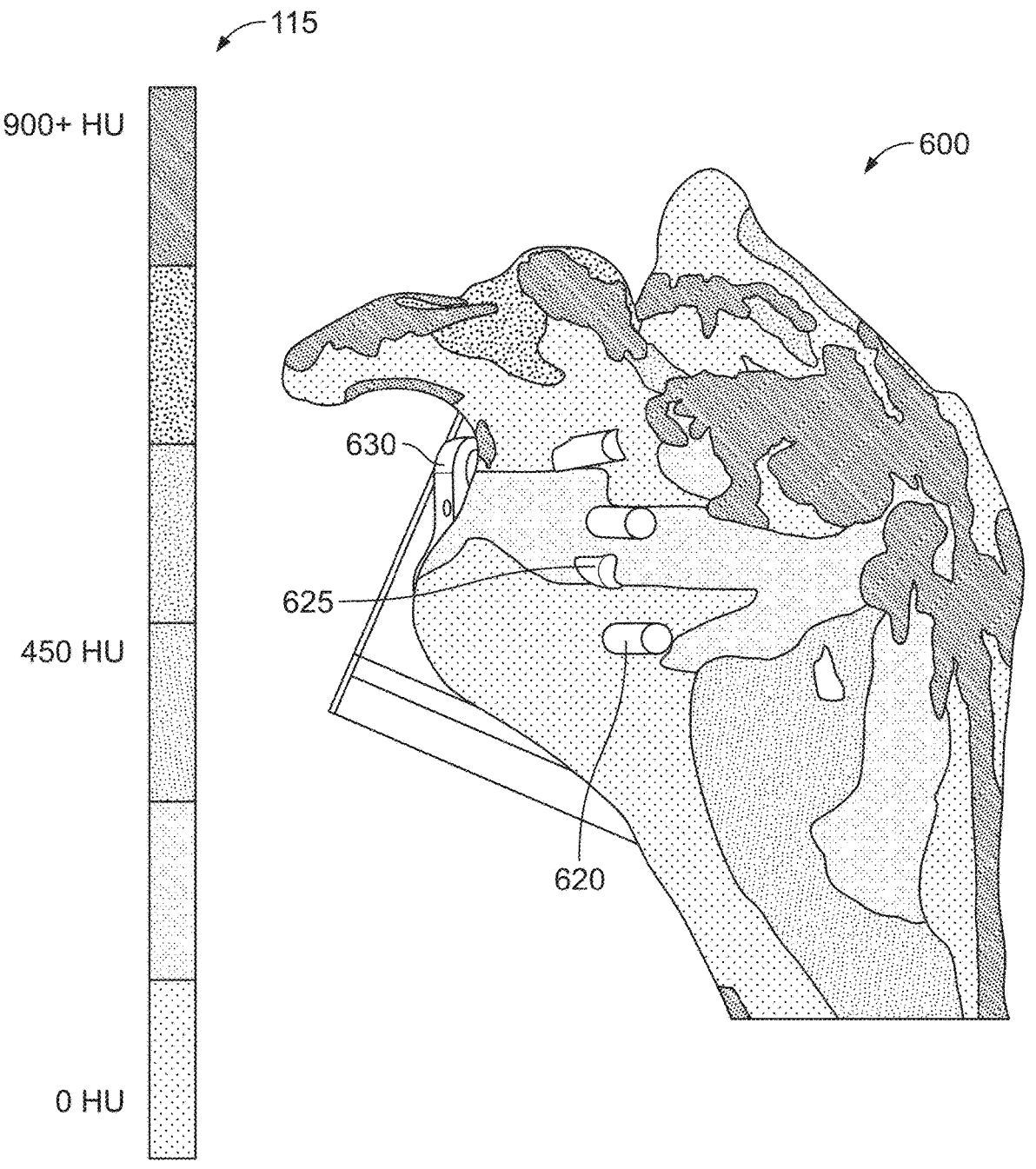
FIG. 6 (including FIG. 6A, FIG. 6B, and FIG. 6C) is a perspective view of a processed image of an implant installed in a patient's shoulder, according to one embodiment.
Figure 6B:
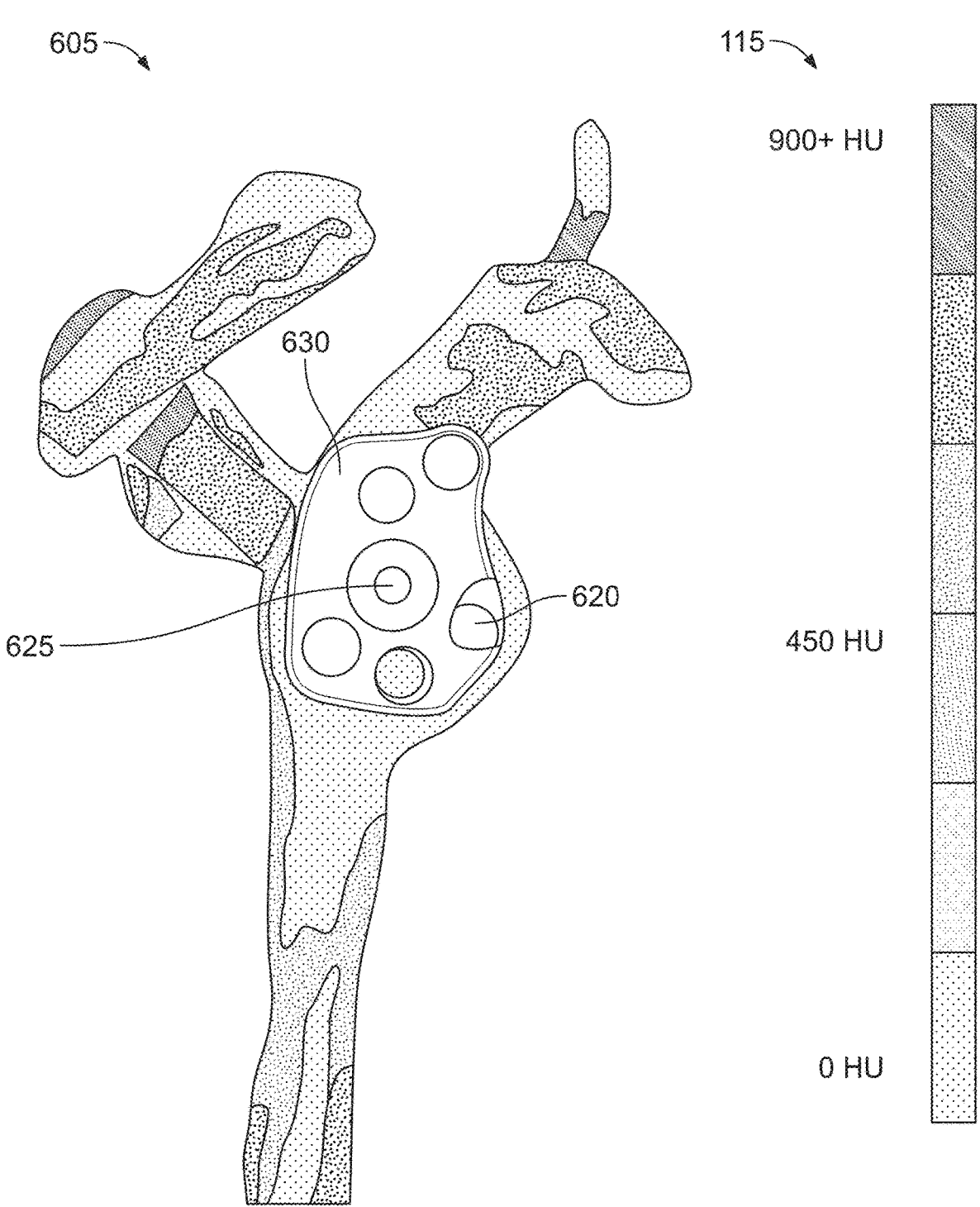
Figure 6C:
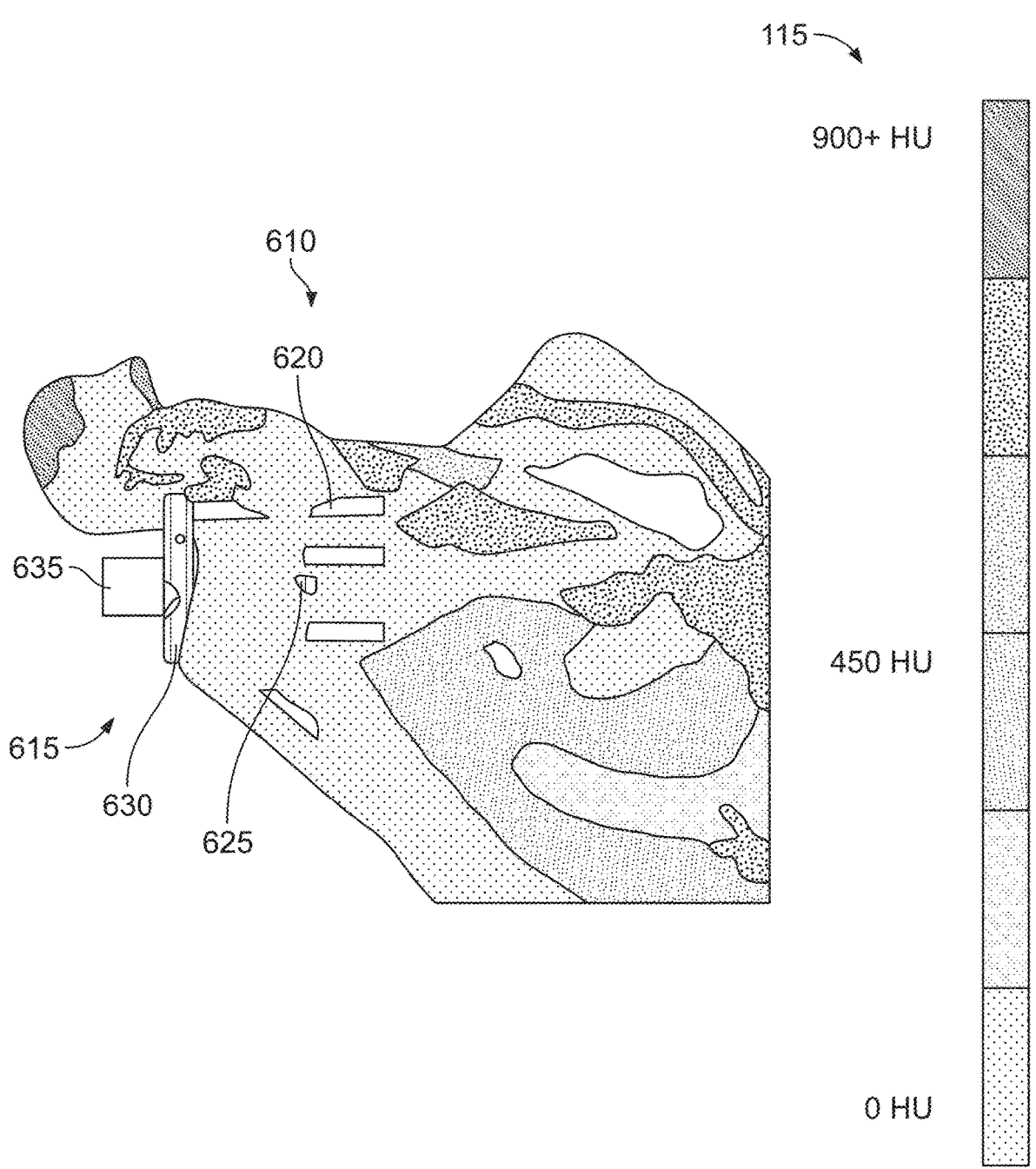

FIG. 6 illustrates an alternative embodiment of an enlarged back side perspective view 600 (FIG. 6A) of a colorized density-mapped scapula with a patient-specific device 615 installed, a front view of a colorized density-mapped scapula image 605 (FIG. 6B), an enlarged side view 610 (FIG. 6C) of the colorized density-mapped scapula image 605, and the colorized density classification scale 115 in HU. The patient-specific device 615 is similar to the patient-specific device 205 described in connection with FIG. 2. In the embodiment shown in FIG. 6, the screws 620 and/or fixation member 625 are of different lengths and angles as opposed to the device shown in FIGS. 2 and 4 based on the density regions of bone in this embodiment. The patient-specific device 615 may include one or more surgical screws 620 and a fixation member 625, the head of which may form at least a portion of a baseplate 630. In some embodiments, the fixation member 625 may be provided in the form of central surgical post, screw, or similar. The patient-specific device 615 may also include an extrusion taper 635, designed to couple to a glenosphere (not shown).

Figure 7A:
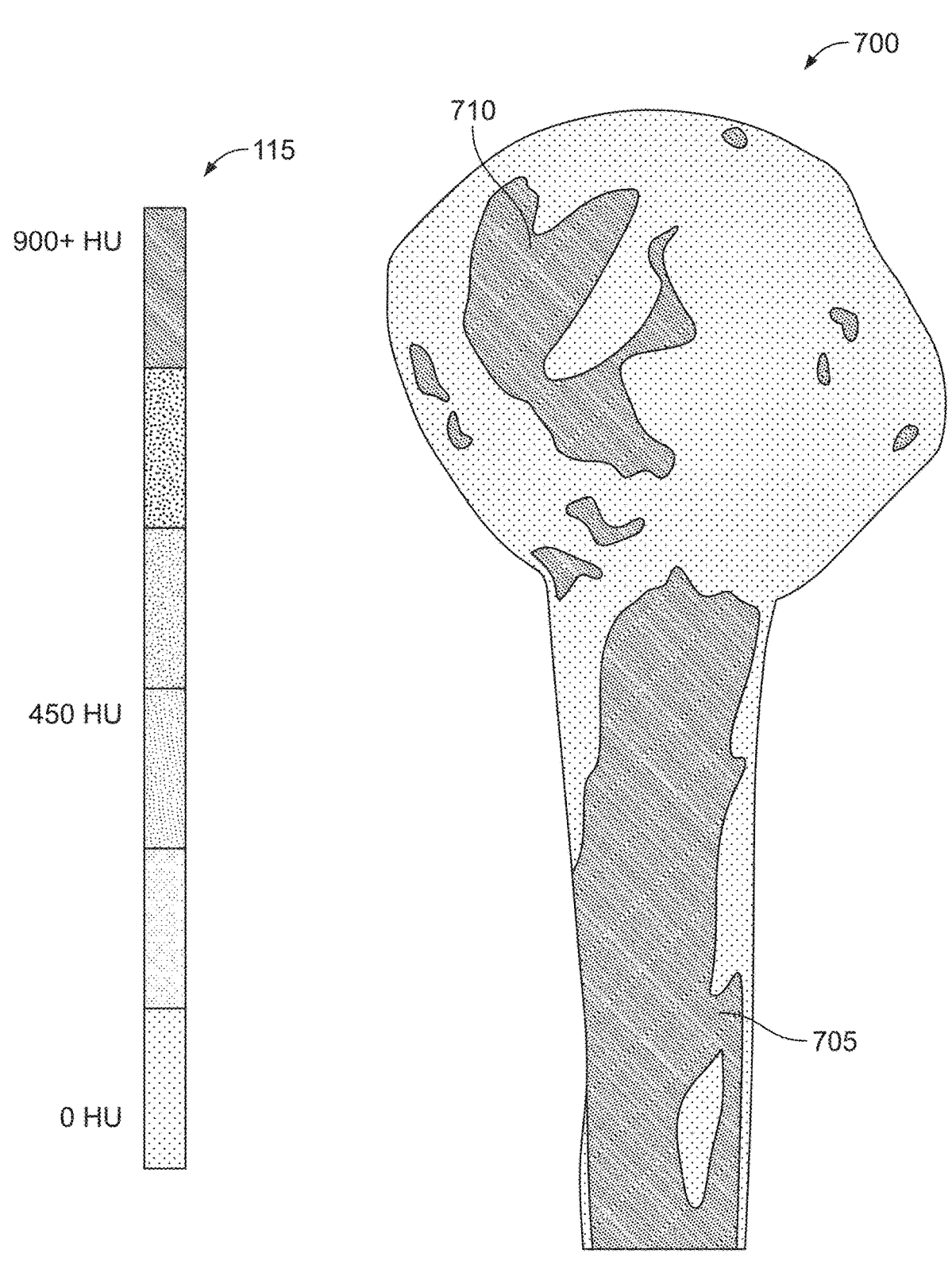
FIG. 7 (including FIG. 7A and FIG. 7B) is a perspective view of a processed humerus image, according to one embodiment.
Figure 7B:
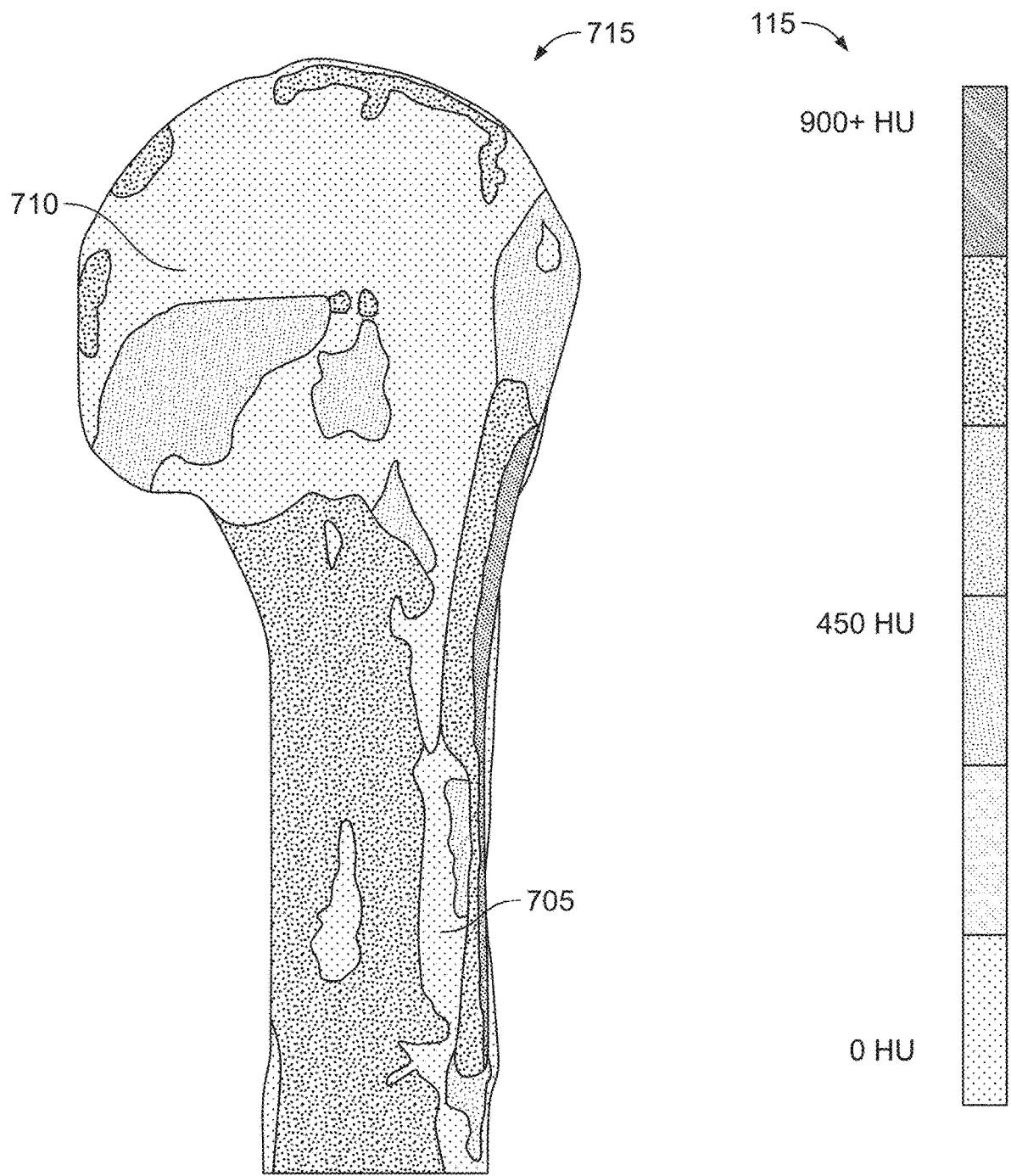

FIG. 7 illustrates a front view 700 (FIG. 7A) of a colorized density-mapped humerus 705 and humeral head 710, a side view 715 (FIG. 7B) of the colorized density-mapped humerus 705 and the humeral head 710, and the colorized density classification scale 115 in HU.

Figure 8A:
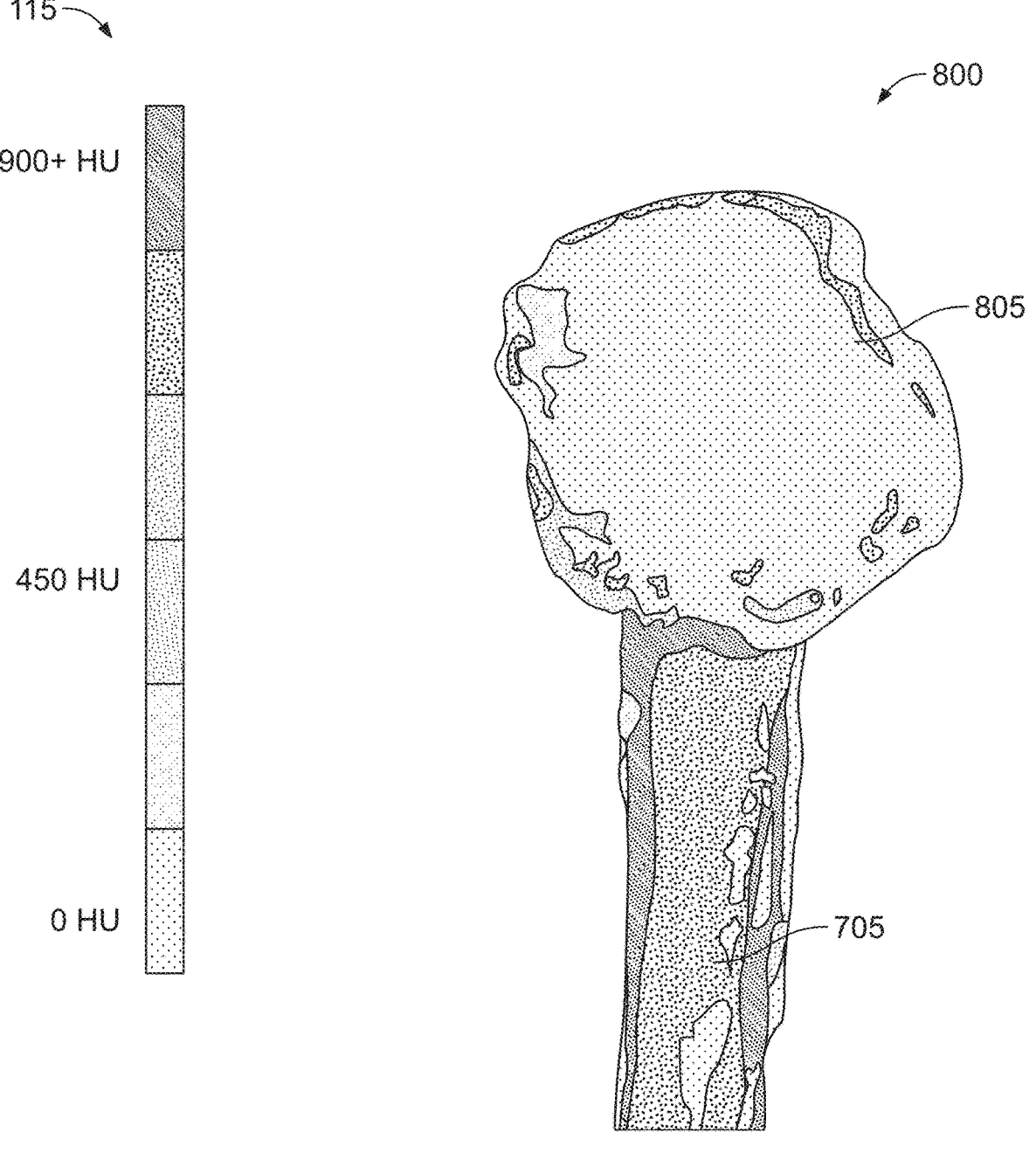
FIG. 8 (including FIG. 8A and FIG. 8B) is a perspective view of a processed cut humerus image, according to one embodiment.
Figure 8B:
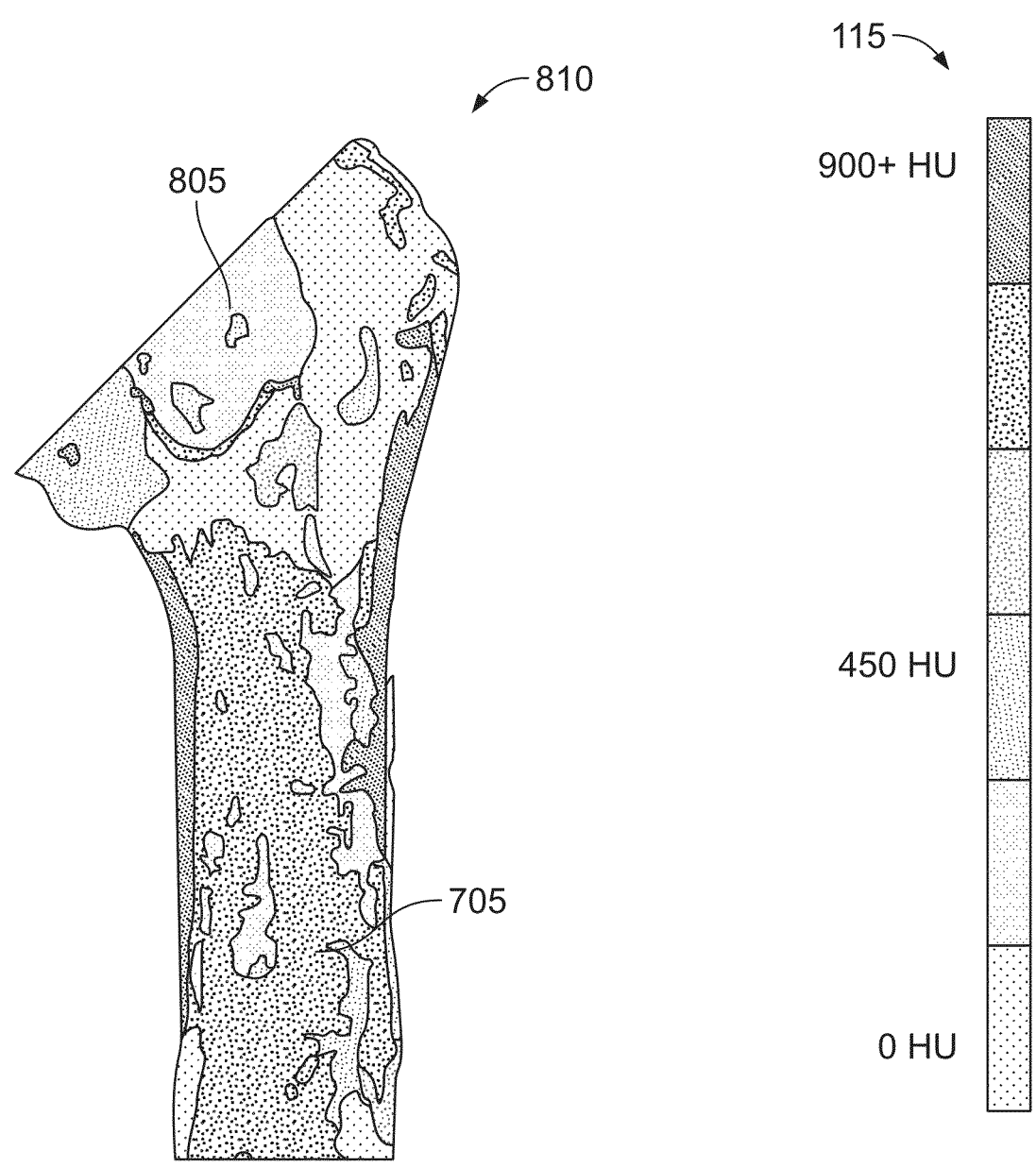

FIG. 8 illustrates a front view 800 (FIG. 8A) and a side view 810 (FIG. 8B) of the colorized density-mapped humerus 705 of FIG. 7 and a cut humeral head 805, where the humeral head 710 of FIG. 7 is sliced based, at least partially on, the density classification of one or more aspects of the humeral head 705. In some embodiments, the cut humeral head 805 may be sliced and/or otherwise prepared to be coupled to a portion of the patient-specific device 205, specifically a socket, and/or a glenosphere used for a traditional shoulder or RSA procedure, as described in more detail in connection with FIG. 2. In some embodiments, the systems and processes described herein can generate a recommended cut location, orientation, and/or angle based on the density classification as determined by the density-mapping process, as described in more detail in connection with FIG. 17.

Figure 9A:
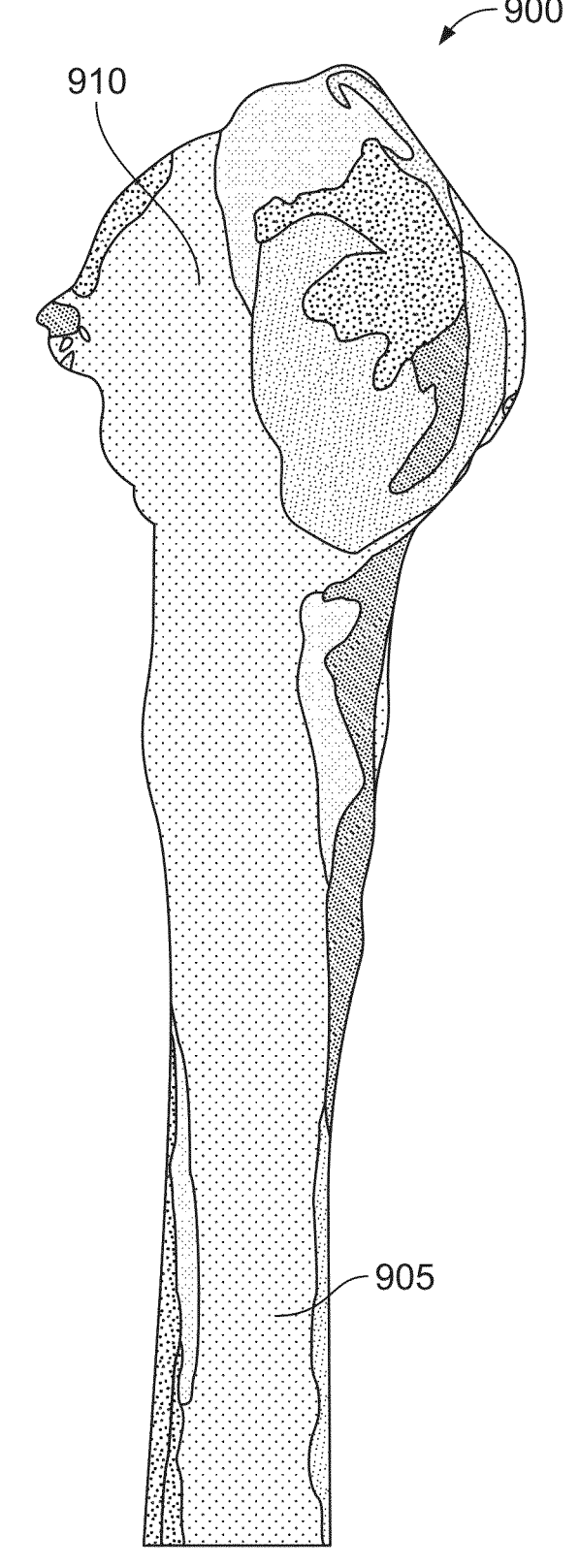
FIG. 9 (including FIG. 9A and FIG. 9B) is a perspective view of a processed humerus image, according to one embodiment.
Figure 9B:
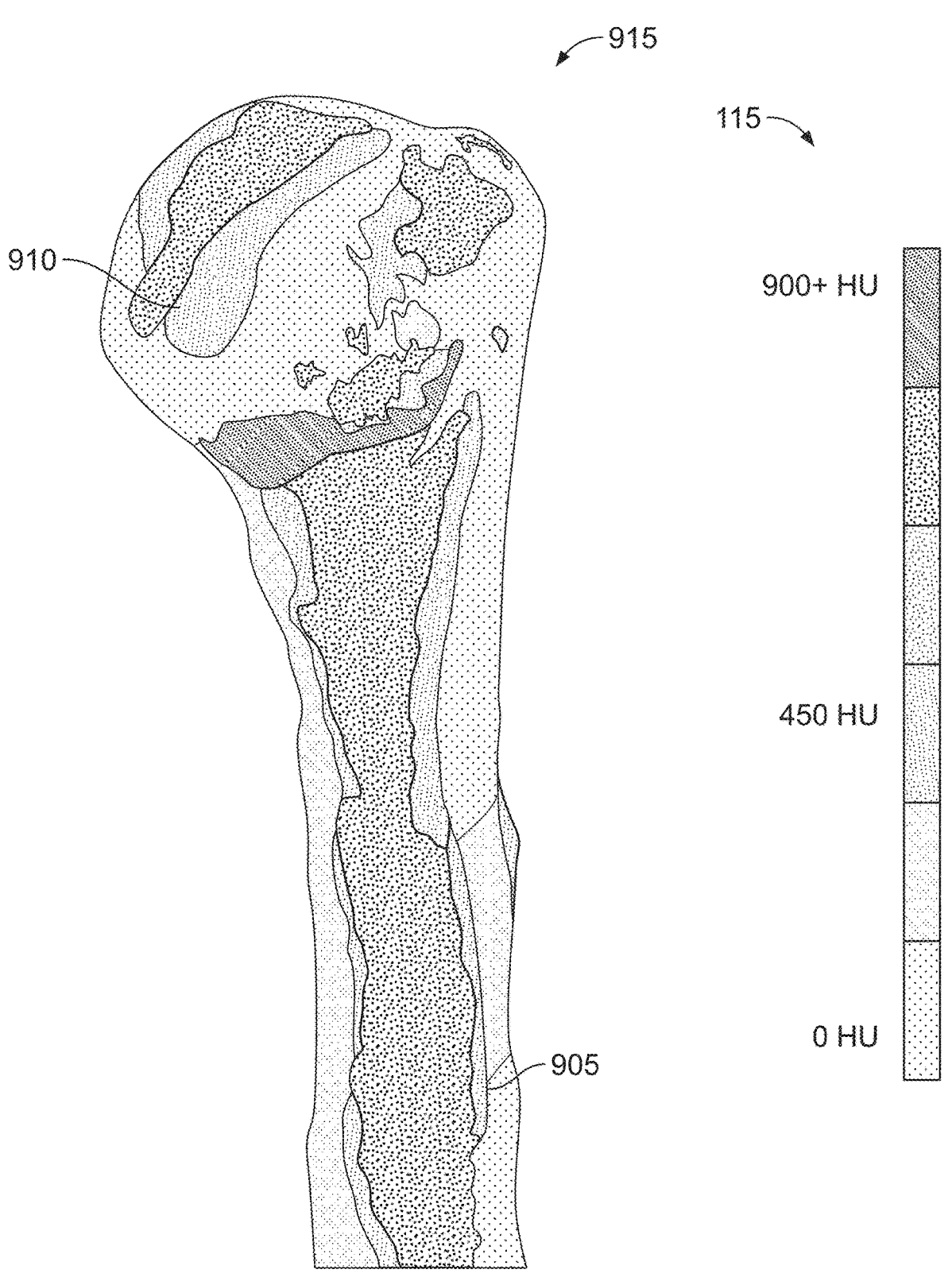

FIG. 9 illustrates an alternative embodiment of a front view 900 (FIG. 9A) of a colorized density-mapped humerus 905 and ball and joint socket joint 910, a side view 915 (FIG. 9B) of the colorized density-mapped humerus 905 and the ball and joint socket 910, and the colorized density classification scale 115 in HU.

Figure 10A:
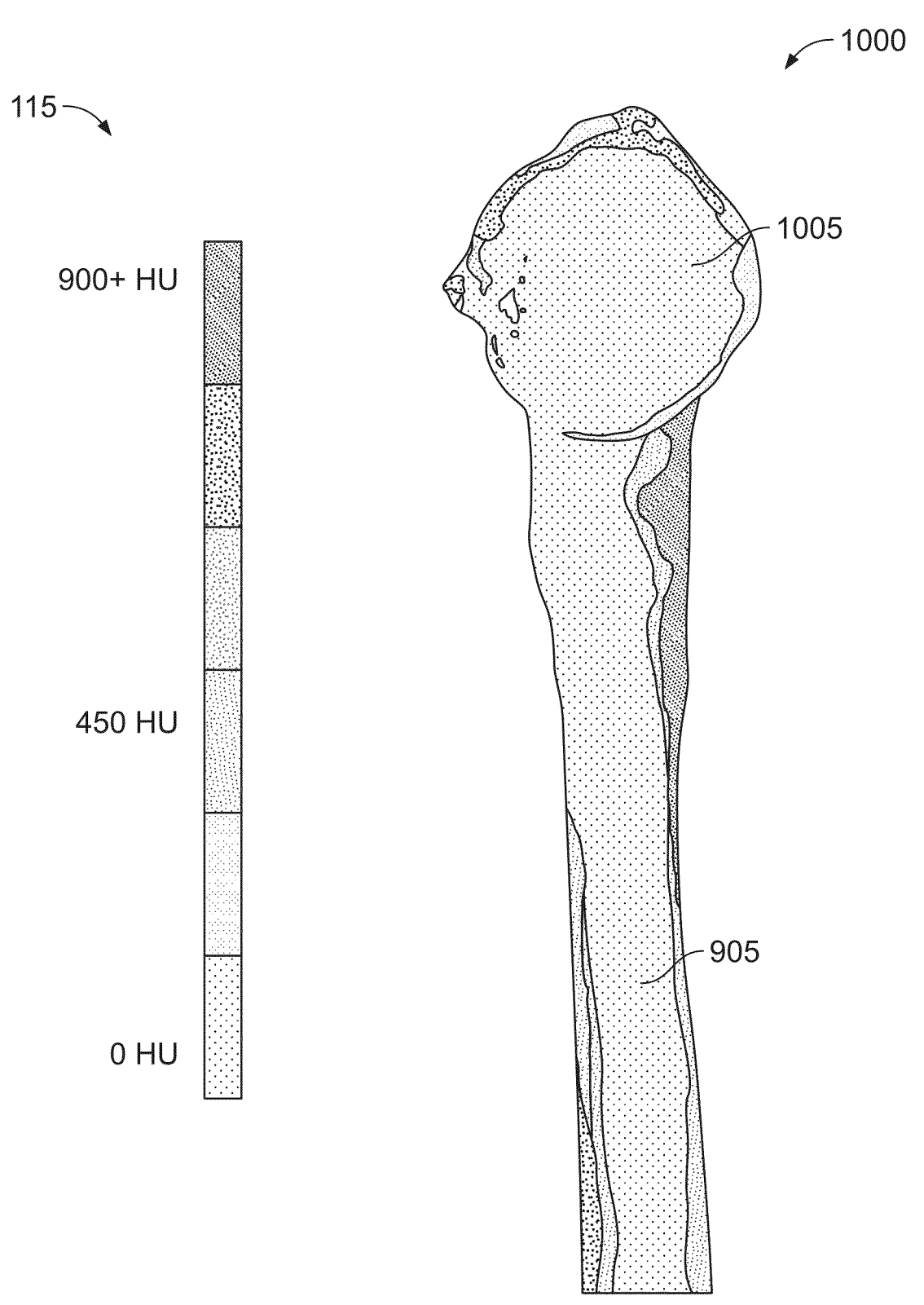
FIG. 10 (including FIG. 10A and FIG. 10B) is a perspective view of a processed cut humerus image, according to one embodiment.
Figure 10B:
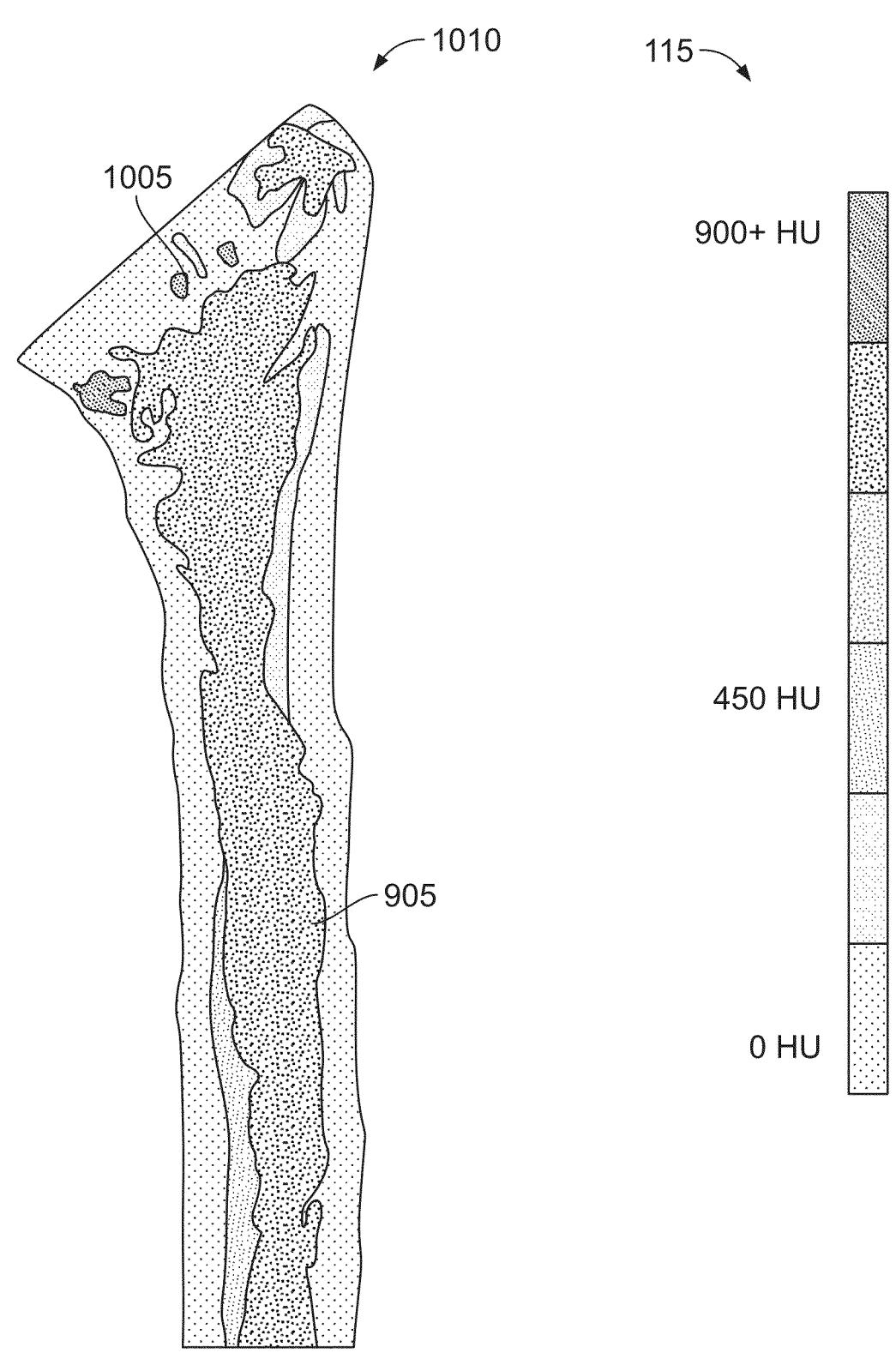

FIG. 10 illustrates a front view 1000 (FIG. 10A) and a side view 1010 (FIG. 10B) of the colorized density-mapped humerus 905 of FIG. 9 and a cut humeral head 1005, where the humeral head 910 of FIG. 9 is sliced based, at least partially on, the density classification of one or more aspects of the humeral head 905. In some embodiments, the cut humeral head 1005 may be sliced and/or otherwise prepared to be coupled to a portion of the patient-specific device 205, specifically the humeral stem, the socket, and/or the glenosphere used for an RSA procedure, as described in more detail in connection with FIG. 2. In some embodiments, the systems and processes described herein can generate a recommended cut location, orientation, and/or angle based on the density classification as determined by the density-mapping process, as described in more detail in connection with FIG. 17.

Figure 11A:
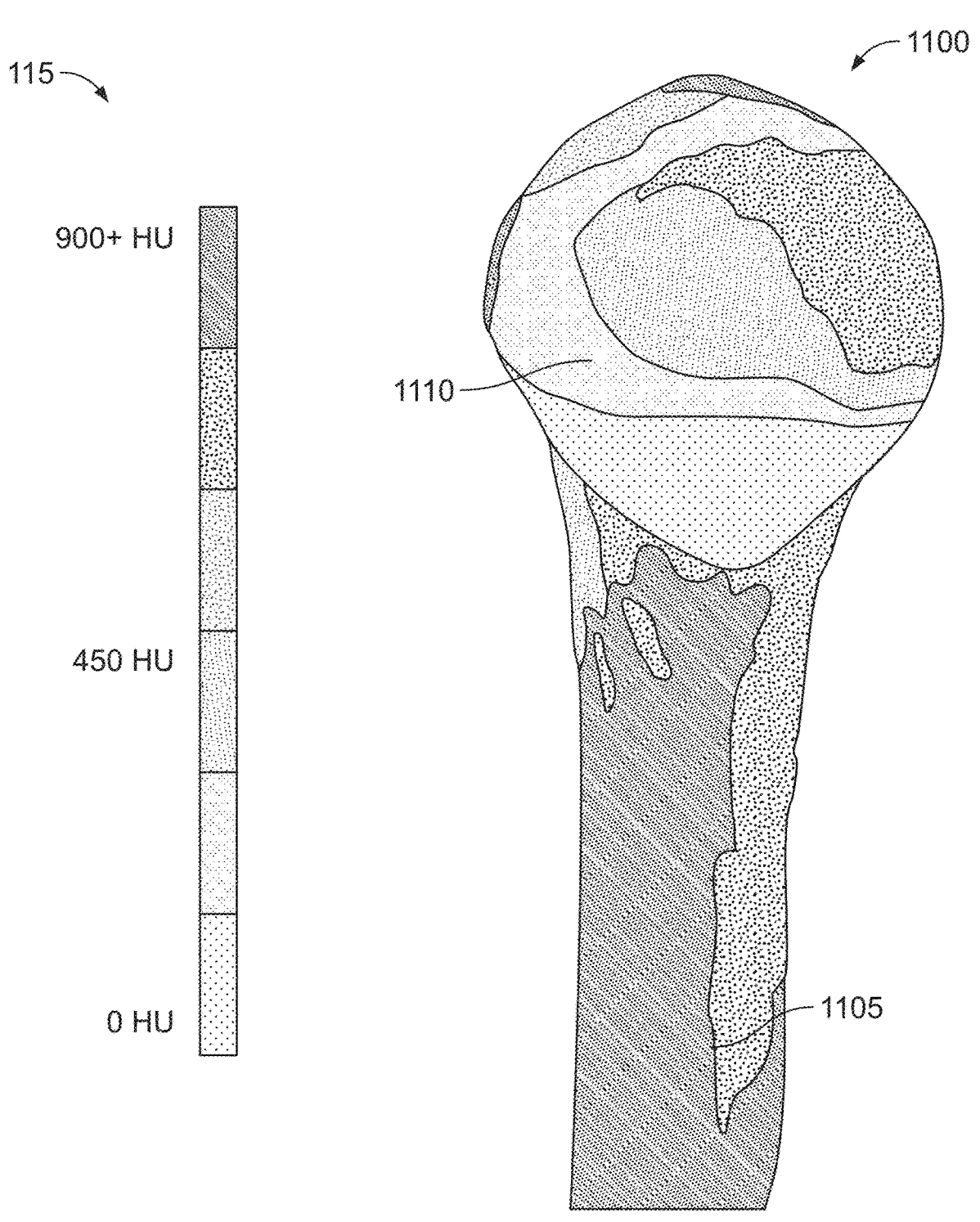
FIG. 11 (including FIG. 11A and FIG. 11B) is a perspective view of a processed humerus image, according to one embodiment.
Figure 11B:
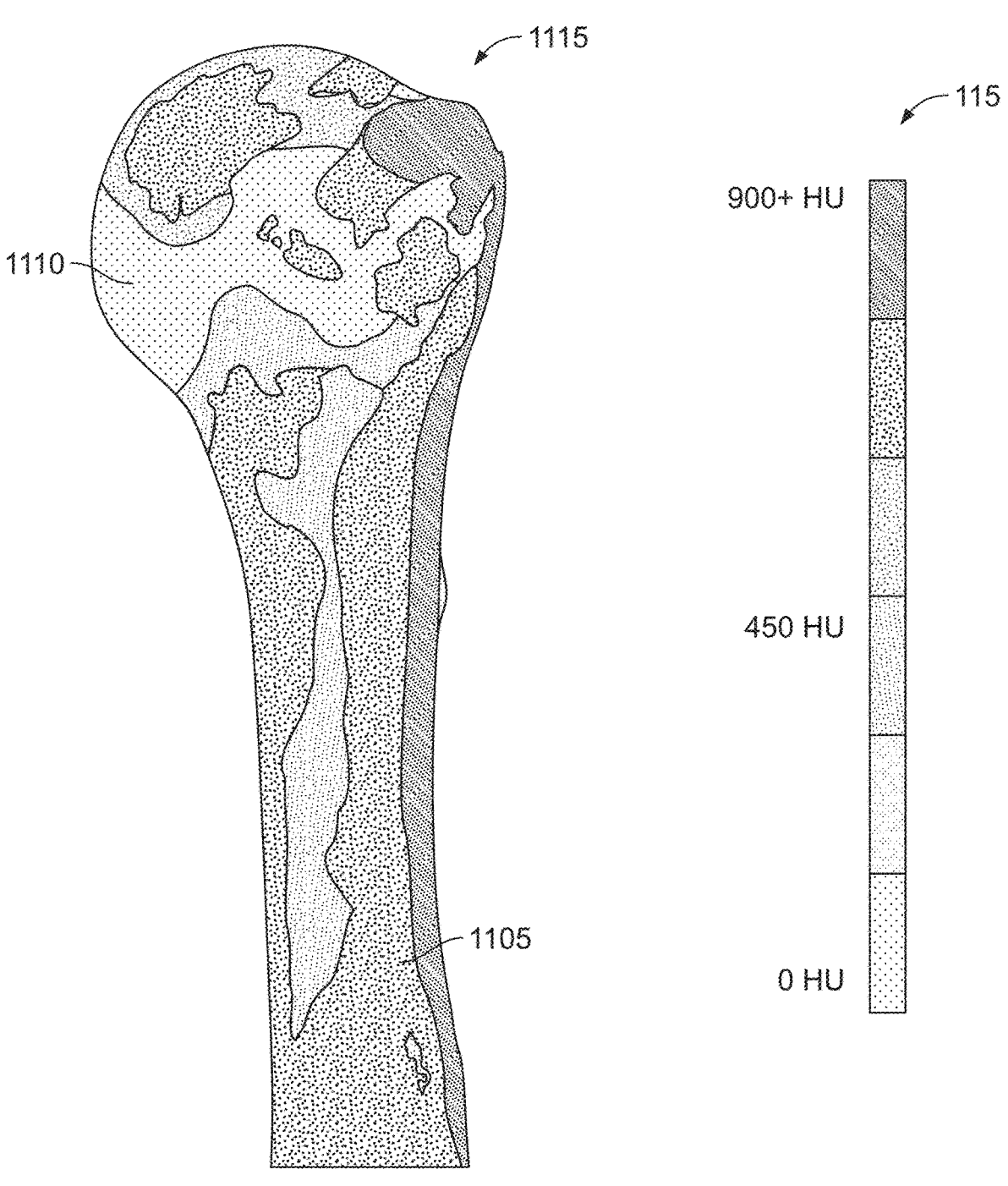

FIG. 11 illustrates an alternative embodiment of a front view 1100 (FIG. 11A) of a colorized density-mapped humerus 1105 and ball and joint socket joint 1110, a side view 1115 (FIG. 11B) of the colorized density-mapped humerus 1105 and the ball and joint socket 1110, and the colorized density classification scale 115 in HU.

Figure 12A:
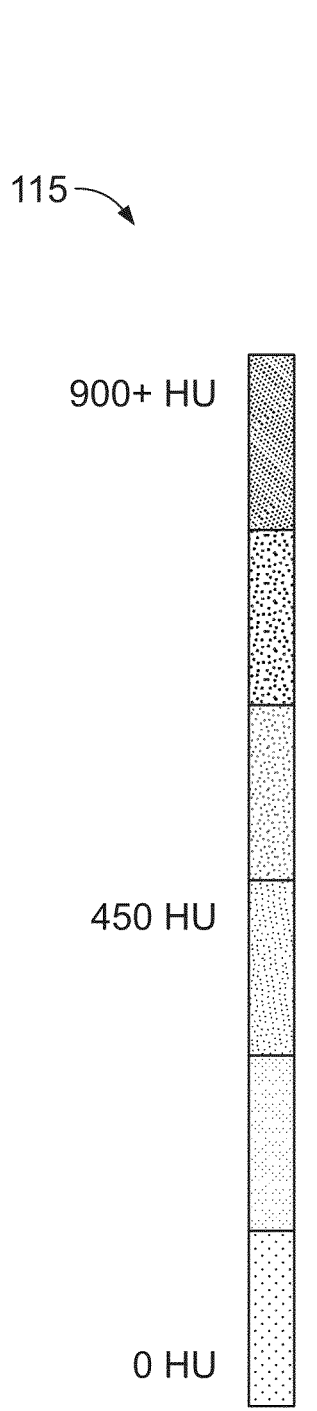
FIG. 12 (including FIG. 12A and FIG. 12B) is a perspective view of a processed cut humerus image, according to one embodiment.
Figure 12A:
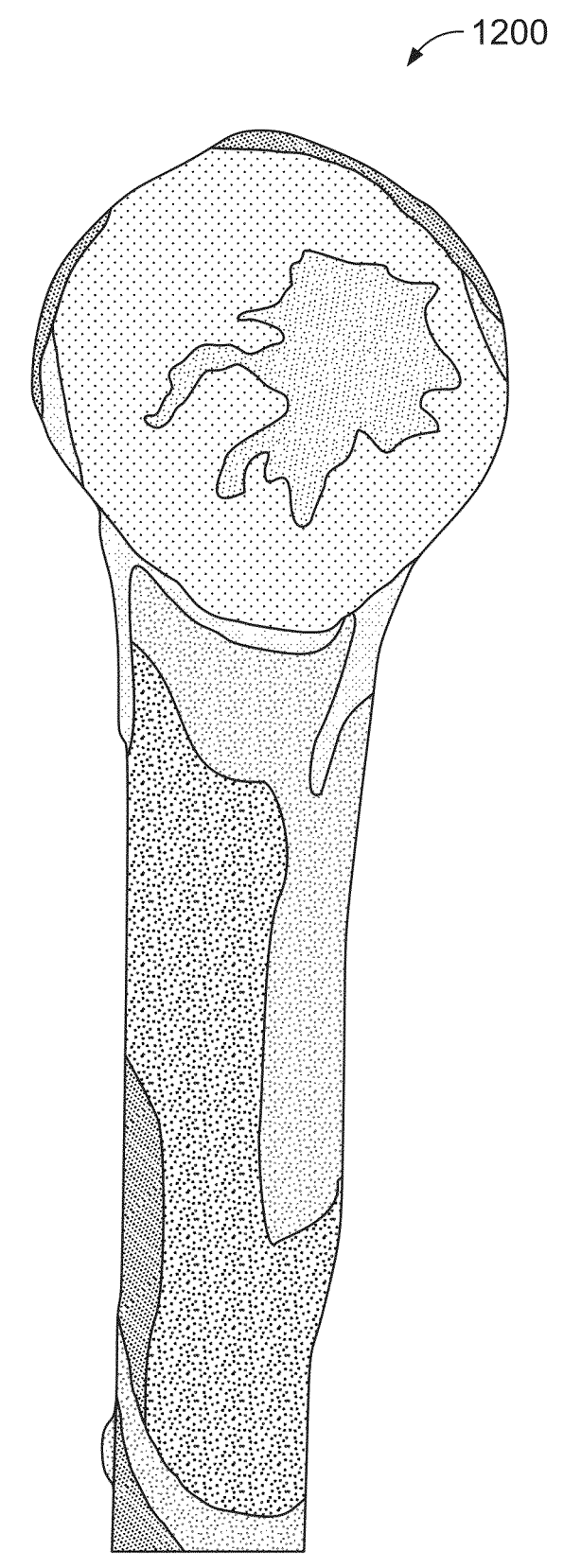
Figure 12B:
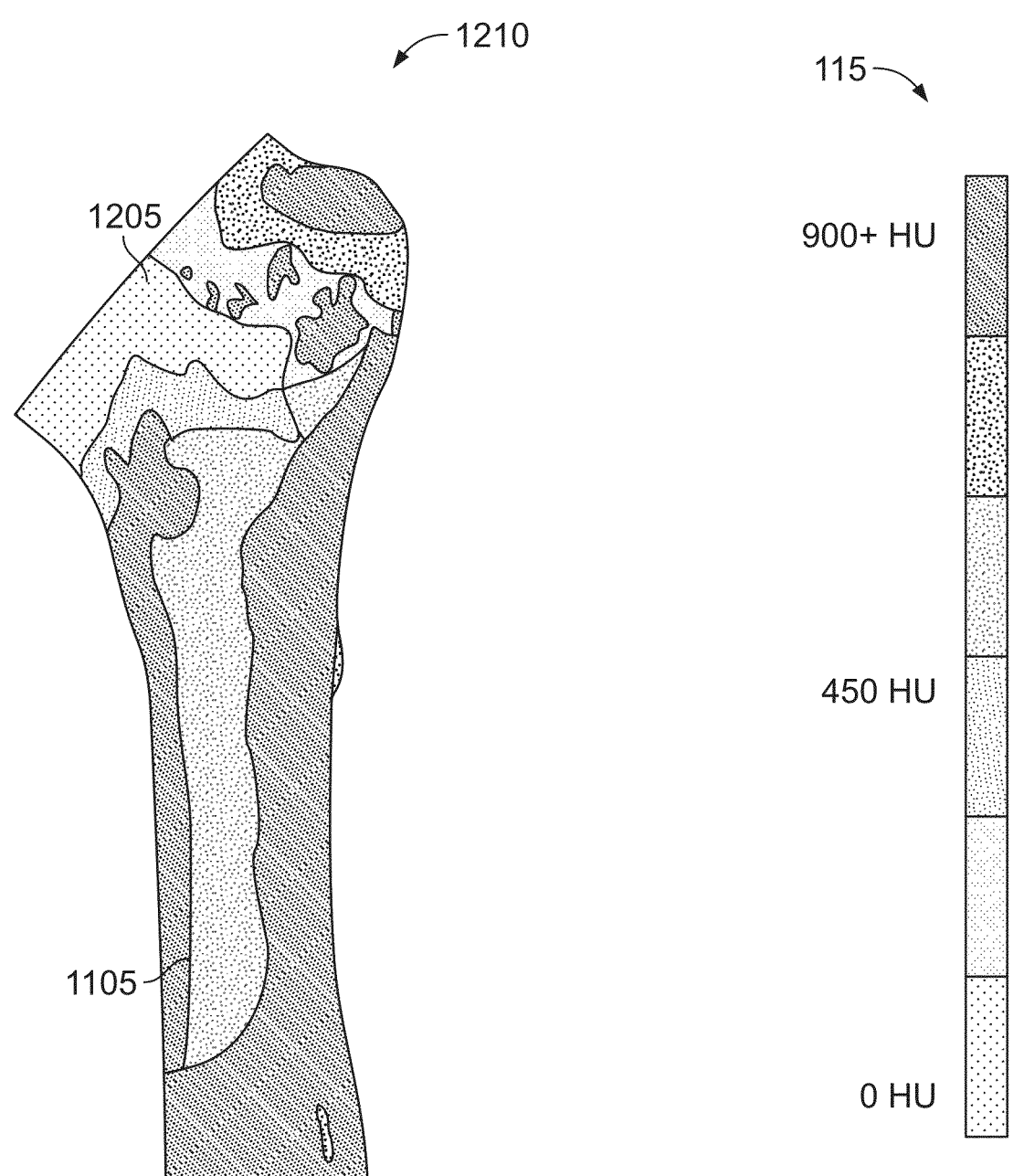
Figure 13A:
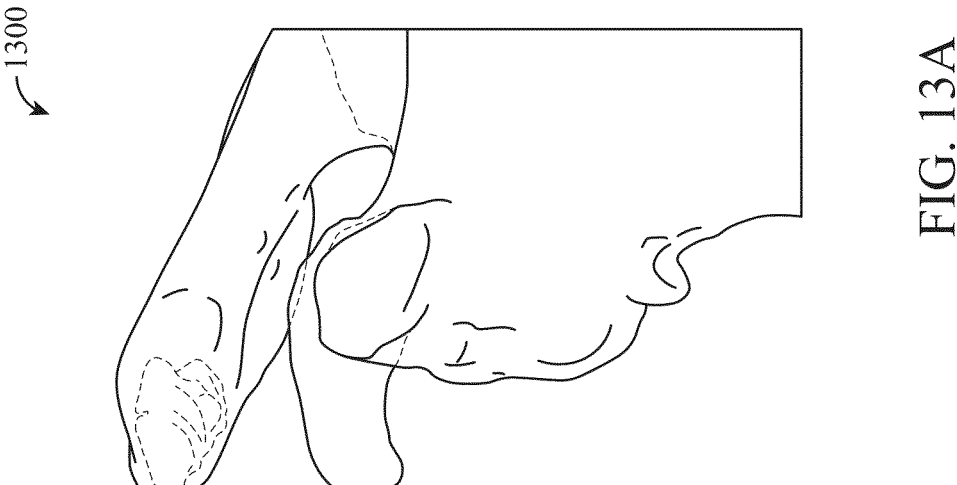
FIG. 13 (including FIG. 13A, FIG. 13B, FIG. 13C, and FIG. 13D) shows a perspective view of a category of a posterior defect and exemplary screw positions based on the same.
Figure 13B:
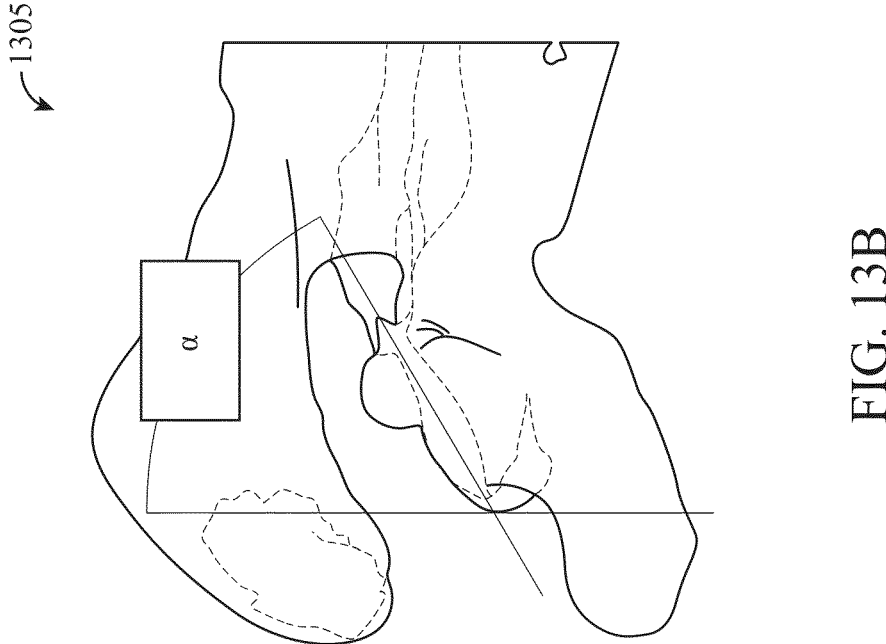
Figure 13C:
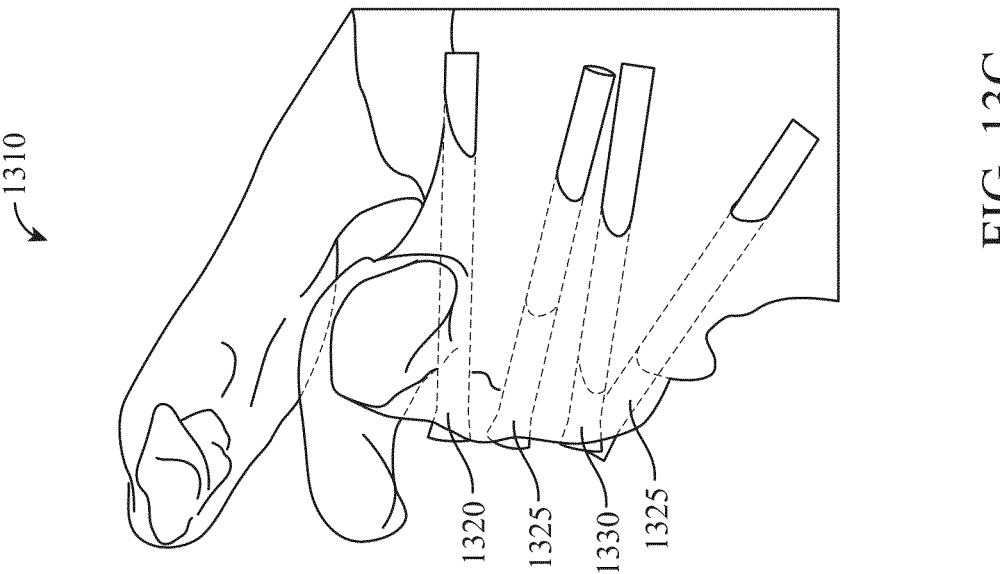
Figure 13D:
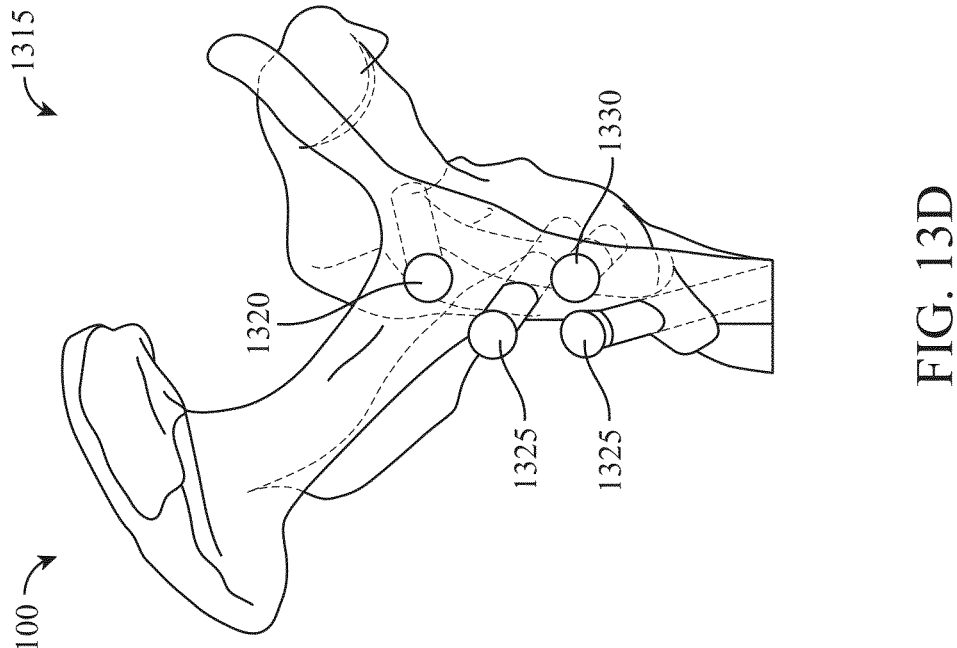

FIG. 12 illustrates a front view 1200 (FIG. 12A) and a side view 1210 (FIG. 12B) of the colorized density-mapped humerus 1105 of FIG. 11 and a cut humeral head 1205, where the humeral head 1110 of FIG. 11 is sliced based, at least partially on, the density classification of one or more aspects of the humeral head 1105. In some embodiments, the cut humeral head 1205 may be sliced and/or otherwise prepared to be coupled to a portion of the patient-specific device 205, specifically the humeral stem, the socket, and/or the glenosphere used for an RSA procedure, as described in more detail in connection with FIG. 2. In some embodiments, the systems and processes described herein can generate a recommended cut location, orientation, and/or angle based on the density classification as determined by the density-mapping process, as described in more detail in connection with FIG. 17.

FIG. 13 illustrates a non-limiting shoulder-specific exemplary embodiment of the deformity classification and density mapping processes described in more detail in connection with FIGS. 16 and 17. In particular, a patient-specific grayscale image of an anatomical feature can be processed by the deformity classification process via an artificial intelligence model to identify and classify a deformity associated with the anatomical feature. In some embodiments, the system can transform the patient-specific grayscale image into a 3D digital representation of the anatomical feature using a non-rigid shape reference, as described in more detail in connection with FIG. 16. The deformity classification process can identify that there is a defect with the glenoid and classify the defect according to one or more attributes. For example, version and tilt are exemplary measurements used in orthopedic and radiologic evaluations of the glenoid (i.e., the socket portion of the scapula). The glenoid articulates with the humeral head to form the shoulder joint. The version and tilt measurements may assist in identifying deformities that may be classified as, for example, minimal planar, superior, anterior, posterior, and skinny. The glenoid version refers to an angular orientation of a glenoid articular surface relative to a reference plane, which is typically a scapular plane or a perpendicular axis through the scapula. In some embodiments, the version measurement can refer to a distance between a center of the glenoid (GC) and a coracoid-acromion average (CA Plane) value between an edge of an acromion and an edge of a coracoid. The glenoid tilt measurement refers to an inclination of the glenoid articular surface in a superior-inferior direction. A superior tilt occurs when the glenoid articular surface tilts upward and an inferior tilt occurs when the glenoid articular surface tilts downward. The coracoid-acromion (CA) placement is a measurement of the medial or linear amount of glenoid deformity.

FIG. 13 illustrates a front side perspective view 1300 (FIG. 13A), a top perspective view 1305 (FIG. 13B) of a glenoid with a posterior deformity, an alternative back side perspective view 1310 (FIG. 13C) and an alternative lateral side perspective view 1315 of the glenoid with a posterior deformity with a patient-specific screw configuration installed. Specifically, FIG. 13 illustrates a mega posterior deformity, identified as a posterior deformity and further characterized as a mega posterior deformity via the deformity classification process when a version measurement associated with the shoulder is greater than a tilt measurement associated with the shoulder, and the version measurement is less than −45°. The illustrative example shown in FIG. 13B is for a glenoid with a version measurement a of −60°. The screw placement illustrated in FIGS. 13C and 13D include screw placements based on both the deformity classification, and a density mapping classification of the patient's anatomy. For example, the screw placement includes an index screw 1320 which can be an anterior inferior placed screw or placed at a base of the coracoid, depending on the patient-specific anatomical features or attributes thereof. In some embodiments, the index screw 1320 is used to determine a baseline for a baseplate thickness, where the baseplate is a portion of a patient-specific device, in some embodiments. The screw configuration further includes two other screws 1325 configured in connection with the baseplate surface located at an edge of the glenoid (EOG). In this non-limiting embodiment, the two other screws 1325 are defined by an anterior tubercle. There is also a PLL screw 1330 which is the most anterior screw and is likely an anterior inferior screw. In some embodiments, the PLL screw that is parallel to a trajectory of the central post of the patient-specific device. It will be appreciated that although only the screw configuration is shown in FIG. 13, that the patient-specific device configuration can further include a baseplate with a fixation member, screw holes, and an extrusion taper. It will further be understood, the examples herein are for illustrative purposes only and many different deformity classifications and many different screw placements and implant designs are contemplated, including deformity classifications, screw or other fixation placements, and implant designs associated with non-shoulder anatomy.

Figure 14A:
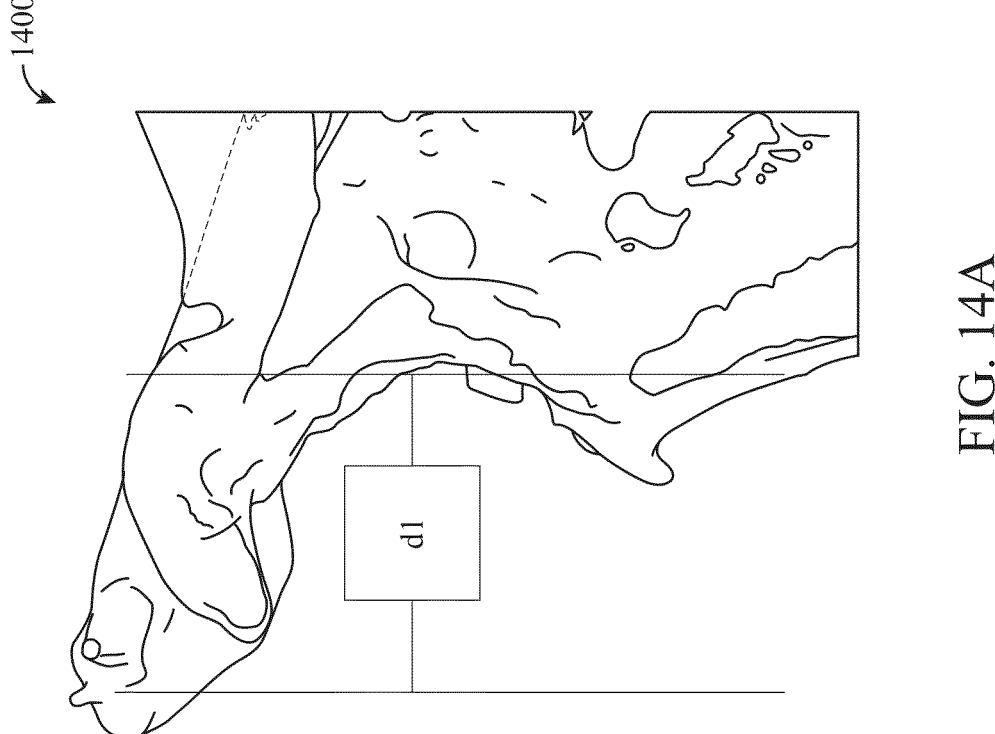
FIG. 14 (including FIG. 14A, FIG. 14B, and FIG. 14C) shows a perspective view of a category of a minimal planar defect and exemplary screw positions based on the same.
Figure 14B:
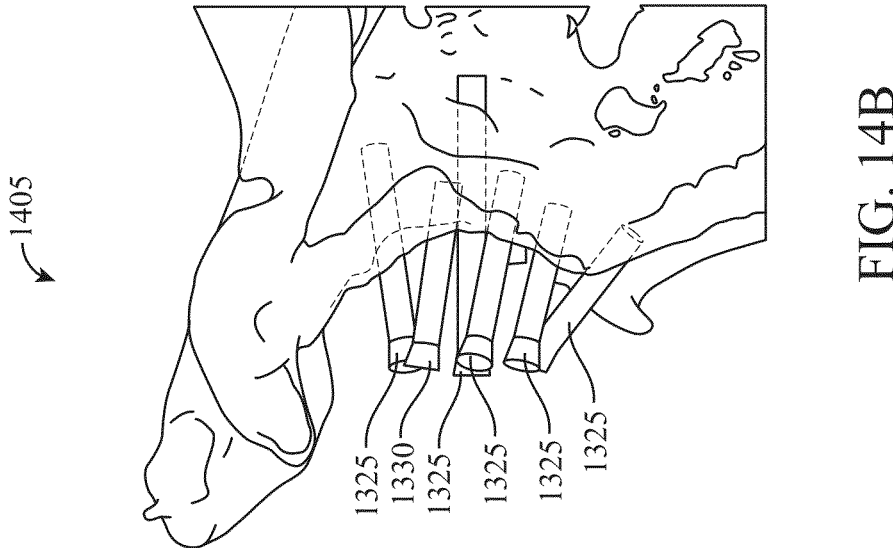
Figure 14C:
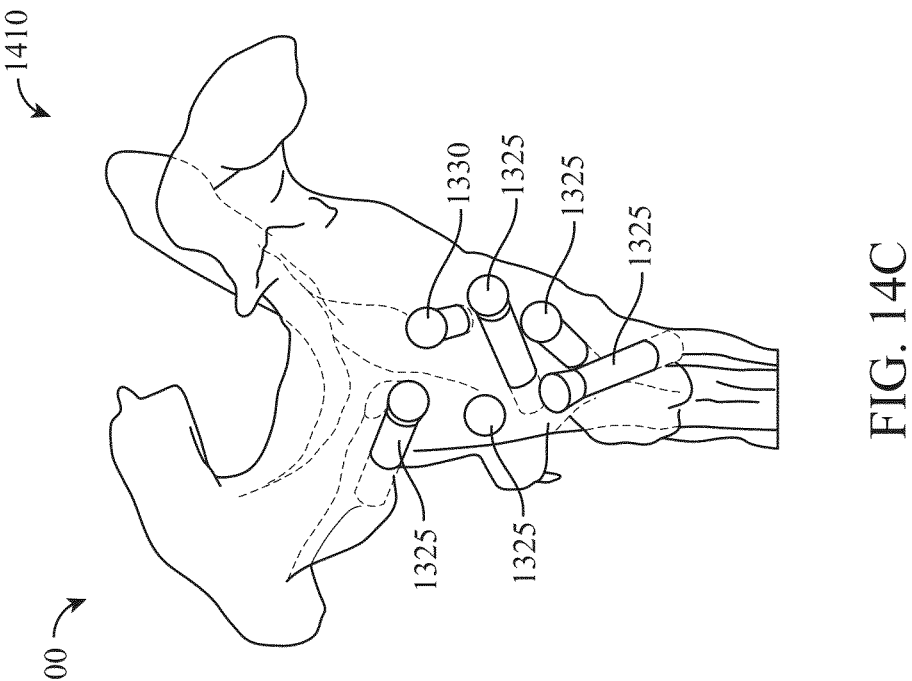

FIG. 14 illustrates a front side perspective view 1400 (FIG. 14A) of a glenoid with a minimal planar deformity, a back side perspective view 1405 (FIG. 14B) and a lateral side perspective view 1410 of the glenoid with the minimal planar deformity with a patient-specific screw configuration installed. Specifically, FIG. 14 illustrates a medialized minimal planar deformity, identified as a minimal planar deformity and further characterized as a medialized minimal planar deformity via the deformity classification process when a version measurement associated with the glenoid is less than 15°. A medialized minimal planar deformity is classified as a minimal planar deformity where the distance d1 between the CA Plane and the GC is greater than 30. The illustrative example shown in FIG. 14A is for a glenoid with a d1 of 48 for the measurement from the CA Plane to the GC. The screw placement illustrated in FIGS. 14B and 14C include screw placements based on both the deformity classification, and a density mapping classification of the patient's anatomy. For example, the screw placement includes five other screws 1325, configured such that the EOG plane (i.e., the surface of the baseplate) lies at a base of the coracoid/projected arch. There is a PLL screw 1330 which is a superior screw and is provided in the form of a coracoid or acromion/spine screw. It will be appreciated that although only the screw configuration is shown in FIG. 14, that the patient-specific device configuration can further include a baseplate with a fixation member, screw holes, and an extrusion taper. There are particular difficulties associated with designing, manufacturing, and installing patient-specific devices for a medialized minimal planar deformity because the patient's anatomy typically warrants a thicker baseplate to provide additional footprint for the screw trajectories, however the thickness of the baseplate to create a moment arm for the screw fixation is balanced with restoring a lateralization of the original glenoid cavity to mitigate wear and tear to the extent possible.

Figure 15A:
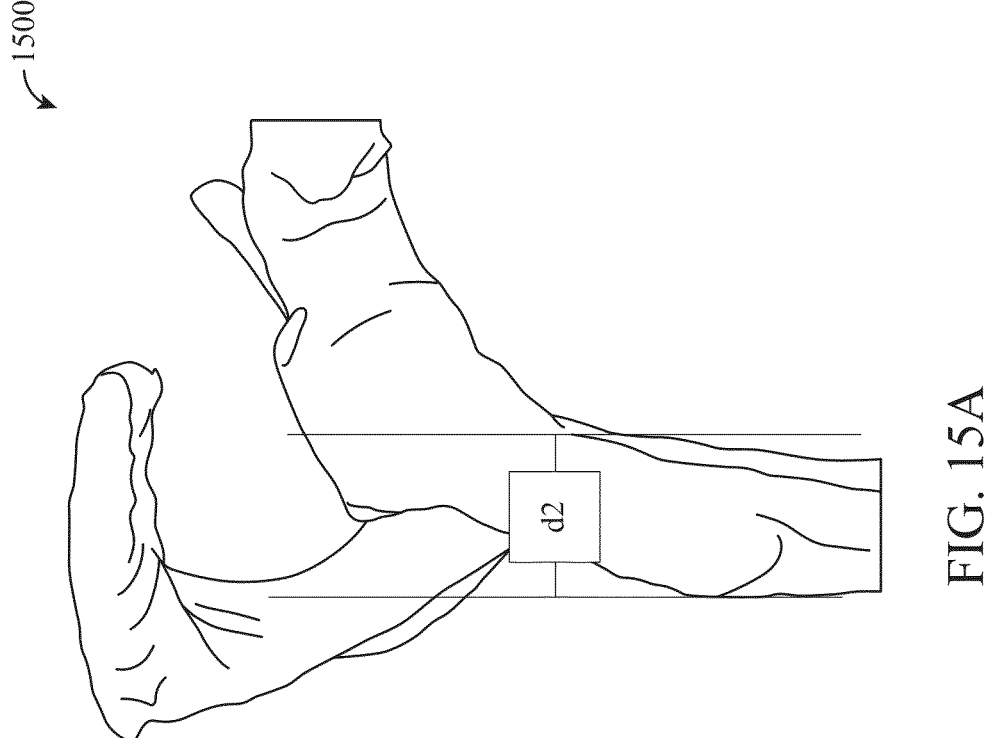
FIG. 15 (including FIG. 15A, FIG. 15B, and FIG. 15C) shows a perspective view of a category of a skinny type and exemplary screw positions based on the same.
Figure 15B:
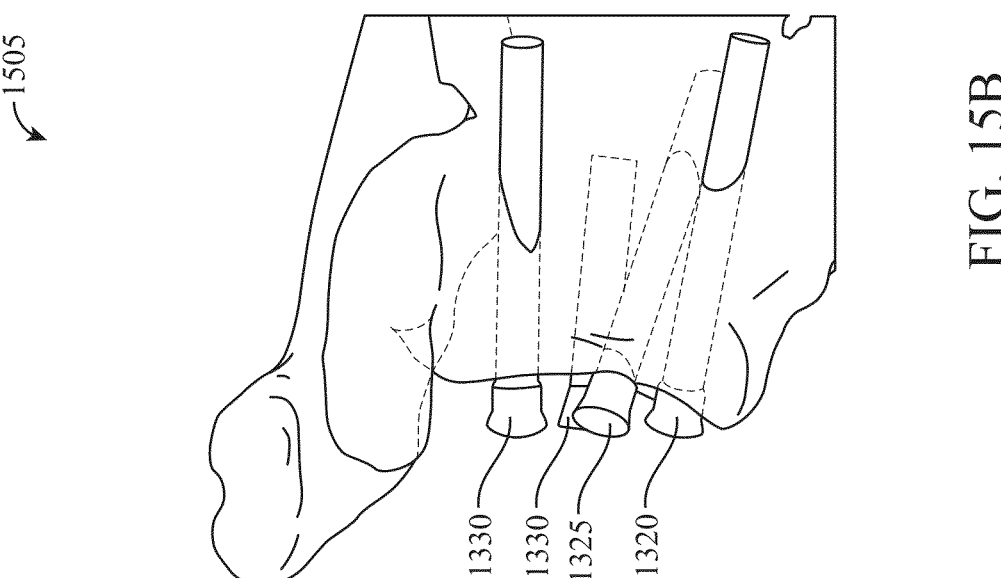
Figure 15C:
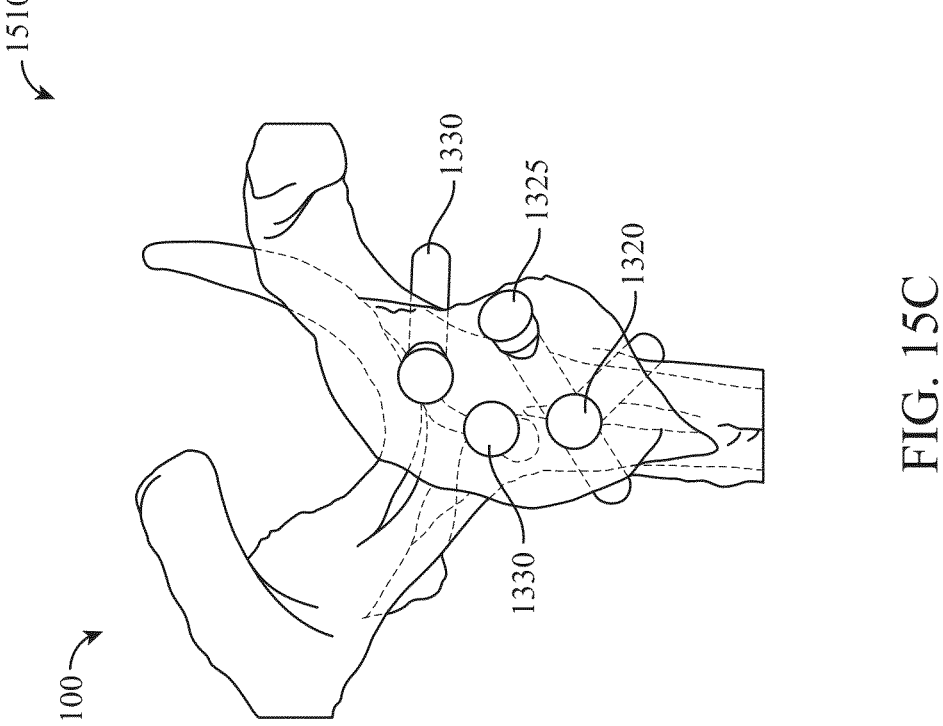

FIG. 15 illustrates a front side perspective view 1500 (FIG. 15A) of a glenoid with a skinny deformity, a back side perspective view 1505 (FIG. 15B) and a lateral side perspective view 1510 of the glenoid with the skinny deformity with a patient-specific screw configuration installed. Specifically, FIG. 15 illustrates a K1 skinny deformity, identified as a skinny deformity and further characterized as a K1 skinny deformity via the deformity classification process when a glenoid width measurement is less than 15 mm. A skinny type deformity is classified as a K1 deformity where lateralization should be minimized in order to maximize fixation due to a limited glenoid footprint The screw placement illustrated in FIGS. 15B and 15C include screw placements based on both the deformity classification, and a density mapping classification of the patient's anatomy. For example, the screw placement includes one index screw 1320 provided in the form of a lateral pillar screw, one other screw 1325, which often has no anterior or posterior edges and is typically found at the superior or inferior tubercles. There are two PLL screws 1330 which are positioned anterior if there is an anteverted fixation member (not shown). Alternatively, the PLL screws 1330 are positioned coracoid if there is a straight fixation member (not shown) relative to the baseplate. It will be appreciated that although only the screw configuration is shown in FIG. 15, that the patient-specific device configuration can further include a baseplate with a fixation member, screw holes, and an extrusion taper.

Although three non-limiting and illustrative deformity examples are shown in FIGS. 13-15, there are additional deformities and deformity classification possible. In one embodiment, the deformity classification process can identify a minimal planar deformity, a superior deformity, a posterior deformity, an anterior deformity, or a skinny deformity. These identified deformities can further be classified based on one or more attributes associates with the glenoid. For example, a minimal planar deformity can be classified as either medialized, vault lateral, or vault preserved. Each of these classifications can further be classified into subcategories (e.g., vault lateral into V1, V2, or V13 and vault preserved into VP1 or VP2). A superior deformity can be classified as superior lateral or superior medial. A posterior deformity can be classified as either a posterior inferior, a posterior lateral, a mega posterior, or a standard posterior deformity. Each of these classifications can further be classified into subcategories (e.g., posterior inferior into PI1 or PI2, and standard posterior deformity as either P1 or P2). A skinny type deformity can be further classified as either K1 or K2. Different screw patterns and patient-specific device configurations can be designed based on the specific subcategory classification of an identified deformity. The screw patterns and patient-specific device configurations can be further updated and otherwise customized based on the patient-specific bone density mapping process.

In some embodiments, the system and processes described herein can be used to create or otherwise generate a fixation plan or strategy, including a patient-specific recommendation for the configuration of, selection of, type of, orientation of, trajectory pattern of, and placement of one or more fixation members, screws, extrusion tapers, etc. In some embodiments, the fixation plan or strategy can include parameters related to threshold boundaries for the placement of the one or more fixation members, screws, extrusion tapers, etc. For example, based on the specific anatomical feature being evaluated, the system can establish one or more boundaries associated with the configuration of, selection of, type of, orientation of, trajectory pattern of, and placement of one or more fixation members, screws, extrusion tapers, etc. The one or more boundaries can be updated based on the output of the deformity identification/classification process, the density mapping process, or a combination thereof. For example, if a patient is identified as having a skinny type deformity (see FIG. 15), the system may implement physical boundaries and screw-type boundaries on the fixation plan and patient-specific device design based on the physical limitations of the patient's gyroid area.

Figure 16:
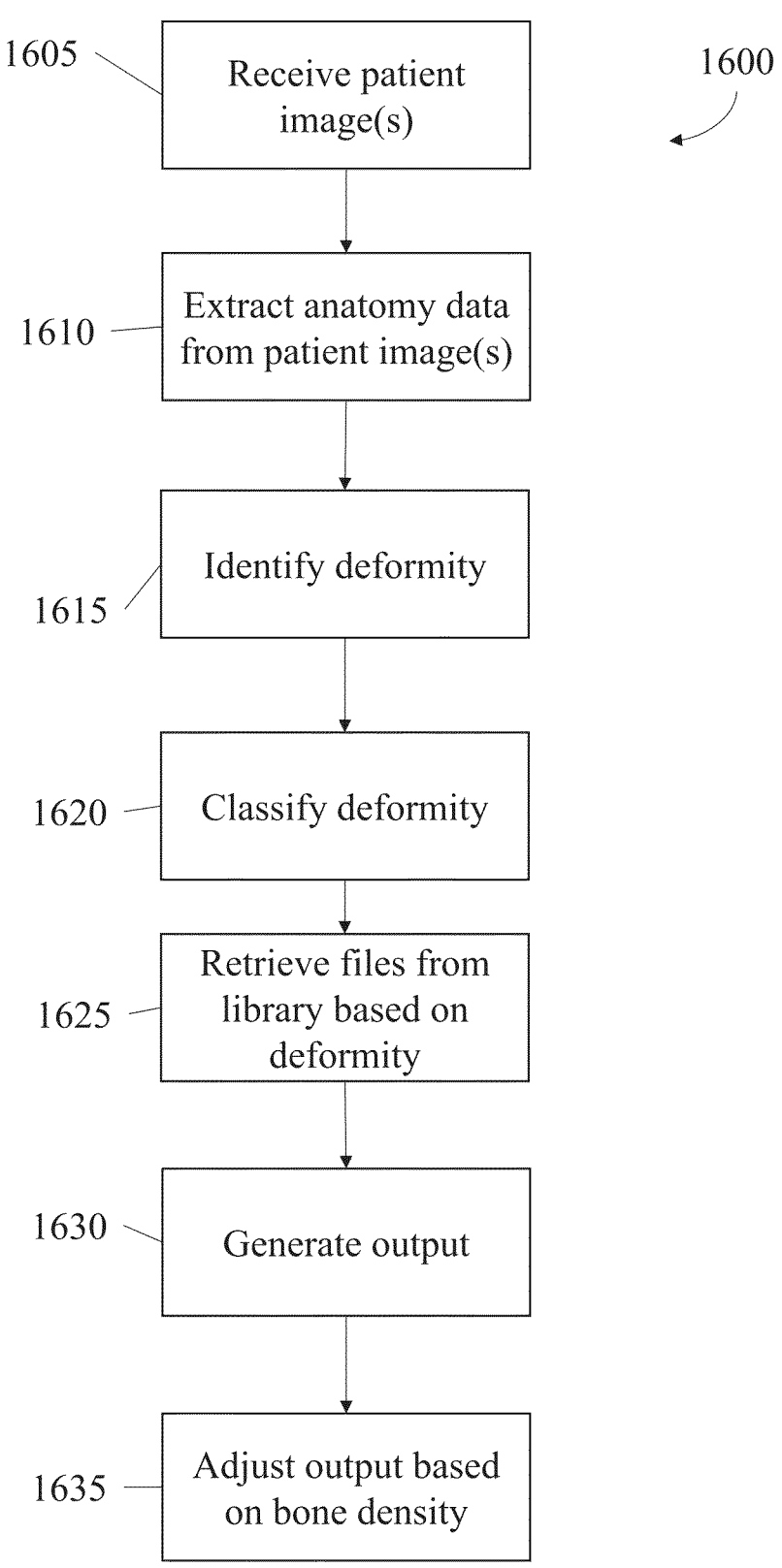
FIG. 16 is a flow chart of an exemplary patient-specific device production process, according to one embodiment.

FIG. 16 illustrates a deformity classification process 1600 using one or more artificial intelligence models. The deformity classification process 1600 can be configured to perform various advanced data analysis, image processing, and modeling techniques. In one example, the deformity classification process 1600 can use an iteratively trained learning model for providing dynamic analysis of a plurality of data elements and/or extracted features from one or more aspects of anatomical features of a patient. For example, the process 1600 can be configured to generate, train, and execute a plurality of nodes, neural networks, gradient boosting algorithms, mutual information classifiers, random forest classifications, and other artificial intelligence-related algorithms.

At step 1605, the system receives (or retrieves from memory) one or more 2D patient image files associated with a particular anatomical feature. The system can train and/or be trained based on a specific type of anatomical feature, implant, and/or medical procedure. In some embodiments, a database with a plurality of patient-specific device files classified by one or more attributes associated with one or more anatomical features is populated. In some embodiments, anatomy data associated with specific anatomical features can include data about a particular body part (e.g., left foot) or portion thereof (e.g., left ankle, or a segment of the left ankle joint). The anatomy data associated with specific anatomical features can include data elements and information about the specific anatomical feature being evaluated from not only the particular patient being considered but also the specific anatomical feature from an entire patient population dataset and an anatomy database. The anatomy database information can include data elements related to other anatomical features that may impact the specific anatomical feature being replaced or modified with a surgical implant. As a specific non-limiting example, if a patient has had Tommy John's surgery from a prior baseball injury, as indicated in the patient data, this data may be evaluated by the system during the analytics process(es) described herein, and additional anatomy data may be extracted and/or considered for generating an implant for a shoulder replacement, including but not limited to training and/or tuning the artificial intelligence model(s) based on patient population data for other patients that have had Tommy John's surgery.

In various embodiments, the system can process the 2D patient-specific image files using a segmentation process to generate the 3D digital representation of the patient anatomy. In some embodiments, the segmentation process can be executed using the one or more trained artificial intelligence models. In some embodiments, the 3D digital representation is transformed into a point cloud space and is input into the trained artificial intelligence model to perform a registration and/or alignment of the point cloud space (e.g., a non-rigid or rigid point cloud registration). In various embodiments, the registration and/or alignment of the point cloud space can be input into the trained artificial intelligence model with patient-specific image files and/or other patient population data. In one non-limiting example, the system creates a non-rigid shape reference based at least on portions of extracted anatomical data and information from the patient population data (e.g., the database of patient-specific device files). In this non-limiting example, a trained artificial intelligence model extracts information related to the patient's anatomical feature from the patient-specific image files and uses the non-rigid shape reference generated with the trained artificial intelligence model to create a patient-specific 3D digital representation from the patient-specific 2D grayscale image files. The system uses the trained artificial intelligence model(s) to create a non-rigid shape reference based on one or more features extracted from the patient-specific 2D grayscale image files, which is then used, in some embodiments, to transform contours and surface features of the patient-specific 2D grayscale image files into a 3D digital representation of the patient anatomy, including one or more patient-specific surface(s) and, in at least one embodiment, a density classification or mapping. In some embodiments, the patient-specific surfaces can include one or more porous areas, smooth or textured surface features, features of different thicknesses, and/or other surface features. It will be appreciated that other patient-specific configurations and surfaces are contemplated.

At step 1610, the system can extract data elements related to one or more anatomical features of a patient. In some embodiments, the patient image file includes a plurality of data elements, wherein each pixel and/or voxel can further include a plurality of data elements (e.g., metadata and other information).

At step 1615, the system can identify a deformity associated with the one or more anatomical features of the patient. In one embodiment, one or more attributes associated with a specific anatomical feature can be used to identify a deformity of the specific anatomical feature using an artificial intelligence model. For a non-limiting example, a deformity of a shoulder of a patient can be identified based on one or more measurements associated with a glenoid (e.g., version, tilt, CA Plane, GC, glenoid width, an edge of the acromion, and edge of the coracoid, a most lateral point of the glenoid, etc.). Although specific embodiments discussed herein include deformities related to the glenoid, it will be appreciated that the systems and processes described herein can be applied to other bones and joints, including but not limited to, bones of the ankle, hip, wrist, elbow, knee, feet, hands, or other bones in upper or lower extremities, spine, head, jaw and face, chest, and other suitable locations.

As will be understood, the systems and processes discussed herein may classify deformities (and densities) of any bones for creating surgical plans, instruments, implants, and devices worn on the outside of the body (e.g., masks, external fixation devices, etc.). For example, bones related to the talus, tibia, fibula, calcaneus, navicular, cuneiforms, tarsals, phalanges, and other bones related to the foot or ankle for foot and ankle implants, guides, or instruments, including, but not limited to total ankle replacement implants and tools. Further, the systems and processes discussed herein may classify deformities (and densities) of the femur, tibia, patella, pelvis, and other bones of the leg, knee, and hip (and spine) for implants, guides, and instruments related to the knee and hip (e.g., total or partial knee or hip replacement). Further still, the systems and processes herein may classify deformities and densities of the face, head, spine, wrist, elbow, rib cage, hands, neck, clavicle, for creating surgical plans, instruments, and implants, and related devices.

At step 1620, the system can classify the identified deformity based on one or more attributes. In some embodiments, the system uses an artificial intelligence model to retrieve and evaluate a plurality of patient-specific device files and select one or more aspects of the data extracted from the patient-specific image file that matches one or more attributes of the patient-specific device files. For example, once a deformity is identified, the system can generate, populate, or retrieve one or more measurements associated with the deformity in order to further classify the specific type of deformity, as described in connection with the non-limiting examples provided in FIGS. 13-15. In some embodiments, the system automatically detects, identifies, and classifies the deformity based on one or more attributes of the patient-specific device files and can automatically generate one or more measurements associated with the deformity and a related treatment plan (e.g., patient-specific device design, surgical plan, 3D model, etc.).

At step 1625, the system can populate a database with a plurality of patient-specific device files or retrieve the plurality of patient-specific files from a pre-populated database. The plurality of patient-specific files may be organized in a library that is categorized based on one or more attributes associated with one or more anatomical features. In some embodiments, the patient-specific device files include not only anatomy data associated with the particular anatomical feature being evaluated, but also other anatomical features that may impact the specific anatomical feature being replaced or modified with a surgical implant. In some embodiments, the patient-specific device files can include CAD files, digital representations, 3D models, images, schematics, software instructions, or other data or information related to the configuration of a patient-specific device or surgical plan.

At step 1630, the system generates an initial output based on the processing of the patient-specific device files in light of the deformity identification and classification steps. In some embodiments, the output can be provided in the form of a digital representation of a patient-specific device (e.g., drawing file, computer aided design (CAD) file, image file, video file, VR/AR scene file, application file, schematic, document, digital content, software command, programming instructions, 3D model file, graphical user interface (GUI), etc.). In some embodiments, the output can be provided in the form of a manufactured 3D device model, a surgical implant, a medical device, a surgical instrument, or other type of 3D-printed body. In some embodiments, the output can be provided in the form of a surgical plan, surgical strategy, device installation procedure, or similar.

At step 1635, the system analyzes the 3D digital representation of the patient anatomy using the density mapping process, described in more detail below in connection with FIG. 17, to update the initial output and generate an updated output based on density mapping of the patient's anatomy. In at least this way, the system output is customized to the patient's anatomy and bone density characteristics to improve osseointegration and surgical outcomes.

It will be appreciated that while the system is described as identifying/classifying deformities and then mapping a density associated with the patient data, that the data elements associated with both the deformity identification/classification and the density mapping processes can all be aggregated and analyzed via one or more artificial intelligence models to generate a patient-specific output without the steps relating to updating the output based on the density mapping characteristics, since the density mapping considerations will be evaluated in conjunction with the deformity evaluation.

Figure 17:
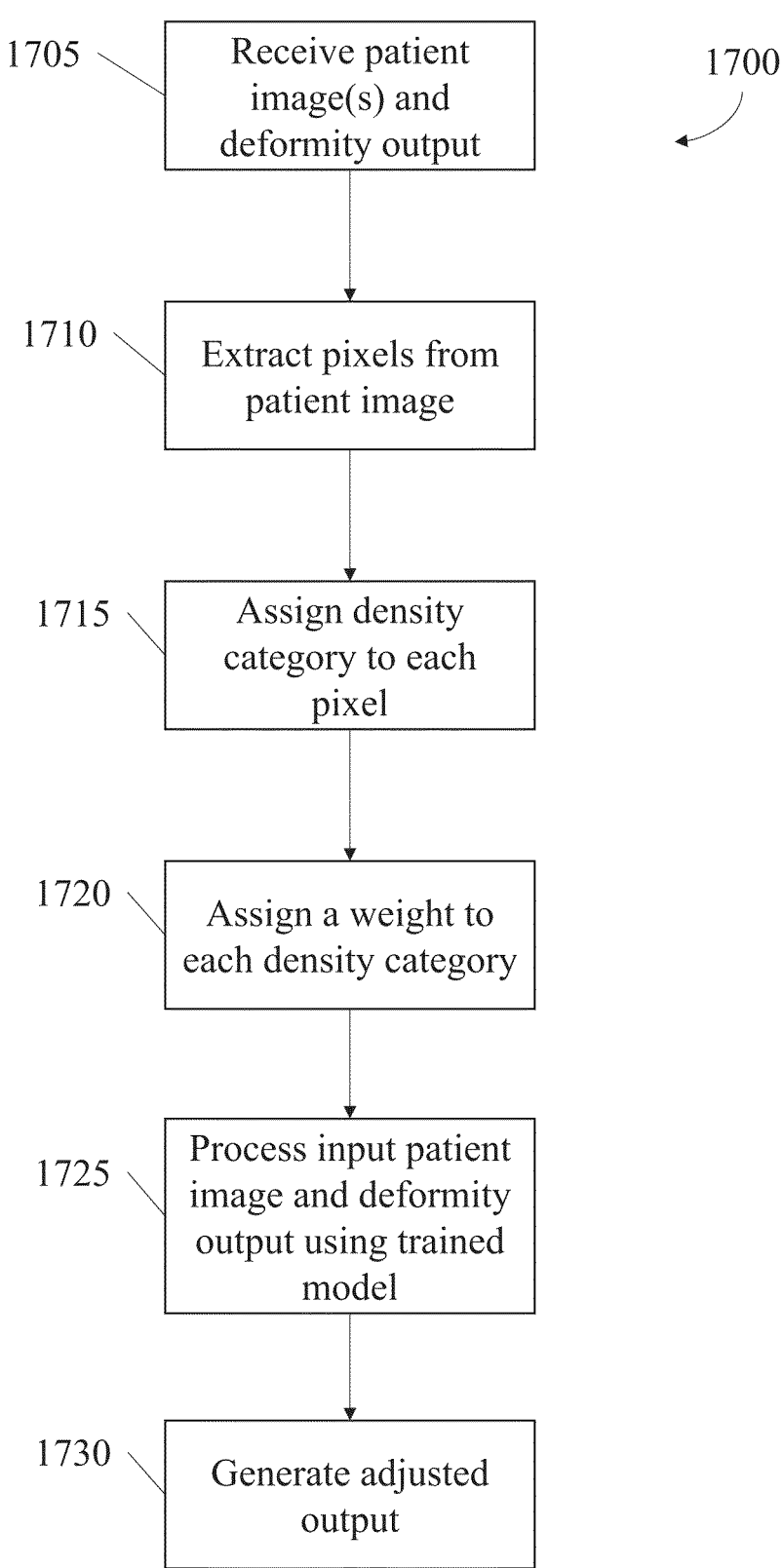
FIG. 17 is a flow chart of an exemplary bone density mapping process using one or more artificial intelligence models, according to one embodiment.

FIG. 17 illustrates the density-mapping process 1700 using one or more artificial intelligence models. The density-mapping process 1700 can be configured to perform various advanced data analysis, image processing, and modeling techniques. In one example, the density-mapping process 1700 can use an iteratively trained learning model for providing dynamic analysis of a plurality of data elements and/or extracted features from one or more aspects of anatomical features of a patient. For example, the density-mapping process 1700 can be configured to generate, train, and execute a plurality of nodes, neural networks, gradient boosting algorithms, mutual information classifiers, random forest classifications, and other artificial intelligence-related algorithms.

At step 1705, the system receives (or retrieves from memory) a patient image file associated with a particular anatomical feature. The system can train and/or be trained based on a specific type of anatomical feature, implant, and/or medical procedure. In some embodiments, the system receives, retrieves, analyzes, or otherwise processes the 3D digital representation of the patient anatomy generated from the 2D patient-specific image files.

At step 1710, the system can extract and process pixels from the patient-specific image file or voxels from the 3D digital representation of the patient anatomy. In some embodiments, the patient image file includes a plurality of data elements, wherein each pixel and/or voxel can further include a plurality of data elements (e.g., metadata and other information). In one embodiment, a specific anatomical feature of the bone-mapping process 1700 can include one or more data sets, which may be used for processing the plurality of data elements extracted from the patient image.

At step 1715, the system can identify a density category associated with each pixel or voxel, based on the plurality of data elements. In some embodiments, the density category associated with each pixel can be assigned a color based on the detected HU value(s) associated with each density category. The grayscale value(s) for each voxel in the 3D digital representation will hold the same grayscale value as a corresponding pixel in the 2D patient-image file because a slice by slice assignment of the color/associated density category. In at least this way, the system can create a colorized density classification scale 115 (see FIGS. 1-12), which can be used to generate a colorized density-mapped image of the patient anatomy, or a portion thereof. In some embodiments, the system can create a density classification scale using one or more arrays of HU values (e.g., without colorization). In some embodiments, the system can use a plurality of parameter values to generate the density category associated with each pixel or voxel of the patient image of the anatomical feature. In some embodiments, the system can assign a density category on a pixel-by-pixel or voxel-by-voxel basis without a colorization scale being applied to the image. In some aspects, the system may apply the density category based on the detected HU value(s) associated with each density category.

In some embodiments, one or more artificial intelligence models may be used to generate the density categories associated with each pixel or voxel based on the HU values or other parameters. In some embodiments, the system can utilize a plurality of trained learning models to output specific density parameters or metrics tailored to certain design details of the anatomical feature. In some embodiments, one or more density categories may have different properties or be assigned based on a targeted therapeutic benefit. In some embodiments, a pixel-by-pixel or voxel-by-voxel classification may be assigned by the system based on one or more properties other than the density classification. In some forms, the system may assign a classification based at least partially on density in combination with some other information (e.g., data element(s), defect size, bone length, etc.).

In some embodiments, the system can assign a weight or emphasis guideline with each density category associated with each pixel at step 1720. The system can use the assigned weight in order to update a model or other digital representation of the patient anatomy based on a density parameter (e.g., patient-specific surfaces). In some embodiments, the system can update one or more aspects of the digital representation, rerunning the artificial intelligence model(s) to determine if the output digital representation is within a preconfigured threshold value range. If the output is within the preconfigured threshold as determined by step 1720, the updated weights and/or emphasis guidelines may be saved, and the system can save the updated artificial intelligence model(s) as the trained artificial intelligence model(s).

At step 1725, the input patient image is processed using the trained artificial intelligence model(s) to generate the colorized density-mapped patient image shown in FIGS. 1-12. In some embodiments, the colorized density-mapped patient image can be the output generated by the process at step 1730. In some forms, the process generates a CAD file associated with the patient-specific image file. In some embodiments, the CAD file generated can be an updated CAD file compared to the initial output described in connection with FIG. 16 for a patient-specific device 205. In some embodiments, the process generates a design (or an updated design) for a patient-specific device, based on one or more of the density parameters and/or the density classification of one or more portions of the patient's anatomy. For example, the system may design a patient-specific device with a off-normal orientation based on the patient's specific anatomy and the identified density classification on a pixel-by-pixel or voxel-by-voxel basis. In at least this way, the system and processes described herein provide a detailed and highly personalized device design for implants and other medical devices based on the pixel-by-pixel or voxel-by-voxel density-mapped patient anatomy.

Figure 18:
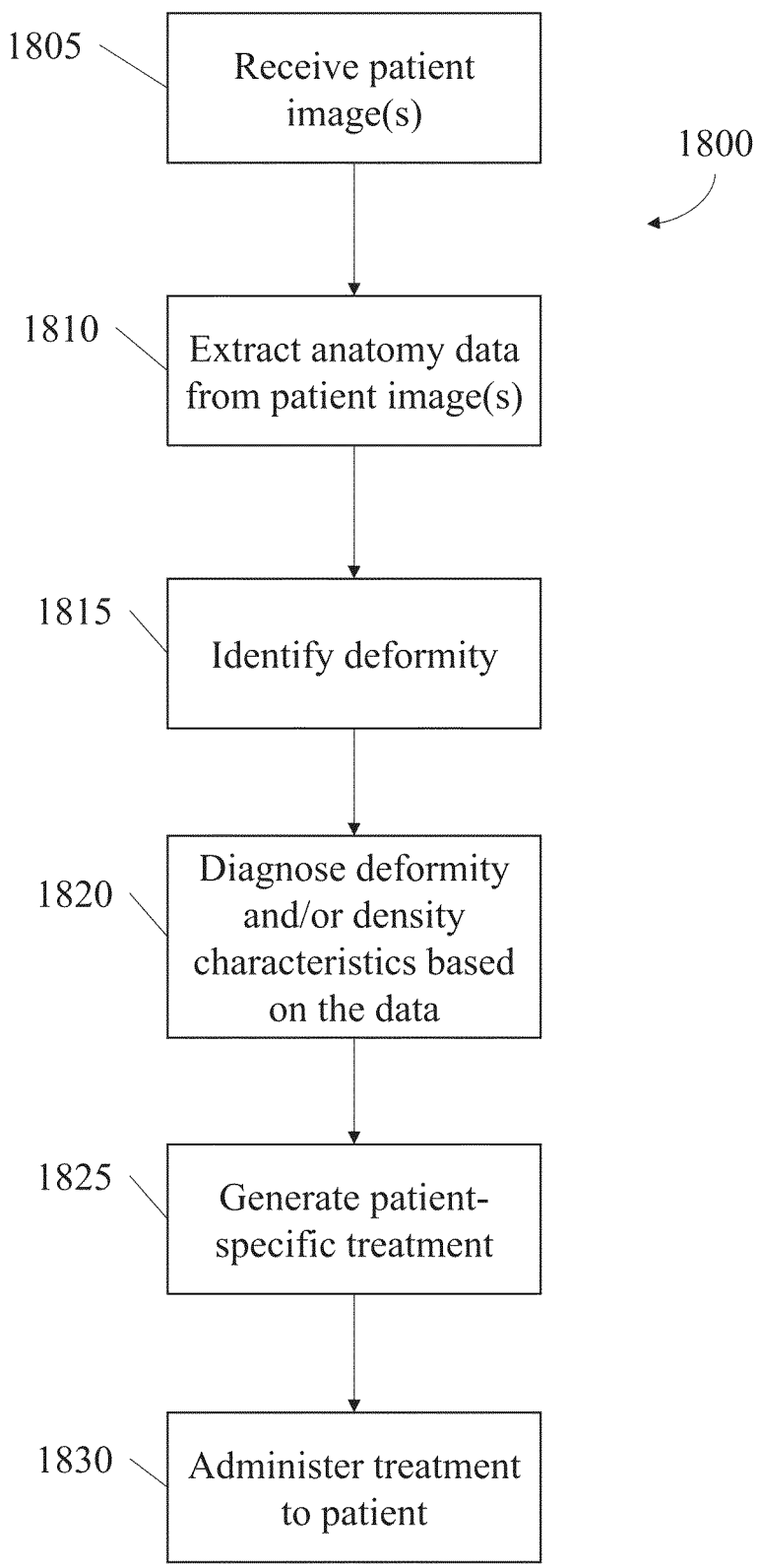
FIG. 18 is a flow chart of an exemplary diagnostic and treatment process, according to one embodiment.

As shown in FIG. 18, an exemplary diagnostic and treatment process 1800 is described, according to one embodiment of the present disclosure. In various embodiments, the system may receive one or more patient-specific image files at steps 1805. The patient-specific image files can be processed at step 1810 when one or more aspects of anatomy data are extracted from the patient-specific image files, the one or more aspects of the anatomy data associated with one or more anatomical features. At step 1815, a deformity associated with a patient's anatomy can be identified based on one or more attributes. As shown in step 1820, in several embodiments, a deformity classification can be diagnosed by analyzing the patient-specific image file using one or more machine learning models. Further, additional diagnostics can be determined at step 1820 based on a density mapping of the patient's anatomy. A patient-specific treatment can be generated to address and/or correct one or more of the identified and classified deformities and/or bone density issues/anomalies. In many embodiments, the treatment administered at step 1830 to correct or address the identified issues includes recommending or performing a surgical procedure, generating or manufacturing a patient-specific device, or developing a surgical plan or strategy recommendation, or similar treatments. In some embodiments, surgical plans can be further updated, via an artificial intelligence model or otherwise, based on one or more surgeon preferences.

The data analysis and implant generation technique(s) described herein are an improvement over the prior art for many reasons, but at least in that the embodiments described herein do not limit data analysis to the best fit or nearest neighbor techniques and instead intelligently considers all relevant data elements associated with an anatomical feature, including those not directly related in order to design and generate a patient-specific surgical device. It will be appreciated that the data analysis and modeling techniques are not limited to those described in the embodiment described in connection with FIGS. 16-18 and other modeling techniques and analysis processes are contemplated within the scope of the present disclosure.

It will be appreciated that the system can design, generate, and/or update one or more surfaces and/or textures to the generated CAD file and/or to the implant/device generated at step 1630 including but not limited to a lattice structure, gyroid structure, surface texture, holes or apertures, threads, etc. In some embodiments, a plurality of implants may be generated at step 1630. For example, the system can create a test implant in addition to the implant to be used in the patient, for a provider to practice before the surgical procedure. In another non-limiting embodiment, the process 1600 may generate a plurality of implants in various sizes at step 1630, which can be further customized based on the patient's density mapping outcomes. In this example, the provider can field-test the appropriate fit of the updated device/implant as needed during the operation without requiring any modifications to the implant. In some embodiments, the test implant can be compared to the 3D digital representation, either physically or digitally, to facilitate the field-test. In some embodiments, the system can receive feedback data to be processed in a feedback model to improve the advanced analytic and artificial intelligence processes described herein.

In at least one embodiment, the density-mapped classification can be used as part of an intelligent planning process to analyze and predict periprostatic fracture risk. In this example, a density-mapped classification of one or more portions of the patient anatomy may indicate a range of bone strength (e.g., strong bone to weak bone). In at least this way, the density-mapped image may be used to intelligently plan a surgical procedure and/or device placement to minimize the risk of a periprostatic fracture. In some embodiments, the objective analysis of the bone strength and/or other aspects of the intelligent planning process can be executed by one or more trained artificial intelligence models.

According to particular embodiments, systems discussed herein may be configured to receive or access density data related to a particular patient's anatomy (density data discussed herein). In at least one embodiment, the system may compute a prediction of one or more areas of the particular patient's anatomy that might be prone to fracture during certain procedures (or post-procedure) based on one or more machine learning or artificial intelligence models. In these embodiments, the system may train the artificial intelligence model based on pre-fracture density data and post-fracture imaging or data and adjust weights and/or emphasis guidelines based on the accuracy of the model predicting fracture. As will be understood from this discussion, this disclosure contemplates the use of density data and certain artificial intelligence models as a standalone fracture prediction system.

In at least one embodiment, the system may be configured to leverage fracture prediction as one of several factors in an artificial intelligence model for surgical planning and/or device creation. For example, the system may be configured to ingest density data and predict or define certain areas of patient anatomy that might be prone to fracture. Continuing with this example, the system may create a surgical plan and/or device based on this fracture analysis, along with density data (separate from the fracture analysis), and other patient/anatomy data.

In at least one embodiment, the density-mapped classification of one or more portions of the patient anatomy may be used as an input into one or more artificial intelligence models for designing a patient-specific input. In some embodiments, the density classification values may be input into an advanced patient-specific device generation to create customized surgical plans and generate more accurate patient representations. It will be appreciated that the classification values and/or categorization of the pixel-by-pixel or voxel-by-voxel analysis can be processed with or without colorization. The output of the density-mapped images (with or without colorization) can be used to visually illustrate different density classification between various regions of the patient anatomy for surgeons and other medical providers, which may have multiple clinical benefits.

One skilled in the art will understand that processes discussed herein can include machine learning processes and other advanced artificial intelligence processes. For example, the system and processes of the present disclosure can perform diagnostics, image analysis, generate tasks or action items, provide customized recommendations according to user settings and preferences, generate 3D device models, generate surgical plans, generate CAD files, generate operating instructions for a surgical robot, generate personalized implant designs, generate notifications, and similar processes. Further, in at least one embodiment, the systems and processes discussed herein may provide an input to an additional process (e.g., surgery performed by a robot) or may be part of another process. In some embodiments, the system may use additional inputs and/or feedback loops to an iterative training process for a personalized implant generation process based on a plurality of parameters and adjustable metric values. Examples of such processes can be found in U.S. patent application Ser. No. 18/454,580, filed Aug. 23, 2023, and entitled "PATIENT-SPECIFIC MEDICAL DEVICES AND ADDITIVE MANUFACTURING PROCESSES FOR PRODUCING THE SAME", incorporated by reference herein in its entirety.

In some embodiments, the system can include a process for generating customized surgical plans that are populated for approval by a medical provider, surgeon, or similar healthcare professional. In various embodiments, the customized surgical plans can include one or more operating instructions to be transmitted to, installed on, or otherwise executed by a surgical robot or similar device. In some embodiments, the surgical robot can be autonomous or semi-autonomous.

As an example, implants, instruments, surgical plans, techniques, or information related to implants, instruments, surgical plans, or techniques, may be download, saved, or otherwise captured within a file for use with a surgical robot, navigation system, or in another surgical setting. In at least one embodiment, the surgical plan may be transmitted to a surgical robot, navigation system, or other operating room system or device via a wireless transmission system (e.g., cellular, wifi, or other data transfer mechanism). Some non-limiting examples of file types that may be generated and/or transmitted include, but are not limited to: DICOM, STL, OBJ, TIFF, BMP, JPEG, AMF, 3MF, PLY, FBX, STEP/IGES, NIfTI, PDF, DOCX, CSV, .PRT, .ASM, .SLDPRT, .SLDASM, .PLAN, .NWD, .NWF, VRML, MIMICS, .DWG, etc.

In one non-limiting embodiment, the surgical robot can include a controller, a processor, a memory unit, a surgery module, a vision system (and/or other navigation systems), a sensor module, and a communication module. In various embodiments, the surgical robot may include a processor designed to execute patient-specific instructions to the surgery module to perform various actions associated with a surgical procedure. In some embodiments, the controller is designed to communicate with the processor and the memory unit to execute instructions to control one or more aspects of the surgery module. In some embodiments, the controller can be provided in the form of a virtual reality (VR) and/or augmented reality (AR) headset or similar controller. In some embodiments, the surgery module can include one or more articulating arms, one or more surgical devices (e.g., scalpel, retractor, drill, saw, suture instrument, suction, electrocautery, etc.), attachment(s) for accessories, or a combination thereof. In some embodiments, the surgical robot can also include a vision system used to track the movement of one or more aspects of the surgery module, a patient, a surgeon, the surgical environment, etc. As will be understood, the surgical robot may include or be in communication with other navigation systems, including, but not limited to, radar or sensor-based navigation (e.g., Bluetooth or BLE) and such instructions discussed herein may include instructions on navigation via one or more navigation systems. In various embodiments the surgical robot can utilize the sensor module to receive feedback signals related to the surgical operations or other actions performed by the surgical robot, patient, surgeon, or environment to compensate for changes during surgery or to otherwise facilitate execution of a surgical plan. In some embodiments, the sensor module is operatively coupled to the controller of the surgical robot. The communication module can be used to send instructions, feedback, signals, or other data between one or more aspects of the surgical robot, the surgeon, a computing system, or a combination thereof. In some embodiments, the communication module can be designed to generate notifications, transmit updated imaging, initiate safety alerts, send signals to particular surgical devices to indicate an implant is properly (or improperly aligned), or similar data related to various actions or tasks being executed by the surgical robot, the surgeon, the medical team, or other aspects of the system or processes described herein.

In various embodiments, exemplary systems may receive information or feedback from a surgical robot or navigation system and update a machine learning process, one or more emphasis guidelines, weighting factors, or like processes or parameters to create a feedback loop to improve an existing surgical plan or a future surgical plan.

The present systems and processes may be used for designing and producing surgical plans, instruments, and implants leveraging any materials alone or in combination. For example, the present systems and processes may include an implant or instrument that is made entirely or partially of titanium, cobalt chrome, or another suitable metal material. As another example, the systems and processes may include an implant or instrument that is made entirely or partially of a plastic or a polymer, such as, PAEK or a member of the PAEK family (e.g., PEEK), which may be 3D-printed or manufactured in another way. As yet another example, the systems and processes may include an implant or instrument made of a ceramic material (e.g., alumina, zirconia, or other materials).

The embodiments were chosen and described in order to explain the principles of the claimed embodiment and their practical application so as to enable others skilled in the art to utilize the embodiment and various embodiments and with various modifications as are suited to the particular use contemplated. Alternative embodiments will become apparent to those skilled in the art to which the claimed embodiments pertain without departing from their spirit and scope. Accordingly, the scope of the claimed embodiments is defined by the appended claims rather than the foregoing description and the exemplary embodiments described therein.

What is claimed is:

1. A medical device production process comprising:
populating a database with a plurality of patient-specific device files classified by one or more attributes associated with one or more anatomical features;
receiving a 2D patient-specific grayscale image file associated with a shoulder of a patient;
generate a 3D digital representation of the shoulder of a patient based on the 2D patient-specific grayscale image file using a non-rigid shape reference;
processing the 3D digital representation of the shoulder including:
identifying a deformity associated with the shoulder based on at least one of the one or more anatomical features;
classifying the deformity of the shoulder based on an attribute of the one or more attributes; and
determining a density mapping of the shoulder using an intelligent density mapping model, wherein the density mapping is determined on a voxel-by-voxel basis;
retrieving at least one of the plurality of patient-specific device files classified by the attribute of the one or more attributes;
creating an initial baseplate system design based on the at least one of the plurality of patient-specific device files, the initial baseplate system design comprising a fixation member and a plurality of screw holes, wherein each of the fixation member and the one or more screw holes are oriented at one or more angles;
creating an updated baseplate system design by adjusting at least one angle of the one or more angles of each of the fixation member and the plurality of screw holes based on the density mapping; and transmitting a digital representation of at least a portion of the updated baseplate system design to a 3D printer for manufacturing at least a portion of a baseplate system based on the updated baseplate system design.

2. The medical device production process of claim 1, wherein the baseplate system comprises at least a portion of the fixation member, the plurality of screw holes, or a combination thereof.

3. The medical device production process of claim 2, wherein one or more of the fixation member and the plurality of screw holes are integrally formed with an implant device.

4. The medical device production process of claim 3, wherein each screw hole of the plurality of screw holes is oriented at an angle based on the deformity classification, the density mapping, or combination thereof.

5. The medical device production process of claim 1, wherein determining the density mapping of the shoulder further comprises:
extracting voxels from the patient-specific 3D digital representation;
assigning a density category of a plurality of density categories to each of the extracted voxels;
assigning a weight to each of the plurality of density categories; and
processing the patient-specific 3D digital representation file via an artificial intelligence model to create the density mapping based on the weight of each of the plurality of density categories assigned to each of the extracted voxels.

6. The medical device production process of claim 1, wherein the deformity associated with the shoulder is provided in the form of a glenoid deformity that is identified at least in part by comparing the patient-specific grayscale image file to the plurality of patient-specific device files.

7. The medical device production process of claim 1, wherein the initial baseplate system design is based on a compilation of the plurality of patient-specific device files.

8. The medical device production process of claim 1, wherein the digital representation is generated at least in part by processing the one or more attributes associated with the one or more anatomical features, the plurality of patient-specific device files, and the density mapping via an artificial intelligence model.

9. A medical device production process comprising:
populating a database with a plurality of patient-specific device files classified by one or more attributes associated with one or more anatomical features;
receiving a patient-specific grayscale image file associated with a shoulder of a patient;
processing the patient-specific grayscale image file including:
identifying a deformity associated with the shoulder based on at least one of the one or more anatomical features;
classifying the deformity of the shoulder based on an attribute of the one or more attributes; and
determining a density mapping of the shoulder using an intelligent density mapping model;
retrieving at least one of the plurality of patient-specific device files classified by the attribute of the one or more attributes;
creating an initial baseplate system design based on the at least one of the plurality of patient-specific device files, the initial baseplate system design comprising a fixation member at an angle;

creating an updated baseplate system design by adjusting the angle of the fixation member based on the density mapping; and transmitting a digital representation of at least a portion of the updated baseplate system design to a 3D printer for manufacturing at least a portion of a baseplate system based on the updated baseplate system design.

10. The medical device production process of claim 9, wherein the updated baseplate system design comprises a configuration for at least a portion of the fixation member, a plurality of screw holes, or a combination thereof.

11. The medical device production process of claim 10, wherein one or more of the fixation member, and the plurality of screw holes are integrally formed with an implant device.

12. The medical device production process of claim 11, wherein each screw hole of the plurality of screw holes is oriented at an angle based on the deformity classification, the density mapping, or combination thereof.

13. The medical device production process of claim 9, wherein the baseplate system comprises at least a portion of the fixation member, a plurality of screw holes, or a combination thereof.

14. The medical device production process of claim 9, wherein determining the density mapping of the shoulder further comprises:

extracting pixels from the patient-specific grayscale image file;

assigning a density category of a plurality of density categories to each of the extracted pixels;

assigning a weight to each of the plurality of density categories; and processing the patient-specific grayscale image file via an artificial intelligence model to create the density mapping based on the weight of each of the plurality of density categories assigned to each of the extracted pixels.

15. The medical device production process of claim 9, wherein the deformity associated with the shoulder is provided in the form of a glenoid deformity that is identified at least in part by comparing the patient-specific grayscale image file to the plurality of patient-specific device files.

16. The medical device production process of claim 9, wherein the initial baseplate system design is based on a compilation of the plurality of patient-specific device files.

17. The medical device production process of claim 9, wherein the digital representation is generated at least in part by processing the one or more attributes associated with the one or more anatomical features, the plurality of patient-specific device files, and the density mapping via an artificial intelligence model.

* * * * *